US009845341B2

(12) United States Patent
Waldor et al.

(10) Patent No.: US 9,845,341 B2
(45) Date of Patent: Dec. 19, 2017

(54) VIBRO-BASED DELIVERY SYSTEM AND IMMUNE SUPPRESSION

(71) Applicant: THE BRIGHAM AND WOMEN'S HOSPITAL, INC., Boston, MA (US)

(72) Inventors: Matthew Waldor, Newton, MA (US); Xiaohui Zhou, Newton, MA (US); Benjamin Gewurz, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/770,919

(22) PCT Filed: Mar. 11, 2014

(86) PCT No.: PCT/US2014/022986
§ 371 (c)(1),
(2) Date: Aug. 27, 2015

(87) PCT Pub. No.: WO2014/164607
PCT Pub. Date: Oct. 9, 2014

(65) Prior Publication Data
US 2016/0017007 A1   Jan. 21, 2016

Related U.S. Application Data

(60) Provisional application No. 61/776,237, filed on Mar. 11, 2013.

(51) Int. Cl.
*C07K 14/28* (2006.01)
*A61K 35/74* (2015.01)
*A61K 39/02* (2006.01)

(52) U.S. Cl.
CPC .............. *C07K 14/28* (2013.01); *A61K 35/74* (2013.01); *A61K 39/02* (2013.01); *C07K 2319/00* (2013.01); *C07K 2319/20* (2013.01); *C07K 2319/31* (2013.01); *C07K 2319/40* (2013.01); *C07K 2319/50* (2013.01); *C07K 2319/60* (2013.01)

(58) Field of Classification Search
CPC .... A61K 39/02; A61K 39/104; A61K 39/106; A61K 39/108; A61K 39/112; A61P 37/04
USPC ................................ 435/200.1, 252.1, 235.1
See application file for complete search history.

(56) References Cited

U.S. PATENT DOCUMENTS 6,077,515 A   6/2000  Barbour et al.
6,203,799 B1  3/2001  Mekalanos et al.
(Continued)

FOREIGN PATENT DOCUMENTS

WO   01/68829 A2    9/2001
WO   2007/112518 A1 10/2007

OTHER PUBLICATIONS

Makino et al., Lancet. 361:743-749 (2003).*
(Continued)

*Primary Examiner* — Jana A Hines
(74) *Attorney, Agent, or Firm* — Nixon Peabody LLP; David S. Resnick; Tari W. Mills

(57) ABSTRACT

Embodiments described are immunosuppressant therapeutics and compositions comprising a Vop protein derived from *Vibro parahaemolyticus*; and drug delivery vehicles derived from a *V. parahaemolyticus* expressing a mutant VopZ protein lacking amino acid residue 38-62.

1 Claim, 12 Drawing Sheets

| SPOT | NAME (LOCUS) | PUTATIVE FUNCTION/MOTIF (REF) |
|---|---|---|
| 1 | VopV (Vpa1357) | effector, binds actin (Hiyoshi et al., 2011) |
| 2-9 | VopD2 (Vpa1361) | translocator (Kodama et al., 2008) |
| 10,11 | VopL (Vpa1370) | effector, actin nucleator (Liverman et al., 2007) |
| 12 | VopW (Vpa1345) | translocator (Zhou et al., 2012) |
| 13-19 | non-vibrio proteins | |
| 20* | VopZ (Vpa1336) | effector (this paper) |
| 21 | VopT (Vpa1327) | effector, ADP-ribosyltransferase (Kodama et al., 2007) |
| 22 | VopA (Vpa1346) | effector, Ser/Thr acetyltransferase (Trosky et al., 2007) |
| 23 | imp (Vp0323) | immunogenic protein |
| 24 | VopC (Vpa1321) | effector, deamidase (Akeda et al., 2011) |
| 25* | (Vpa1350) | DUF912, possible T3SS2 component (this paper) |
| 26 | ClpB (Vp0561) | ?protease, AAA ATPase (Makino et al., 2003) |
| 27 | PflD (Vp0994) | Pyruvate formate lyase (Makino et al., 2003) |
| 28* | (Vpa1343) | possible needle protein (this paper) |
| 29 | VopcC(Vpa1334) | chaperone for VopC (Akeda et al., 2011) |
| 30 | GlyA(Vp0715) | serine hydroxymethyltransferase |

(56) References Cited

U.S. PATENT DOCUMENTS

| | | |
|---|---|---|
| 2001/0021386 A1 | 9/2001 | Nuijten et al. |
| 2007/0167426 A1 | 7/2007 | Siddiqui et al. |
| 2008/0274136 A1 | 11/2008 | Ma et al. |
| 2013/0017218 A1 | 1/2013 | Waldor et al. |

OTHER PUBLICATIONS

Gotoh et al., (PLOS. 2010. vol. 5(10)).*

Kodama et al., (PLOS. 2010. vol. 5(1)).*

Akeda et al., Biochemical and Biophysical Research Communications, 427:242-247 (2012). "Functional cloning of Vibrio parahaemolyticus type III secretion system 1 in *Escherichia coli* K-12 strain as a molecular syringe."

Arnold et al., PLOS Pathology, 5(4):e1000376 (2009). "Sequence-Based Prediction of Type III Secreted Proteins."

Cohen et al., Infection and Immunity, 70(4):1965-1970 (2002). "Randomized, controlled human challenge study of the safety, immunogenicity, and protective efficacy of a single dose of Peru-15, a live attenuated oral cholera vaccine."

Doring et al., Vaccine, 26:1011-1024 (1998). "Vaccines and Immunotherapy against Pseudomonas aeruginosa Pulmonary Infection."

Dutta and Habbu, Brit J Pharmacol, 10:153-159 (1955). "Experimental cholera in infant rabbits: a method for chemotherapeutic investigation."

Feldman et al., Infection and Immunity, 66:43-51 (1998). "Role of Flagella in Pathogenesis of Pseudomonas aeruginosa Pulmonary Infection."

Galan et al., Nature Reviews, 444:567-573 (2006). "Protein delivery into eukaryotic cells by type III secretion machines."

GenBank Accession No. BA000032, Vibrio parahaemolyticus RIMD 2210633 DNA, chromosome, complete sequence, May 19, 2007 [found online May 29, 2014]. sequence n. a. positions 1409747-1408995.

GenBank Accession No. EFO35293, conserved hypotherical protein [Vibrio parahaemolyticus Peru-466] Oct. 10, 2010 [found online May 29, 2014]. sequence.

Grynberg et al., PLOS Pathogens, 5(4):e1000398 (2009). "The Signal for Signaling, Found."

Harrison et al., Infection and Immunity, 76(12):5524-5534 (2008). "Vibrio cholerae flagellins induce toll-like receptor 5-mediated Interleukin-8 production through mitogen-activated protein kinase and NF-kappaB activiation."

Hegazy et al., Infect Immunol, 80(3):1193-1202 (2012). "Evaluation of *Salmonella enterica* Type III Secretion System Effector Proteins as Carrier for Heterologous Vaccine Antigens."

IMBA—Institute of Molecular Biotechnology, online webpage retrieved Nov. 9, 2012. http://www.imba.oeaw.ac.at/research/thomas-marlovits/research/?P=1&no_cache=1.

Kenner et al., The Journal of Infectious Diseases, 172(4):1125-1129 (1995). "Peru-15, an improved live attenuated oral vaccine candidate for Vibrio cholera O1." Abstract only.

Kodama et al., PLoS One, 5:e8678 (2010). "Two Regulators of Vibrio parahaemolyticus Play Important Roles in Enterotoxicity by Controlling the Expression of Genes in the Vp-PAI Region."

Rui et al., PNAS, 107:4359-4364 (2010). "Reactogenicity of Live-attenuated Vibrio cholerae Vaccines is Dependent on Flagellins."

Samudrala et al., PLoS Pathogens, 5(4):e10000375 (2009). "Accurate Prediction of Secreted Substrates and Identification of a Conserved Putative Secretion Signal for Type III Secretion Systems."

Spira et al., Infection and Immunity, 32(2):739-747 (1981). "Simple adult rabbit model for vibrio cholera and enterotoxigenic *Escherichia coli* diarrhea."

Ward, Thesis submitted for the degree of Doctor of Philosophy for Institute of Child Health, University College London (2010). 281 pages. "Lentiviral Vectors for Treatment of Haemophilia."

Xicohtencatl-Cortes et al., Molecular and Cellular Proteomics, 5:2374-2383 (2006). "Identification of Proinflammatory Flagellin Proteins in Supernatants of Vibrio cholerae O1 by Proteomics Analysis."

Yoon et al., Infection and Immunity, 76(3):1282-1288 (2008). "Decreased potency of the Vibrio cholerae sheathed flagellum to trigger host innate immunity."

Zhou et al., "Heterologous expression of vibrio parahemolytics DNA idnetifies potential type III secretation proteins", Applied and Enviromental Microbiology AEM-07997, p. 11 (2012).

Zhou et al., "A vibrio parahaemolyticus T3SS effector mediates pathogenesis by independently enabling intestinal colonization and inhibiting TAK1 action" Cell Reports 3:1690-1702 (2013).

* cited by examiner

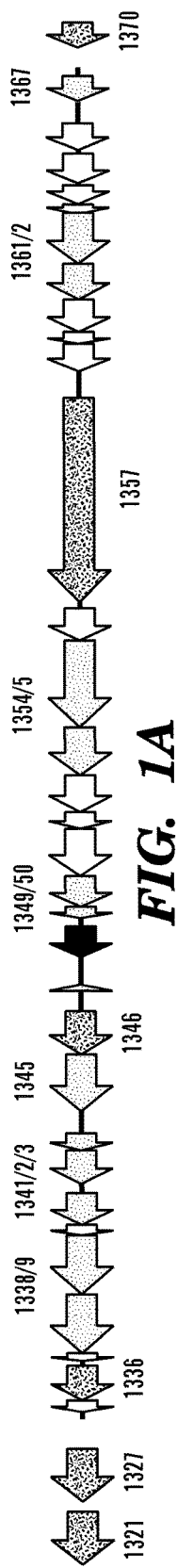

FIG. 1A

| SPOT | NAME (LOCUS) | PUTATIVE FUNCTION/MOTIF (REF) |
|---|---|---|
| 1 | VopV (Vpa1357) | effector, binds actin (Hiyoshi et al., 2011) |
| 2-9 | VopD2 (Vpa1361) | translocator (Kodama et al., 2008) |
| 10,11 | VopL (Vpa1370) | effector, actin nucleator (Liverman et al., 2007) |
| 12 | VopW (Vpa1345) | translocator (Zhou et al., 2012) |
| 13-19 | non-vibrio proteins | |
| 20* | VopZ (Vpa1336) | effector (this paper) |
| 21 | VopT (Vpa1327) | effector, ADP-ribosyltransferase (Kodama et al., 2007) |
| 22 | VopA (Vpa1346) | effector, Ser/Thr acetyltransferase (Trosky et al., 2007) |
| 23 | imp (Vp0323) | Immunogenic protein |
| 24 | VopC (Vpa1321) | effector, deamidase (Akeda et al., 2011) |
| 25* | (Vpa1350) | DUF812, possible T3SS2 component (this paper) |
| 26 | ClpB (Vp0561) | ?protease, AAA ATPase (Makino et al., 2003) |
| 27 | PflD (Vp0994) | Pyruvate formate lyase (Makino et al., 2003) |
| 28* | (Vpa1343) | possible needle protein (this paper) |
| 29 | VopcC (Vpa1334) | chaperone for VopC (Akeda et al., 2011) |
| 30 | GlyA (Vp0715) | serine hydroxymethyltransferase |

FIG. 1B

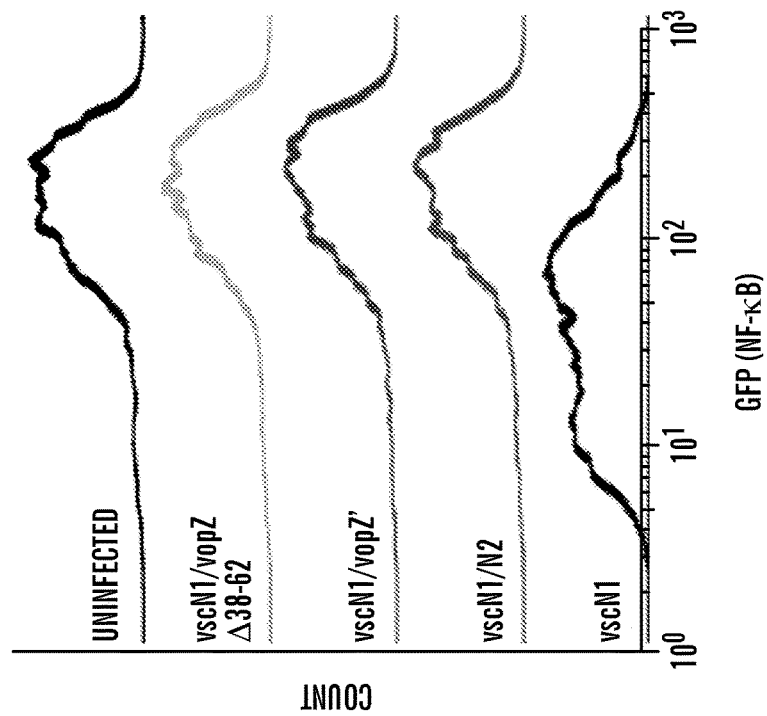
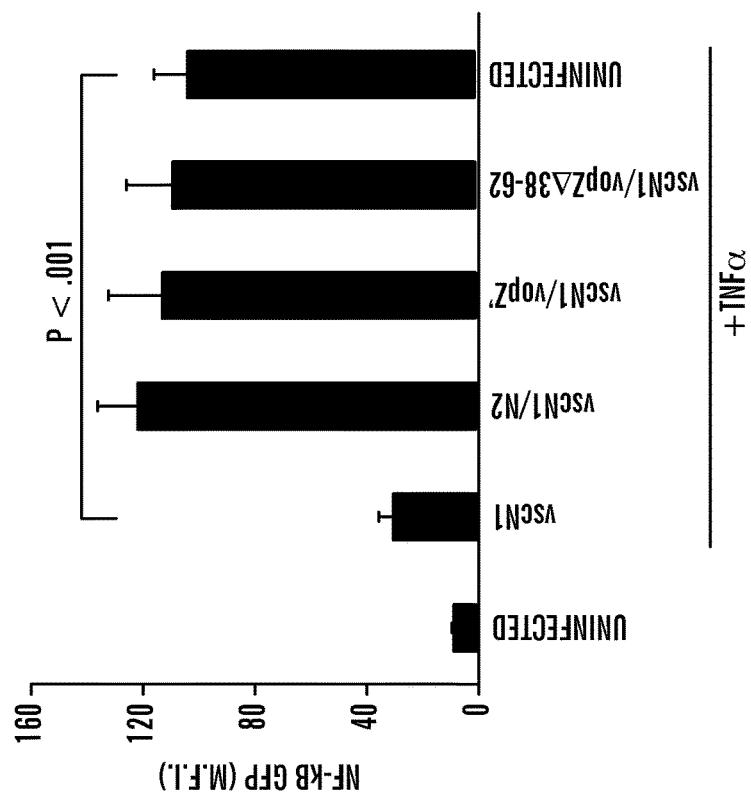
FIG. 4A
FIG. 4B

US 9,845,341 B2

VIBRO-BASED DELIVERY SYSTEM AND IMMUNE SUPPRESSION

CROSS REFERENCE TO RELATED APPLICATION

This application is a 35 U.S.C. §371 National Stage Application of International Application No. PCT/US2014/022986 filed on Mar. 11, 2014, which designates the United States, and which claims the benefit under 35 U.S.C. §119(e) of U.S. Provisional Application No. 61/776,237 filed Mar. 11, 2013, the contents of each application are incorporated herein by reference in its entirety.

GOVERNMENT SUPPORT

This invention was made with Government support under Grant No. R37 AI-42347 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Mar. 11, 2014, is named 043214-076051-PCT_SL.txt and is 33,376 bytes in size.

FIELD

The present disclosure relates to immunosuppressant therapeutics, compositions and drug delivery.

BACKGROUND

When the immune system in an organism is no working properly, the malfunction can lead to a host of diseases and disorders in the organism. For example, when the immune system is overactive, unable to differentiate between self and foreign, or impaired. A good number of diseases and disorders are associated with a malfunctioning immune system. Some well-known ones include Hashimoto's thyroiditis, rheumatoid arthritis, diabetes mellitus type 1, systemic lupus erythematosus, multiple sclerosis, graft-versus-host disease (GVHD), and severe combined immunodeficiency such as HIV/AIDS. While there are numerous strategies, drugs, pharmaceutical compounds, agents and the likes that can be used to correct and/or mitigate the malfunctioning immune system, additions to the current repertoires of intervention would provide physicians with more and/or better options in the treatment and management of immune system related diseases and disorders.

In the treatment of any disease or disorder, specific delivery of therapeutics to the desired target sites in an organism is an important contributing factor to success of the treatment. This is especially true of biologic therapeutics. A biologic is a preparation, such as a drug, a vaccine, or an antitoxin, that is synthesized from living organisms or their products thereof, and is used as a diagnostic, preventive, or therapeutic agent. However, there are limited numbers of ways to delivery biologic therapeutics to target sites. Oral delivery is generally ineffective and difficult to achieve with biologics. Effective delivery systems are required if the therapeutic is to be delivered.

SUMMARY

Embodiments of the present technology are based on the discovery of a mutant strain of *Vibrio parahaemolyticus* that retained the ability to colonize the upper small intestine but does not cause the typical tissue pathology or diarrhea associated with an infection by *V. parahaemolyticus*. This mutant strain of *V. parahaemolyticus* has a mutant locus vpa1336 (encoding the vopZ gene of SEQ ID NO: 2, which encodes the VopZ protein of SEQ ID NO: 1, Genbank™ Accession No: NP_800846.1. The mutation in vopZ produces a mutated VopZ protein that has a small internal deletion from amino acids 38-62 (VopZΔ38-62). Moreover, this small internal deletion of VopZ amino acids 38-62 abolishes its capacity to block key innate immune pathways in a host animal cell, e.g., IL-8 production and NF-κB activation, indicating that the intact VopZ protein with amino acids 38-62 possess immunosuppressive activities.

Accordingly, such a mutant strain of *V. parahaemolyticus* can be used as (1) a live attenuated *Vibrio* strain bacteria for the vaccination against *V. parahaemolyticus* and (2) as a therapeutic delivery vehicle, especially for targeting therapeutics to the upper small intestines of an organism. In addition, the isolated VopZ protein or functional fragments thereof that comprise, at the minimum, at least the amino acids 38-62, are useful immunosuppressive biologics. In one embodiment, functional fragments of the isolated VopZ protein in the context of the technologies disclosed herein refer to non-full length isolated VopZ proteins that retain and possess immunosuppressive activities as described herein. In another embodiment, full length, isolated VopZ protein that contain at least one amino acid residue substitution but still retain and possess immunosuppressive activities are also contemplated.

Therefore, it is one object of the present disclosure to provide novel anti-inflammatory proteins derived from *V. parahaemolyticus*, and these proteins possess immunosuppressive activities.

It is also the objective of this disclosure to provide delivery means for biologic therapeutics, especially delivery means for directly injecting extraneous proteins into the upper small intestinal mucosa of an animal.

Furthermore, it is the objective of this disclosure to provide a live attenuated strain of *Vibrio* bacteria which retains the ability to colonize the intestine and also retains the ability to translocate extraneous protein into a cell, particularly a host animal cell, but the *Vibro* bacteria does not cause the typical tissue pathology or diarrhea that is known to be associated with *V. parahaemolyticus*. The attenuated strain of *Vibrio* described herein can be used as a vaccine for the treatment and/or reduction of the severity or symptoms caused by infection with *V. parahaemolyticus*, or for protection against *Vibrio* infections.

In one embodiment, the disclosure herein provides an isolated polypeptide comprising an amino acid sequence having a percent homology of at least 90% with an amino acid sequence of SEQ. ID. NO:1, wherein the polypeptide has immunosuppression activity.

In one embodiment, the isolated polypeptide suppresses interleukin-8 (IL-8) production in a cell. In another embodiment, the polypeptide inhibits nuclear factor kappa-light-chain-enhancer of activated B cells (NF-κB) activation in a cell. In a further embodiment, the polypeptide inhibits p65 nuclear translocation in a cell. In another embodiment, the polypeptide inhibits IκBα degradation in a cell. In some embodiments, the immunosuppression activity is manifested as the suppression of IL-8 production, the inhibition of NF-κB activation, the inhibition of p65 nuclear translocation and/or the inhibition of IκBα degradation in a cell.

In one embodiment, the immunosuppression activity is in response to the stimulation of the cell by the cytokines, such as tumor necrosis factor alpha (TNF-α) and/or interleukin-β (IL-1κ).

In one embodiment, the isolated polypeptide is fused to a second protein or portions thereof, wherein the second protein is not a polypeptide comprising an amino acid sequence having a percent homology of at least 90% with an amino acid sequence of SEQ. ID. NO:1, or a VopZ, full length, truncated or otherwise mutated.

In one embodiment, the isolated polypeptide described herein is fused or conjugated to a therapeutic molecule. In one embodiment, the fusion or conjugation is by a covalent linkage. In another embodiment, the fusion or conjugation is not by a covalent linkage but by a non-covalent linkage, such as Van der Waals interactions, ionic interactions and hydrogen bonds.

In one embodiment, this disclosure provides for an isolated chimeric or fusion polypeptide comprising a first portion (part) and a second portion (part), wherein the first portion is a polypeptide comprising an amino acid sequence having a percent homology of at least 90% with an amino acid sequence of SEQ. ID. NO: 1, or a VopZ, full length, truncated or otherwise mutated, wherein the first portion has immunosuppression activity, and a second portion is not a polypeptide of the first portion or fragment therefrom.

In one embodiment, the second portion comprises an amino acid sequence or a polymer that enhances the serum half-life of the first portion.

In one embodiment, the second portion is a therapeutic molecule.

In one embodiment, this disclosure provides for a vector comprising a nucleic acid encoding an isolated polypeptide or an isolated chimeric polypeptide described herein.

In another embodiment, this disclosure provides for a cell comprising a vector comprising a nucleic acid encoding an isolated polypeptide or an isolated chimeric polypeptide described herein. In another embodiment, this disclosure provides for a cell comprising a vector described herein.

In one embodiment, this disclosure provides for an immunosuppression composition comprising one or more of the each following: (1) an isolated polypeptide described herein; (2) an isolated chimeric polypeptide described herein; (3) a vector described herein; (4) a cell described herein, either alone or in combination, and a pharmaceutically acceptable carrier. In one embodiment, such an immunosuppression composition can be used for suppressing the immune system in a subject in need thereof. For example, the subject has an immune disease or disorder. Accordingly, in one embodiment, this disclosure provides an isolated polypeptide described herein, or an isolated chimeric polypeptide described herein, or a vector described herein, for use in suppressing the immune system in a subject in need thereof. In another embodiment, this disclosure provides for an immunosuppression composition described herein for use in suppressing the immune system in a subject in need thereof.

In another embodiment, this disclosure provides for the use of an isolated polypeptide described herein, or an isolated chimeric polypeptide described herein, or a vector described herein for the manufacture of medicament for suppressing the immune system in a subject in need thereof.

In one embodiment, this disclosure provides for a method of treating an immune system disease or disorder, comprising administering to a subject in need thereof a therapeutically effective amount of an isolated polypeptide described herein or an isolated chimeric polypeptide of described herein or an immunosuppression composition comprising one or more of the following: (1) an isolated polypeptide described herein; (2) an isolated chimeric polypeptide described herein; (3) a vector described herein; (4) a cell described herein, and a pharmaceutically acceptable carrier described herein.

In one embodiment, the subject has an autoimmune disease or disorder.

In one embodiment, the subject has a hyperactive immune system.

In one embodiment, the immune system disease or disorder is selected from the group consisting of an autoimmune disease, allergies and asthma.

In one embodiment, this disclosure provides for a method of suppressing a graft-versus-host disease in a subject comprising administering to the subject in need thereof a therapeutically-effective amount of an isolated polypeptide described herein or an isolated chimeric polypeptide of described herein or an immunosuppression composition comprising one or more of the following: (1) an isolated polypeptide described herein; (2) an isolated chimeric polypeptide described herein; (3) a vector described herein; (4) a cell described herein, either alone or in combination, and a pharmaceutically acceptable carrier described herein.

In one embodiment, the therapeutic methods described herein further comprising administrating in combination with at least one immunosuppressant therapy.

In one embodiment of the treatment methods described herein, the method further comprises selecting the subject in need of therapeutic intervention, for example, selecting a subject who has an autoimmune disease or disorder, a hyperactive immune system, some sort of allergies, or asthma. In one embodiment of the treatment methods described herein, the method further comprises selecting the subject who exhibit at least one symptom of an autoimmune disease or disorder, a hyperactive immune system, some sort of allergies, or asthma.

In one embodiment of suppressing a graft-versus-host disease described herein, the method further comprises selecting the subject in need of therapeutic intervention, for example, the subject shows signs of rejection of the transplanted tissue or organ. In one embodiment, the subject has previous history of rejecting a transplanted tissue or organ.

In one embodiment, this disclosure provides for an isolated live attenuated bacterium comprising a nucleic acid encoding a mutant VopZ protein. In some embodiments, the mutation encompasses at least one amino acid residue deletion, at least one amino acid residue addition, and/or at least one amino acid residue substitution. In one embodiment, the live attenuated bacterium retains the ability to colonize the upper small intestine of a subject host organism. In another embodiment, the live attenuated bacterium, after colonizing the intestine of a subject host organism, does not cause the typical tissue pathology or diarrhea known to be associated with *V. parahaemolyticus*.

In one embodiment, provided herein is a composition comprising isolated live attenuated bacteria comprising a nucleic acid encoding a mutant VopZ and a pharmaceutically acceptable carrier.

In one embodiment, such a composition comprising isolated live attenuated bacteria comprising a nucleic acid encoding a mutant VopZ protein and a pharmaceutically acceptable carrier is for use in the introduction of extraneous protein into an animal cell, e.g., a host animal cell.

Accordingly, in one embodiment, provided herein is an isolated live attenuated bacterium comprising a nucleic acid encoding a mutant VopZ protein for use in the introduction of extraneous protein into animal cells.

In another embodiment, provided herein is an isolated live attenuated bacterium comprising a nucleic acid encoding a mutant VopZ for use in the manufacture of a composition for the introduction of at least one extraneous protein into an animal cell.

In one embodiment, provided herein is a method of introducing an extraneous protein into an animal cell comprising contacting the animal cell with at least one live attenuated bacterium comprising a nucleic acid encoding a mutant VopZ protein described herein or a composition comprising isolated live attenuated bacteria comprising a nucleic acid encoding a mutant VopZ protein and a pharmaceutically acceptable carrier.

In one embodiment, provided herein is a method of introducing an extraneous protein into an animal cell comprising introducing a nucleic acid encoding the extraneous protein into a live attenuated bacterium comprising a nucleic acid encoding a mutant VopZ protein described herein and administering the resultant bacterium into the animal cell or administering to an animal. In one embodiment, the administering of the resultant bacterium into the animal cell comprises contacting the animal cell with the resultant bacterium. In one embodiment, the contacting can be in vivo, in vitro or ex vivo. In another embodiment, the animal cells are cultured in vitro.

In one embodiment, provided herein is a method of introducing an extraneous protein into an animal cell comprising providing a live attenuated bacterium comprising a nucleic acid encoding a mutant VopZ protein described herein and administering the live attenuated bacterium to an animal.

In one embodiment, provided herein is a delivery vehicle for introducing an extraneous protein into an animal cell, wherein the delivery vehicle is an isolated live attenuated bacterium comprising a nucleic acid encoding a mutant VopZ protein described herein.

In one embodiment, the isolated attenuated bacterium is of the *Vibro* genus.

In one embodiment, the isolated attenuated bacterium is *V. parahaemolyticus*. For example, *V. parahaemolyticus* RIMD2210633.

In one embodiment, the encoded mutated VopZ is a polypeptide lacking at least the amino acid residues 38-62 of SEQ. ID. NO:1 or a polypeptide lacking SEQ. ID. NO:5. In another embodiment, the encoded mutated VopZ is SEQ. ID. NO:3.

In one embodiment, the encoded mutated VopZ comprising an amino acid sequence having a percent homology of at least 90% with an amino acid sequence of SEQ. ID. NO:4. In another embodiment, the encoded mutated VopZ protein is translocated into the animal cell by the live attenuated bacterium.

In one embodiment, the animal cell is a mammalian cell. In one embodiment, the mammalian cells are human cells.

In one embodiment, the mammalian cells are cells of a mucosal epithelium. In one embodiment, the mucosal epithelium is the upper small intestinal mucosal epithelium of an animal, e.g., the duodenum mucosal epithelia.

In one embodiment, wherein the live attenuated bacteria or composition is to be administered to an animal, the animal is a mammal. In one embodiment, the mammal is a human. In one embodiment, the live attenuated bacteria or composition is to be administered orally to the animal.

In one embodiment, the live attenuated bacteria additionally comprising at least one nucleic acid encoding an extraneous protein to be introduced to the animal cell.

In one embodiment, the extraneous protein is an antigen. In another embodiment, the extraneous protein is a therapeutic agent.

In one embodiment, provided herein is a vaccine for reducing infection symptoms in an individual, the infection being caused by a *Vibro* bacteria, the vaccine comprising: (i) live attenuated *Vibro* bacteria comprising a nucleic acid encoding a mutant VopZ comprising an amino acid sequence having a percent homology of at least 90% with an amino acid sequence of SEQ. ID. NO:3; and (ii) a pharmaceutically acceptable excipient.

In one embodiment, provided herein is a vaccine for reducing in an individual infection symptoms, wherein the live attenuated *Vibro* bacteria is *Vibro parahaemolyticus*.

In one embodiment, provided herein is a method for reducing in an individual disease symptom caused by *Vibro* bacteria comprising administering to the individual live attenuated *Vibro* bacteria in a pharmaceutically acceptable excipient, in an immunologically effective dose.

Definitions

"Polypeptide" and "protein" are used interchangeably herein to refer to a polymer of amino acid residues. In one embodiment, the terms apply to amino acid polymers in which one or more amino acid residue is an artificial chemical mimetic of a corresponding naturally occurring amino acid, as well as to naturally occurring amino acid polymers and non-naturally occurring amino acid polymer. In another embodiment, "polypeptide" and "protein" further refer to amino acids joined to each other by peptide bonds or modified peptide bonds, i.e., peptide isosteres, and can contain modified amino acids other than the 20 gene-encoded amino acids. In another embodiment, the terms also include modifications either by natural processes such as glycosylation and other post-translational modifications, or by chemical modification techniques which are well known in the art.

The term "isolated" refers to material, such as a nucleic acid or a protein, which is substantially or essentially free from components which normally accompany or interact with the material as found in its naturally occurring environment.

As used herein, the term "fusion protein" or "fusion polypeptide" refers to a protein created either by joining two nucleic acid sequences, each of which encodes a protein, or by the joining of two proteins or peptides together by chemical linkage known in the art. As used herein, the term "fusion protein" refers to a recombinant protein of two or more proteins which are joined by a peptide bond. Fusion proteins can be produced, for example, by a nucleic acid sequence encoding one protein joined to a nucleic acid encoding another protein such that they constitute a single open-reading frame that can be translated into a single polypeptide harboring each of the intended proteins or protein domains. In a fusion protein, the two proteins that will be joined together with a linker or spacer peptide added between the two proteins. This linker or spacer peptide often contain protease cleavage site to facilitate the separation of the two proteins after expression and purification. The making of fusion protein as a technique is commonly used for the identification and purification of proteins through the fusion of a GST protein, FLAG peptide or a hexa-his peptide (SEQ ID NO: 6).

A "chimeric polypeptide" is a fusion polypeptide that is made of two different protein, e.g., a VopZ (aa 1-50)-HIV gp120 is a chimeric polypeptide of the VopZ and HIV gp120 proteins, made of the VopZ amino terminal 1-50 residues fused to the HIV gp120; a VopZΔ38-62-HIV gp120 is also a chimeric polypeptide of the VopZ and HIV gp120 proteins, made of the VopZ full length minus 38-62 residues fused to the HIV gp120; and a VopL (aa 1-50)-antiTNF-α antibody is a chimeric polypeptide of the VopL and an antiTNF-α antibody, made of the VopL amino terminal 1-50 residues fused to the antiTNF-α antibody. A "chimeric polypeptide" is a protein that does not occur naturally.

As used herein, the term "nucleic acid" refers to DNA or RNA. The term encompasses sequences that include any of the known base analogs of DNA and RNA.

The term "vector", as used herein, refers to a nucleic acid construct comprising any one of the sequences of SEQ. ID. NOS: 2 and 4, and those of VopT: NP_800837.1 (SEQ ID NO: 7); VopA: NP_800856.1 (SEQ ID NO: 8); VopL: NP_800881.1 (SEQ ID NO: 9); VopV: NP_800867.1 (SEQ ID NO: 10); and VopC: NP_800831.1 (SEQ ID NO: 11), wherein the nucleic acid construct is designed for delivery to a host cell, transfer between different host cells, or for the expression of Vop proteins or extraneous proteins, in host cells. In one embodiment, the vector is not a naturally occurring nucleic acid construct, that is, it is man-made or artificially design and made by man. In some embodiments, the vector is a bacteria, yeast, fungal, viral or non-viral plasmid or nucleic acid constructs. In one embodiment, a vector is a viral or a non-viral vector.

As used herein, "host cells" are cells for carrying, holding, maintaining, storing, and replication of a vector and/or expression of an encoded nucleic acid in the vector, and are not those cells which naturally carry, hold, maintain, store, replicate the vector and/or express the encoded nucleic acid in the vector. For example, when an insect vector is placed in bacteria, the bacteria are host cells for that insect vector because the bacteria is not the natural cell for that insect vector. Non-limiting examples of host cells include bacteria, virus, mammalian, animal, yeast, insects and plant cells. Non-limiting examples of mammalian host cells include human, mouse, monkey, rat, and hamster cells.

As used herein, the term "viral vector" refers to a nucleic acid vector construct that includes at least one element of viral origin and includes elements sufficient for or permissive of packaging into a viral vector particle. A viral vector can contain the coding sequence for a desired and selected protein in place of non-essential viral genes. The vector and/or particle can be utilized for the purpose of transferring DNA, RNA or other nucleic acids into cells either in vitro or in vivo. Numerous forms of viral vectors are known in the art. In one embodiment, the "viral vector" is a gene therapy vector for the transfer and the expression of a nucleic acid into a cell or organism.

A "host organism" as used herein is an organism for introducing, carrying, holding, maintaining, storing, and/or replication of a vector, and/or expression of an encoded nucleic acid in the vector. In one embodiment, a "host organism" is an animal, such as a mammal. Examples of mammals include but not limited to human, mouse, monkey, rat, and hamster.

By a "full length" Vop polypeptide means the amino acid sequence as determined by the coding sequences of SEQ. ID. NOS: 2 and 4, and those of VopT: NP_800837.1 (SEQ ID NO: 7); VopA: NP_800856.1 (SEQ ID NO: 8); VopL: NP_800881.1 (SEQ ID NO: 9); VopV: NP_800867.1 (SEQ ID NO: 10); and VopC: NP_800831.1 (SEQ ID NO: 11). In some embodiments, the "full length" Vop polypeptide may have conservative amino acid substitution.

By "mutations" in proteins means amino acid substitutions, amino acid additions and/or amino acid deletions. The proteins can have a combination of each of three different types of mutations. For example, the protein has amino acid substitutions and amino acid deletions, or amino acid deletions and additions. In one embodiment, the amino acid substitution is conservative or non-conservative. Methods of creating of these mutations are known in the art, such as by PCR, oligonucleotide-directed mutagenesis, site-specific mutagenesis and any combination thereof.

As used herein, the term "amino acid" is intended to include not only the L-, D- and non-chiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like.

As used herein, the term "inhibit" or "inhibition" in the context of interleukin-8 (IL-8) production, nuclear factor kappa-light-chain-enhancer of activated B cells (NF-κB) activation, p65 nuclear translocation, IκBα degradation, means a reduction or prevention of IL-8 production, NF-κB activation of B cells, p65 nuclear translocation, and IκBα degradation respectively in a cell as described in the assays found in the Example section. In one embodiment, "inhibit" or "inhibition" in the context of treating or suppressing the immune system or a graft-versus-host disease means a reduction or prevention of at least one symptom known to be exhibited in an immune system disease or disorder, or a graft-versus-host disease. Such symptoms are known to a clinician, and are also documented and readily available in the Merck Medical Manual.

In some embodiments, inhibition includes slowing the IL-8 production, NF-κB activation, p65 nuclear translocation and IκBα degradation respectively. The reduction of production, activation, translocation and degradation respectively can be by about 5%, about 10%, about 20%, about 30%, about 40%, about 50%, about 60%, about 70%, about 80%, about 90%, about 100%, about 125%, about 150% or more compared to a control condition that is in the absence of an isolated polypeptide comprising an amino acid sequence having a percent homology of at least 90% with an amino acid sequence of SEQ. ID. NO:1. In other embodiments, the reduction of at least one symptom known to be exhibited in an immune system disease or disorder, or a graft-versus-host disease can be by about 5%, about 10%, about 20%, about 30%, about 40%, about 50%, about 60%, about 70%, about 80%, about 90%, about 100%, about 125%, about 150% or more compared to the absence of a therapeutic intervention described. In another embodiment, inhibition also means a reduction in the rate of production, activation, translocation and degradation respectively by at least 10%, at least 20%, at least 30%, at least 40%, at least 50%, at least 60%, at least 70%, at least 80%, at least 90%, at least 100% or more compared to a control condition that is in the absence of an isolated polypeptide comprising an amino acid sequence having a percent homology of at least 90% with an amino acid sequence of SEQ. ID. NO:1. In another embodiment, inhibition also means a reduction in the rate of developing at least one symptom by at least 10%, at least 20%, at least 30%, at least 40%, at least 50%, at least 60%, at least 70%, at least 80%, at least 90%, at least 100% or more compared to a control condition that is in the absence of a therapeutic intervention described.

In one embodiment, the term "suppress" in the context of IL-8 production, the immune system or a graft-versus-host disease means the inhibition of IL-8 production, the immune system or the graft-versus-host disease respectively.

As used herein, the term "therapeutically effective amount" refers to the amount that is safe and sufficient to treating an immune system disease or disorder, or sufficient to suppress a graft-versus-host disease in transplant patients. In some embodiments, the amount can also cure or cause the immune system disease or disorder, or graft-versus-host disease to go into remission, slow the course of the disease/disorder progression, slow or inhibit the rate of developing at least one symptom known to be exhibited in an immune system disease or disorder, or a graft-versus-host disease.

In one embodiment, the term "treat" or "treatment" refers to therapeutic treatment of the conditions described herein, ie., an immune system disease or disorder, or graft-versus-host disease, wherein the object is to slow down, and/or halt the development the disease/disorder progression, slow or inhibit the rate of developing at least one symptom known to be exhibited in an immune system disease or disorder, or a graft-versus-host disease.

In another embodiment, the term "treat" or "treatment" refers to prophylactic or preventative measures, wherein the object is to prevent an immune system disease or disorder, or graft-versus-host disease, such as prevent the development the disease/disorder progression, slow or inhibit the rate of developing at least one symptom known to be exhibited in an immune system disease or disorder, or a graft-versus-host disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. In another embodiment, "treatment" can also mean prolonging survival as compared to expected survival if not receiving treatment.

As used herein, a "hyperactive immune system" refers to the state of the immune system in an organism such that the immune system is attacking normal tissues in the organism as if they were foreign organisms. In one embodiment, a "hyperactive immune system" is one that has lost the ability to differentiate normal from foreign tissues in the affected organism.

As used herein, a "subject" refers to a mammal, preferably a human. The term "individual", "subject", and "patient" are used interchangeably.

As used herein, a "live attenuated" bacterium means a live bacterium or functional bacterium whose disease-producing ability, e.g., diarrhea, has been weakened but whose immunogenic properties have not.

As used herein, the term "introduce" in the context of an extraneous protein means placing the extraneous protein inside of a recipient cell. "Introduction" can be by translocation by a bacterium possessing a T3SS2 translocation system, or by infection by a viral vector.

As used herein, in one embodiment, an "extraneous" protein is a protein that is not naturally occurring in a particular cell that the protein is introduced into. For example, human cells do not naturally have the HIV gp120 protein. When the HIV gp120 protein is introduced into a human cell, the HIV gp120 protein is an "extraneous" protein with respect to the recipient cell, the human cell.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

As used herein, the terms "administering," refers to the placement of a polypeptide or a composition described into a subject by a method or route which results in at least partial localization of the polypeptide or a composition at a desired site. The polypeptide or composition described can be administered by any appropriate route which results in an effective treatment in the subject.

As used herein, the term "comprising" or "comprises" means that the respective component(s) in the claimed technology, ie., polypeptides, compositions, and methods, are essential to the technology described herein, yet open to the inclusion of unspecified elements, whether essential or not. The use of "comprising" indicates inclusion rather than limitation.

As used herein the term "consisting essentially of" means that those elements are required for a given embodiment in the claimed technology described herein. The term permits the presence of elements that do not materially affect the basic and novel or functional characteristic(s) of that embodiment of the technology described herein.

The term "consisting of" means that the respective components in the claimed technology as described herein, and are exclusive of any element not recited in that description of the embodiment.

BRIEF DESCRIPTION OF THE DRAWINGS

FIGS. 1A-1B shows the process of identification of T3SS2 secreted polypeptides.

FIG. 1A shows the schematic depiction of the T3SS2 region from *V. parahaemolyticus* RIMD2210633, including most genes from vpa1321 to vpa1370. Genes encoding effectors are 1321, 1327, 1336, 1346, 1357, and 1370; genes encoding structural components are 1338/9, 1341/2/3, 1345, 1349/50, 1354/5, 1361/2 and 1367. The transcriptional regulator vtrB (vpa1348) is before 1349.

FIG. 1B shows the identity of the spots identified from DIGE and mass spectrometry. Protein Spots 1, 2-9, 10, 11, 12, 20, 21, 22, 24, 25, 28 and 29 are proteins encoded in T3SS2; protein spots 13-19, 23, 25, 27 and 30 are proteins encoded outside of T3SS2; effector proteins are VopV, VopL, VopZ, VopT, VopA, and VopC. Asterisk indicates previously unidentified T3SS2-secreted proteins.

FIG. 2A shows that the translocon protein VopD2 was detected in cell pellets and supernatants from the indicated strains by immunoblotting with anti-VopD2 antisera. All strains overexpressed vtrB.

FIG. 2B shows the cAMP levels in Caco-2 cells monitored one hour after infection with the indicated strains. Either vscN1 (open bars) or vscN1 vscN2 (gray bars) *V. parahaemolyticus* strains expressing Cya, VopZ-Cya or VopV-Cya were used. Mean values and standard deviation, based on 3 replicate assays, are shown. Statistically significant differences in effector translocation by the vscN1 vscN2 strain (* p<0.001; **, p<0.0001) are in comparison to translocation of the same effector by the vscN1 strain.

FIG. 3A shows the IL-8 release by HEK293 cells as monitored following infection with the indicated strains of *V. parahaemolyticus*, using cells either treated (grey bars) or not treated (white bars) with TNFα. IL-8 levels in supernatants were measured via ELISA; mean values (n=2) and standard deviation are shown. * indicates statistical difference (P<0.05) when compared to vscN1-infected cells without TNF treatment; ** indicates statistical difference (P<0.05) when compared to vscN1-infected cells with TNFα

FIG. 3B shows the IL-8 release by HeLa cells as monitored following infection with the indicated strains of *V. parahaemolyticus*, using cells either treated (grey bars) or not treated (white bars) with IL-1β. For A and B, IL-8 levels in supernatants were measured via ELISA; mean values (n=2) and standard deviation are shown. * indicates statistical difference (P<0.05) when compared to vscN1-infected cells without TNF treatment; ** indicates statistical difference (P<0.05) when compared to vscN1-infected cells with IL-1β treatment.

FIGS. 4A-4C show that VopZ inhibits TNFα-stimulated and *V. parahaemolyticus*-induced NF-κB pathway activation.

FIG. 4A shows the GFP mean fluorescence intensity (M.F.I.) in HEK293 NF-κB GFP reporter cells infected for 90 minutes, and then stimulated by TNFα (1 ng/ml) for 6 hours.

FIG. 4B shows representative FACS overlay plots of NF-κB GFP in HEK293 NF-κB GFP reporter cells infected for 90 minutes, and then stimulated by TNFα (1 ng/ml) for 6 hours.

FIG. 4C shows the NF-κB activity in HEK293 cells infected for 90 minutes and analyzed 15 hours later, without TNFα stimulation. Duplicate samples from three independent experiments were used to obtain MFI and standard deviation data. Student's 2stailed paired T-Test P-values are denoted. All samples bracketed were found to differ significantly from the vscN1 control strain.

FIG. 5A is a representative Western blot of three independent experiments where HEK293 cells were infected with *V. parahaemolyticus* strains for 90 minutes, then stimulated by TNFα (1 ng/ml) for the indicated times. Western blot of tubulin served used loading controls. The blot shows reduced degradation of IkBα upon TNFα stimulation when VopZ is present.

FIG. 5B is another representative Western blot showing that VopZ inhibits IkBα turnover in HEK293 cells were infected with *V. parahaemolyticus* strains and stimulated by TNFα (1 ng/ml) as in FIG. 5A. Western blot of p65 served used loading controls.

FIG. 5C is a representative Western blot of HEK293 cells infected with the indicated strains for 90 min., and then stimulated by LMP1 expression for 12 hours to induce non-canonical NF-KB signaling. Non-canonical NF-KB pathway activation induces cleavage of p100 into p52. The Western blot show no changes in the p52 produced in the presence or absence of VopZ.

FIGS. 6A and 6B are representatives Western blots obtained from three independent experiments wherein HEK293 cells were infected with *V. parahaemolyticus* strains for 90 minutes, and then stimulated by TNFα (1 ng/ml). The Western blots show activation of p38, JNK and ERK by way of phosphorylation upon stimulation by TNFα.

FIG. 6C shows a schematic of signaling pathways leading to activation of MAPKs and canonical and non-canonical NF-KB and possible site of action of VopZ. CM: cell membrane; NM: nuclear membrane.

FIG. 7A shows a graphical representation of bacterial colonization (cfu/g intestinal tissue) in the intestine of infant rabbits infected with the indicated strains of *V. parahaemolyticus* at ~38 hr post infection. Lines show geometric means.

FIG. 7B shows a graphical representation of intestinal fluid accumulation ratios for infant rabbits infected with the indicated strains of *V. parahaemolyticus* at ~38 hr post infection. Means and SEM, based on at least 9 rabbits. Data for the vscN1 and vscN2 strains was previously published (Ritchie et al., 2012).

FIG. 7C shows hematoxylin and eosin stained histology tissue from the distal small intestines of infected rabbits. Arrows indicate bacterial microcolonies.

FIG. 7D shows a graphical representation of heterophil infiltration in tissue from distal intestines of infected infant rabbits as scored as described in Ritchie et al., 2012; median values are indicated. Statistical significance was assessed with one way ANOVA and Bonferroni's post tests; * (p<0.05),  (p<0.01), * (P<0.001), or as indicated on the graph.

FIG. 7E shows a graphical representation of tissue sloughing in tissue from distal intestines of infected infant rabbits as scored as described in Ritchie et al., 2012; median values are indicated. Statistical significance was assessed with one way ANOVA and Bonferroni's post tests; * (p<0.05),  (p<0.01), * (P<0.001), or as indicated on the graph.

FIG. 8A shows a graphical representation of bacterial colonization of the distal small intestine (CFU/gm) in infant rabbits ~38 hrs after inoculation of wild type (wt) and mutant *V. parahaemolyticus*. The horizontal bars indicate geometric means.

FIG. 8B shows a graphical representation of mean fluid accumulation ratios in infant rabbits ~38 hrs after inoculation of wild type (wt) and mutant *V. parahaemolyticus*. Data for the wt and vscN2 strains was previously published (Ritchie et al., 2012). The error bars represent SEM. Statistical significance was determined from one way ANOVA followed by Bonferroni's post test.

DETAILED DESCRIPTION

Figure 2A:
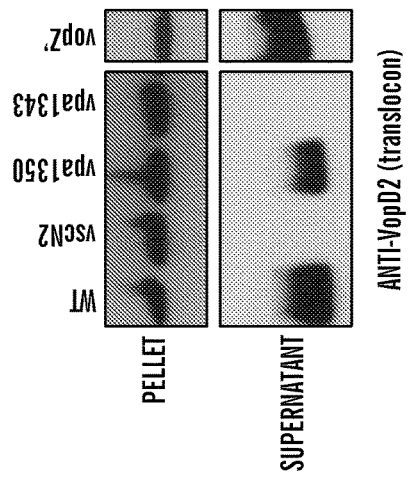
FIGS. 2A-2B shown that VopZ (Vpa1336) is translocated and is not required for secretion/translocation of other T3SS2 substrates.
Figure 2B:
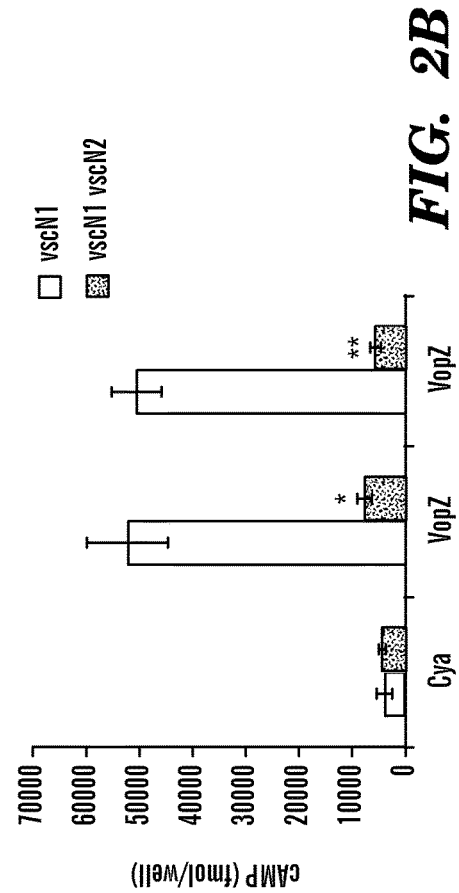

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present technology was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), which are all herein incorporated by reference in their entireties.

It should be understood that this present technology is not limited to the particular methodology, protocols, and reagents, etc., described herein and as such may vary. The terminology used herein is for the purpose of describing particular embodiments only, and is not intended to limit the scope of the present technology, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present technology. These publications are provided solely for their disclosure prior to the filing date of the present application. Nothing in this regard should be construed as an admission that the inventors are not entitled to antedate such disclosure by virtue of prior technology or for any other reason. All statements as to the date or representation as to the contents of these documents is based on the information available to the applicants and does not constitute any admission as to the correctness of the dates or contents of these documents.

Embodiments of the present technology are based on the discovery that a *Vibrio parahaemolyticus* bacteria that has a locus vpa1336 (renamed vopZ), a gene that is essential for the pathogen to colonize the intestine and cause pathology and diarrhea. In tissue culture cells, the encoded protein VopZ blocks the activation of all three MAPK and NFKB signaling pathways which are involved in the activation of an immune system in an animal cell. A small internal deletion of VopZ comprising amino acids 38-62 abolishes its capacity to block these key innate immune pathways. However, a *V. parahaemolyticus* strain producing the mutant VopZ 438-62 protein remains able to colonize the intestine but does not cause pathology or diarrhea. Based on these observations, VopZ and derivatives of VopZ could be used as anti-flammatory agents. In addition, *V. parahaemolyticus* and similar strains of bacteria that express mutant VopZ and have an intact type 3 secretion systems (T3SS), which directly inject proteins into intestinal epithelial cells, would make useful delivery vehicles to the intestinal epithelium where these bacteria tend to inhabit and target. For example, as a delivery vehicles to deliver other heterologous antigens to the intestinal mucosa. Moreover, *V. parahaemolyticus* and similar strains of bacteria that containing mutations in vopZ, for example, a *V. parahaemolyticus* that express as the mutant protein VopZ 438-62, constitute the basis for a live attenuated vaccine against this seafood-borne pathogen that is prevalent world-wide.

Accordingly, in one embodiment, provided herein is an isolated polypeptide comprising an amino acid sequence having a percent homology of at least 90% with an amino acid sequence of SEQ. ID. NO:1, wherein the polypeptide has immunosuppression activity. In another embodiment, the isolated polypeptide consists essentially of an amino acid sequence having a percent homology of at least 90% with an amino acid sequence of SEQ. ID. NO:1, wherein the polypeptide has immunosuppression activity. In another embodiment, the isolated polypeptide consists of an amino acid sequence having a percent homology of at least 90% with an amino acid sequence of SEQ. ID. NO:1, wherein the polypeptide has immunosuppression activity. In another embodiment, the isolated polypeptide consists of an amino acid sequence of SEQ. ID. NO:1, wherein the polypeptide has immunosuppression activity.

In some embodiments, the isolated polypeptide comprising an amino acid sequence has a percent homology of at least 91%, at least 92%, at least 93%, at least 94%, at least 95%, at least 96%, at least 97%, at least 98%, at least 99%, or 100% with an amino acid sequence of SEQ. ID. NO:1.

In one embodiment, the isolated polypeptide comprises an amino acid sequence having at the minimum the amino acid sequence LNQMSKVESRDIDLSFVLDQEEEDE (SEQ. ID. NO: 5).

In one embodiment, the isolated polypeptide comprises an amino acid sequence having a percent homology of at least 90% with an amino acid sequence of a VopZ protein. In another embodiment, the isolated polypeptide comprises a VopZ protein. In another embodiment, the isolated polypeptide is a VopZ protein. In one embodiment, the VopZ is encoded by a vopZ gene. In one embodiment, the vopZ gene ID is Genbank™ Accession No: NP_800846.1. In one embodiment, the VopZ is encoded by NP_800846.1 or SEQ. ID. NO:2.

In one embodiment, the VopZ is a full length polypeptide comprising 220 amino acid residues and is approximately 20 kilodaltons (kDa) as estimated by denaturing protein gel electrophoresis.

In another embodiment, the isolated polypeptide comprising a VopZ has at the minimum the amino acid sequence LNQMSKVESRDIDLSFVLDQEEEDE (SEQ. ID. NO: 5).

In another embodiment, the isolated polypeptide described herein has at least one mutation, such as one or more amino acid residue deletion, addition or substitution, but such a mutated polypeptide retains at least one immunosuppression activity as described herein. In some embodiments, the isolated polypeptide has a combination of more than one type of mutations, the types of mutations comprising amino acid residue deletion, addition or substitution. For examples, the isolated polypeptide has at least one amino acid residue deletion and at least one amino acid residue addition; at least one amino acid residue deletion and at least one amino acid residue substitution; at least one amino acid residue substitution and at least one amino acid residue addition; or at least one amino acid residue deletion, at least one amino acid residue substitution and at least one amino acid residue addition. Also contemplated is an isolated polypeptide having more than one amino acid residue deletions alone, more than one amino acid residue additions alone or more than one amino acid residue substitutions alone, and combinations thereof. In some embodiments, the amino acid substitution can be conservative substitution or non-conservative substitution.

In some embodiments, mutations contemplated can be in the form of truncation at the amino terminus or the carboxyl terminus or at both ends of the full-length polypeptide. The polypeptide can also have an internal deletion of the amino acids. In some embodiments, the deletion is less than 50 amino acid deletion, less than 40 amino acid deletion, less than 30 amino acid deletion, less than 25 amino acid deletion, less than 20 amino acid deletion, less than 15 amino acid deletion, less than 10 amino acid deletion, less than 5 amino acid deletion, less than 4 amino acid deletion, less than 3 amino acid deletion, or less than 2 amino acid deletion, relative to the parent full length protein.

In other embodiments, mutations contemplated can be in the form of amino acid additions at the amino terminus or the carboxyl terminus or at both ends of the full-length polypeptide. The polypeptide can also have amino acid additions to the internal of the polypeptide. In some embodiments, the addition is less than 50 amino acid addition, less than 40 amino acid addition, less than 30 amino acid addition, less than 25 amino acid addition, less than 20 amino acid addition, less than 15 amino acid addition, less than 10 amino acid addition, less than 5 amino acid addition, less than 4 amino acid addition, less than 3 amino acid addition, or less than 2 amino acid addition, relative to the parent full length protein.

In one embodiment, the VopZ full-length protein amino acid sequence is

```
                                              (SEQ. ID. NO: 1)
MSNINNSVSLFIRDTVDGEFDKATSKQSNTDDDFSKILNQMSKVESRDI

DLSFVLDQEEEDEDEECDTELLQNTRSIESVKERGLLNFLFRHPTKNVY

IRPTNKKRDIEQNEIVLTLQYQQSNYNFKWRKIEIEGVKVRLEKNTPGL

RVFNSLHFDNNNFVSIIDEKIYSKNNEFAYLSSDFKKYINVENYTRSIA

IPLASTMSFDLSVNYFNQINTLNKYRVLYKKKYYIFEFENGKLVNFMRG

YNDGY.
```

In one embodiment, the isolated polypeptide is derived from a *Vibrio* bacteria species. For example, from a *V. parahaemolyticus* strain. In one embodiment, the isolated polypeptide is a polypeptide encoded by a bacterial derived gene or nucleic acid. In one embodiment, the isolated polypeptide is not a polypeptide encoded by a bacterial derived gene or nucleic acid, e.g., a viral gene, an animal gene, a mammal gene or a human gene. In one embodiment, the bacteria gene or nucleic acid has at least one mutation that results in one or more amino acid residue deletion, addition or substitution upon transcription and translation of the gene or nucleic acid.

In one embodiment, the isolated polypeptide described herein is encoded by a nucleic acid sequence having a percent homology of at least 90% with a nucleic acid sequence of SEQ. ID. NO:2.

The vopZ gene ID is Genbank™ Accession No: NP_800846.1,

```
                                              (SEQ. ID. NO: 2)
ATGAGCAACATTAATAATTCTGTATCGCTATTCATTCGAGATACGGTAGA

CGGTGAATTTGATAAAGCAACCTCTAAACAATCTAATACTGATGATGACT

TCTCTAAAATTCTGAATCAAATGAGTAAAGTCGAGAGCAGAGACATTGAT

CTTAGCTTTGTACTTGATCAGGAAGAAGAGGATGAGGATGAGGAGTGTGA

TACAGAATTATTGCAGAATACACGAAGTATTGAATCGGTTAAAGAAAGGG

GTTTATTAAATTTTTTATTCCGTCATCCTACGAAAAATGTCTATATCAGA

CCTACCAATAAAAAACGCGATATTGAGCAAAACGAGATTGTTCTGACGCT

GCAGTATCAGCAATCGAATTATAATTTTAAGTGGAGAAAGATTGAGATAG

AGGGGGTGAAAGTTAGATTAGAAAAAAATACTCCTGGACTTAGAGTATTC

AATTCTCTTCACTTTGATAATAATAATTTTGTTAGCATAATAGATGAAAA

AATATATTCAAAAAATAATGAATTCGCGTATTTGAGTAGTGATTTTAAAA

AATATATAAACGTAGAGAACTATACAAGAAGTATAGCTATCCCCCTAGCT

AGTACGATGAGTTTTGATCTTTCTGTAAATTATTTTAATCAAATCAATAC

CTTGAATAAGTACCGAGTGTTATATAAGAAAAAATATTATATATTTGAAT

TTGAAAATGGAAAATTAGTTAATTTTATGCGAGGTTATAATGACGGTTAT

TGA.
```

In one embodiment, the SEQ. ID. NO: 2 is the nucleic acid coding sequence of the full-length VopZ of *V. parahaemolyticus*.

In one embodiment, the isolated polypeptide described herein suppresses interleukin-8 (IL-8) production in a cell. In another embodiment, the polypeptide inhibits nuclear factor kappa-light-chain-enhancer of activated B cells (NF-κB) activation in a cell. In a further embodiment, the polypeptide inhibits p65 nuclear translocation in a cell. In another embodiment, the polypeptide inhibits IκBα degradation in a cell. In some embodiments, the immunosuppression activity is manifested as the suppression of IL-8 production, the inhibition of NF-κB activation, the inhibition of p65 nuclear translocation and/or the inhibition of IκBα degradation in a cell as described herein. Methods of assaying cellular immunosuppression activities of a protein, agent, compound or drug etc. are known in the art. For example, such assay methods are described in Juliet V. Spencer et al., 2002, J. Virol., 76: 1285-1292; Kenneth R. et al. 1990, Clin. Chem., 36: 225-229; D. Weltin et al., 1995, Intl. J. Immunopharmacology, 17: 265-271; and Anne Gouby et al., 1983, Immunobiology, 164: 343-348. In some embodiments, the cellular immunosuppression activities of the isolated polypeptide comprising an amino acid sequence having a percent homology of at least 90% with an amino acid sequence of SEQ. ID. NO, or an isolated polypeptide encoded by a nucleic acid sequence having a percent homology of at least 90% with SEQ. ID. NO:2 can be assayed with the method described in the Example section.

In one embodiment, the immunosuppression activity is in response to the stimulation of the cell by the cytokines, such as tumor necrosis factor alpha (TNF-α) and/or interleukin-1β (IL-1β).

In one embodiment, the isolated polypeptide described herein is fused to a second protein or portions thereof, wherein the second protein is not a polypeptide comprising an amino acid sequence having a percent homology of at least 90% with an amino acid sequence of SEQ. ID. NO:1, or is not a VopZ full length protein, or is not a VopZ that is truncated, or otherwise mutated, wherein the mutations are selected from amino acid residue deletions, additions or substitutions. For examples, the second protein or portion thereof comprises transferrin, Fc portion of IgG, and albumin. In some embodiments, the second portion is for the purpose of improving serum half-life in vivo of the isolated polypeptide described herein. Other examples of the second protein or portion thereof include to the leader ~105 amino acid residues of thioredoxin or the six-histidine tag for the purpose facilitating recombinant protein expression and purification.

In one embodiment, the isolated polypeptide described herein is fused or conjugated to a therapeutic molecule. In one embodiment, the fusion or conjugation is by a covalent linkage. In another embodiment, the fusion or conjugation is not by a covalent linkage.

In one embodiment, this disclosure provides for an isolated chimeric or fusion polypeptide comprising a first portion (part) and a second portion (part), wherein the first portion is a polypeptide of comprising an amino acid sequence having a percent homology of at least 90% with an amino acid sequence of SEQ. ID. NO:1, or a VopZ full length polypeptide, or a VopZ truncated or otherwise mutated, wherein the first portion has immunosuppression activity, and wherein the second portion is not a polypeptide of the first portion or fragment therefrom. In one embodiment, the first portion comprises at the minimum the amino acid sequence LNQMSKVESRDIDLSFVLDQEEEDE (SEQ. ID. NO: 5). For examples, the second portion of the chimeric or fusion polypeptide can be transferrin, Fc portion of IgG, albumin, and PEG, for the purpose of improving serum half-life in vivo. Other examples of the second portion include to thioredoxin and six histidine tag (SEQ ID NO: 6) for facilitating recombinant protein expression and purification. Fusion polypeptides comprising such second portion s are known in the art.

In one embodiment, the second portion comprises an amino acid sequence or a polymer. In one embodiment, the second portion functions to enhance the serum half-life of the first portion. In another embodiment, the second portion functions to improve the pharmacokinetics of the first portion in the subject being treated with the isolated chimeric or fusion polypeptide for therapeutic purposes as described herein. Examples of the second portion are serum transferrin or portions thereof, albumin, transthyretin, Fc of IgG (See G. M. Subramanian, (2007), Nature Biotechnology 25, 1411-141), and polymers such as polyethylene glycol (PEG) for the purpose of enhancing the serum half-life. Other suitable polymers include, for example, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. A polymer may or may not have its own biological activity. The polymers can be covalently or non-covalently conjugated to the first portion.

In one embodiment, the second portion is a therapeutic molecule. A variety of therapeutic molecules are contemplated. For example, an anti-angiogenic therapeutic molecule, such as angiostatin and endostatin, a toxin such as methotrexate (MTX) or a radiotherapy molecule such as Boron-10, neutron-activated radiotherapic molecule, indium-111 and iodine-123. In another embodiment, the therapeutic molecule is a monoclonal antibody. For example, the monoclonal antibody is an inhibiting antibody of an immune reaction.

Methods for conjugating polypeptides to another entity, e.g., another protein, polymer, therapeutic molecule etc. are known in the art. For example, methods for conjugating for the purpose of increasing serum half-life and for radiotherapy described in U.S. Pat. Nos. 5,180,816, 6,423,685, 6,884,780, and 7,022,673, which are hereby incorporated by reference in their entirety. Additional methods of conjugating radioisotope, toxin, prodrug, and drug to the first portion or the isolated polypeptide described herein are fully described in U.S. Pat. No. 5,851,527 and is incorporated hereby reference in its entirety.

In one embodiment, the isolated polypeptide, fusion polypeptide or chimeric polypeptide include modifications within the sequence, such as, modification by terminal-NH$_2$ acylation, e.g., acetylation, or thioglycolic acid amidation, by terminal-carboxylamidation, e.g., with ammonia, methylamine, and the like terminal modifications. Terminal modifications of polypeptides are useful, and are known in the art; they serve to reduce susceptibility to proteinase digestion, and therefore serve to prolong half-life of the polypeptides in solutions, particularly biological fluids where proteases may be present.

In one embodiment, this disclosure provides for a nucleic acid sequence encoding an isolated polypeptide or an isolated fusion or chimeric polypeptide described herein. In one embodiment, the encoded isolated polypeptide or an isolated fusion or chimeric polypeptide described herein has a percent homology of at least 90% with an amino acid sequence of SEQ. ID. NO:1. In one embodiment, the nucleic acid sequence encoding an isolated polypeptide or an isolated fusion or chimeric polypeptide described herein comprises at the very minimum a nucleic acid sequence encoding the amino acid sequence SEQ. ID. NO: 5.

In another embodiment, this disclosure provides for a nucleic acid sequence encoding an isolated polypeptide or an isolated fusion or chimeric polypeptide described herein having a percent homology of at least 90% with an amino acid sequence of SEQ. ID. NO:1.

In one embodiment, this nucleic acid encoding an isolated polypeptide or an isolated fusion or chimeric polypeptide having a percent homology of at least 90% with an amino acid sequence of SEQ. ID. NO:1 does not comprise a nucleic acid sequence encoding the amino acid sequence SEQ. ID. NO: 5.

In one embodiment, this disclosure provides for a vector comprising a nucleic acid encoding an isolated polypeptide or an isolated fusion or chimeric polypeptide described herein. In some embodiments, the vector can be an expression vector, a bacterial plasmid, and/or viral vector, e.g., a gene therapy virus or a phage plasmid. The expression vector can be for the expression and purification of recombinant polypeptide or fusion or chimeric polypeptide described herein that are produced from a eukaryotic protein expression system using host cells selected from the group consisting of mammal, insects, yeast, or plant cells.

In one embodiment, this disclosure provides for a cell comprising a vector described herein. In another embodiment, this disclosure provides for a cell comprising a vector comprising a nucleic acid encoding an isolated polypeptide or an isolated chimeric polypeptide described herein. In another embodiment, this disclosure provides for a cell comprising a nucleic acid sequence encoding an isolated polypeptide or an isolated chimeric polypeptide described herein. In one embodiment, the encoded isolated polypeptide or an isolated fusion or chimeric polypeptide described herein has a percent homology of at least 90% with an amino acid sequence of SEQ. ID. NO:1. In one embodiment, the nucleic acid sequence encoding an isolated polypeptide or an isolated fusion or chimeric polypeptide described herein comprises at the very minimum a nucleic acid sequence encoding the amino acid sequence SEQ. ID. NO: 5. In another embodiment, the nucleic acid sequence encoding the isolated polypeptide or an isolated fusion or chimeric polypeptide described herein having a percent homology of at least 90% with an amino acid sequence of SEQ. ID. NO:1 does not comprise a nucleic acid sequence encoding the amino acid sequence SEQ. ID. NO: 5. In some embodiments, the cell is selected from the group consisting of a mammal cell, an insect cell, a yeast cell, a fungal cell, a bacterium or a plant cell.

In one embodiment, this disclosure provides for a gene therapy vector comprising a nucleic acid sequence encoding an isolated polypeptide or an isolated fusion or chimeric polypeptide described herein that has a percent homology of at least 90% with an amino acid sequence of SEQ. ID. NO:1. In one embodiment, the nucleic acid sequence encoding an isolated polypeptide or an isolated fusion or chimeric polypeptide described herein comprises at the very minimum a nucleic acid sequence encoding the amino acid sequence SEQ. ID. NO: 5. In one embodiment, the gene therapy vector is a viral vector. For example, a lentivirus or an adenovirus.

In another embodiment, this disclosure provides for a composition comprising such a gene therapy vector described herein.

In one embodiment, this disclosure provides for an immunosuppression composition comprising one or more of the each following: (1) an isolated polypeptide described herein; (2) an isolated chimeric polypeptide described herein; (3) a vector comprising a nucleic acid encoding an isolated polypeptide or an isolated chimeric polypeptide described herein; (4) a cell described herein, either alone or in combination, and a pharmaceutically acceptable carrier. For example, the immunosuppression composition comprises an isolated polypeptide described herein, or an isolated chimeric polypeptide described herein, or a vector comprising a nucleic acid encoding an isolated polypeptide or an isolated chimeric polypeptide described herein, or a cell comprising a vector comprising a nucleic acid encoding an isolated polypeptide or an isolated chimeric polypeptide described herein. Alternatively, the immunosuppression composition comprises a combination of one or more isolated polypeptides; one or more isolated chimeric polypeptide; one or more vectors comprising a nucleic acid encoding an isolated polypeptide or an isolated chimeric polypeptides described herein; or one or more cells described herein.

In one embodiment, such an immunosuppression composition can be used for suppressing the immune system in a subject in need thereof. For example, the subject has an immune disease or disorder wherein the immune system is hyperactive and needs suppression. Alternatively, a reduced immune system is desired for certain medical treatment to be successful, e.g., organ transplantation. Accordingly, in one embodiment, this disclosure provides an isolated polypeptide described herein, or an isolated chimeric polypeptide described herein, or a vector described herein, or a cell described herein for use in suppressing the immune system in a subject in need thereof. In another embodiment, this disclosure provides for an immunosuppression composition described herein for use in suppressing the immune system in a subject in need thereof. For example, the immunosuppression composition comprises a vector that is a gene therapy vector carrying a nucleic acid sequence that encodes the isolated polypeptide described herein, or an isolated chimeric polypeptide described herein. The gene therapy vector is use to introduce the nucleic acid sequence for the purpose of in vivo expression of the described polypeptide.

In some embodiments, the compositions described herein do not include tissue culture media, water, and serum.

In another embodiment, this disclosure provides for the use of an isolated polypeptide described herein, or an isolated chimeric polypeptide described herein, or a vector described herein for the manufacture of medicament for suppressing the immune system in a subject in need thereof.

In one embodiment, this disclosure provides for a method of treating an immune system disease or disorder in a subject, comprising administering to a subject in need thereof a therapeutically effective amount of an isolated polypeptide described herein or an isolated chimeric polypeptide of described herein or an immunosuppression composition comprising one or more of the following: (1) an isolated polypeptide described herein; (2) an isolated chimeric polypeptide described herein; (3) a vector described herein; (4) a cell described herein, either alone or in combination, and a pharmaceutically acceptable carrier described herein.

In another embodiment, this disclosure provides for a method of treating an immune system disease or disorder, comprising administering to a subject in need thereof a therapeutically effective amount of a gene therapy vector comprising a nucleic acid sequence encoding an isolated polypeptide or an isolated fusion or chimeric polypeptide described herein that has a percent homology of at least 90% with an amino acid sequence of SEQ. ID. NO:1. In one embodiment, the nucleic acid sequence encoding an isolated polypeptide or an isolated fusion or chimeric polypeptide described herein comprises at the very minimum a nucleic acid sequence encoding the amino acid sequence SEQ. ID. NO: 5. In another embodiment, the method of treating an immune system disease or disorder comprises administering to a subject in need thereof a therapeutically effective amount of a composition comprising a gene therapy vector comprising such a nucleic acid sequence described herein. In one embodiment, the gene therapy vector is a viral vector.

In one embodiment, the subject has a hyperactive immune system.

In one embodiment, the immune system disease or disorder is selected from the group consisting of an autoimmune disease, allergies and asthma.

In one embodiment, the subject has an autoimmune disease or disorder such as inflammatory arthritis, type 1 diabetes mellitus, multiples sclerosis, psoriasis, inflammatory bowel diseases, SLE, and vasculitis, allergic inflammation, such as allergic asthma, atopic dermatitis, and contact hypersensitivity. Other examples of auto-immune-related disease or disorder, but should not be construed to be limited to, include rheumatoid arthritis, multiple sclerosis (MS), systemic lupus erythematosus, Graves' disease (overactive thyroid), Hashimoto's thyroiditis (underactive thyroid), celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/giant cell arteritis, chronic fatigue syndrome CFS), psoriasis, autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis and fibromyalgia (FM)

Organ or tissue transplant rejection occurs when the immune system of the recipient of a transplant attacks the transplanted donor organ or tissue such as the heart, lungs, pancreas, liver, and kidneys. This is because a normal healthy human immune system can distinguish foreign tissues and attempts to destroy them, just as it attempts to destroy infective organisms such as bacteria and viruses.

Acute organ rejection is generally mediated by T cell responses to proteins from the donor organ which differ from those found in the recipient. The development of T cell responses first occurs several days after a transplant if the patient is not taking immunosuppressant drugs. Acute organ rejection is caused by mismatched human leukocyte antigens (HLA) antigens that are present on all cells. HLA antigens are polymorphic therefore the chance of a perfect match is extremely rare. The reason that acute rejection occurs a week after transplantation is because the T-cells involved in rejection must be activated first by the foreign HLA, then differentiate and the antibodies in response to the allograft must be produced before rejection is initiated. These activated T-cells cause the graft cells to lyse or they produce cytokines that recruit other inflammatory cells, eventually causing necrosis of donor tissue. Endothelial cells in vascularized grafts such as kidneys are some of the earliest victims of acute rejection. Damage to the endothelial lining is an early predictor of irreversible acute graft failure. The new organ is then incapable of working at full efficiency, and symptoms of rejection become apparent to the transplant recipient. These symptoms of rejection are very similar to the symptoms of organ failure.

Physicians skilled in the art can recognize and diagnose transplantation rejection. A biopsy of the transplanted organ can confirm that it is being rejected. Some of the signs and symptoms of rejection for specific organs are as follow: Kidney Rejection-Fever over 38° C. or 100.4° F., decreased urine output, weight gain over 2 pounds per day, increased blood pressure, and pain over kidney. Liver Rejection-Fever over 38° C. or 100.4°, fatigue, jaundice (yellowing of skin or eyes), darkening of urine, clay-colored stools, and pain over liver. Pancreas Rejection-Fever over 38° C. or 100.4° F., increased blood sugars and pain over pancreas.

The risk of acute rejection is highest in the first 3 months after transplantation. With the development of powerful immunosuppressive drugs such as cyclosporin, tacrolimus and rapamycin, the incidence of acute rejection has been greatly decreased, however, organ transplant recipients can develop acute rejection episodes months to years after transplantation. Acute rejection episodes can destroy the transplant if it is not recognized and treated appropriately. Episodes occur in around 60-75% of first kidney transplants, and 50 to 60% of liver transplants. Untreated acute rejection leads to scarring and damage of the donor organ, which then require the recipient to undergo second or third organ transplantation, and often set the stage for chronic rejections of grafts.

Accordingly, administration of a therapeutically effective amount of an isolated polypeptide described herein or an isolated chimeric polypeptide of described herein or an immunosuppression composition described herein shortly before organ or tissue transplantation, or immediately after transplantation can prevent organ/tissue transplantation rejection from developing. The isolated polypeptide, the isolated chimeric polypeptide or the immunosuppression composition described herein can also be administered at the initial diagnosis of such transplantation rejection to stop and/or prevent the rejection from progress further, or to slow the rejection progression to buy time while searching/waiting for another suitable organ to become available for transplantation. It is also contemplated that the therapeutically effective amount of isolated polypeptide, the isolated chimeric polypeptide or the immunosuppression composition described herein can be administered in conjunction with powerful immunosuppressive drugs such as cyclosporin, tacrolimus and rapamycin to suppress organ or tissue transplantation rejection.

In one embodiment, this disclosure provides for a method of suppressing a graft-versus-host disease (GVHD) in a subject comprising administering to the subject in need thereof a therapeutically effective amount of an isolated polypeptide described herein or an isolated chimeric polypeptide of described herein or an immunosuppression composition comprising one or more of the following: (1) an isolated polypeptide described herein; (2) an isolated chimeric polypeptide described herein; (3) a vector described herein; (4) a cell described herein, either alone or in combination, and a pharmaceutically acceptable carrier described herein.

In another embodiment, this disclosure provides for a method of suppressing a graft-versus-host disease (GVHD) in a subject comprising administering to the subject in need thereof a therapeutically effective amount of a gene therapy vector comprising a nucleic acid sequence encoding an isolated polypeptide or an isolated fusion or chimeric polypeptide described herein that has a percent homology of at least 90% with an amino acid sequence of SEQ. ID. NO:1.

In one embodiment, the nucleic acid sequence encoding an isolated polypeptide or an isolated fusion or chimeric polypeptide described herein comprises at the very minimum a nucleic acid sequence encoding the amino acid sequence SEQ. ID. NO: 5. In another embodiment, the method of suppressing a GVHD in a subject comprises administering to a subject in need thereof a therapeutically effective amount of a composition comprising a gene therapy vector comprising such a nucleic acid sequence described herein.

GVHD is a common complication of allogeneic bone marrow transplantation in which functional immune cells in the transplanted marrow recognize the recipient as "foreign" and mount an immunologic attack. After bone marrow transplantation, T cells present in the graft, neither as contaminants or intentionally introduced into the host, attack the tissues of the transplant recipient after perceiving host tissues as antigenically foreign. The T cells produce an excess of cytokines, including tumor necrosis factor (TNF) alpha and interleukin-1 (IL-1). A wide range of host antigens can initiate graft-versus-host-disease, among them the human leukocyte antigens (HLAs). However, graft-versus-host disease can occur even when HLA-identical siblings are the donors. HLA-identical siblings or HLA-identical unrelated donors often have genetically different proteins (called minor histocompatibility antigens) that can be presented by MHC molecules to the recipient's T-cells, which see these antigens as foreign and so mount an immune response.

While donor T-cells are undesirable as effector cells of graft-versus-host-disease, they are valuable for engraftment by preventing the recipient's residual immune system from rejecting the bone marrow graft (host-versus-graft). Additionally, as bone marrow transplantation is frequently used to cure cancer, mainly leukemias, donor T-cells have proven to have a valuable graft-versus-tumor effect.

Classically, acute graft-versus-host-disease is characterized by selective damage to the liver, skin and mucosa, and the gastrointestinal tract. Newer research indicates that other graft-versus-host-disease target organs include the immune system (the hematopoietic system—e.g. the bone marrow and the thymus) itself, and the lungs in the form of idiopathic pneumonitis. Chronic graft-versus-host-disease damages the above organs, but also causes changes to the connective tissue (e.g. of the skin and exocrine glands).

Transfusion-associated graft versus host disease (TA-GvHD) is a rare complication of blood transfusion, in which the donor T lymphocytes mount an immune response against the recipient's lymphoid tissue. Donor lymphocytes are usually identified as foreign and destroyed by the recipient's immune system. However, in situations where the recipient is immunocompromised (inborn immunodeficiency, acquired immunodeficiency, malignancy), or when the donor is homozygous and the recipient is heterozygous for an HLA haplotype (as can occur in directed donations from first-degree relatives), the recipient's immune system is not able to destroy the donor lymphocytes. This can result in graft versus host disease.

Graft-versus-host-disease can largely be avoided by performing a T-cell depleted bone marrow transplant. These types of transplants result in reduced target organ damage and generally less graft-versus-host-disease, but at a cost of diminished graft-versus-tumor effect, a greater risk of engraftment failure, and general immunodeficiency, resulting in a patient more susceptible to viral, bacterial, and fungal infection. Methotrexate and cyclosporin are common drugs used for GVHD prophylaxis.

In one embodiment, the therapeutic methods described herein further comprising administrating in combination with at least one immunosuppressant therapy. Non-limiting examples of immunosuppressant therapy include azathioprine, infliximab, omalizumab, daclizumab, adalimumab, eculizumab, efalizumab, natalizumab, and omalizumab, methotrexate, cyclosporin, daclizumab, basiliximab, azathioprine, muromonab-CD3, and mycophenolate.

In one embodiment of the therapeutic methods described herein, the method further comprises selecting the subject in need of therapeutic intervention, for example, selecting a subject who has an autoimmune disease or disorder, a hyperactive immune system, some sort of allergies, and asthma. In one embodiment of the therapeutic methods described herein, the method further comprises selecting the subject who exhibit at least one symptom of an autoimmune disease or disorder, a hyperactive immune system, some sort of allergies, and asthma.

In one embodiment of the method of suppressing a graft-versus-host disease described herein, the method further comprises selecting the subject in need of therapeutic intervention, for example, the subject shows signs of rejection of the transplanted tissue or organ. In one embodiment, the subject has previous history of rejecting a transplanted tissue or organ.

*V. parahaemolyticus* is a leading cause of diarrhea linked to the consumption of contaminated seafood worldwide (Su and Liu, 2007). Biopsies from patients infected with *V. parahaemolyticus* show disruption of the intestinal epithelium along with evidence of inflammation (Qadri et al., 2003), and similar signs of disease have been observed in ligated ileal loops in infected adult rabbits and in orally infected infant rabbits, both of which are used as animal models of *V. parahaemolyticus* infection (Park et al., 2004; Ritchie et al., 2012). Analyses using these and other animal models strongly indicate that the virulence of this organism is dependent upon a type III secretion system (T3SS) encoded on *V. parahaemolyticus* chromosome II (T3SS2) (Park et al., 2004; Hiyoshi et al., 2010; Piñeyro et al., 2010; Ritchie et al., 2012). Strains lacking a functional T3SS2 fail to colonize the intestine of infant rabbits and they do not induce signs of disease in either model. T3SS2 has also been linked to suppression of the host innate immune response; it appears to inhibit production of the chemokine IL-8, through a mechanism that has not been described (Matlawska-Wasowska et al., 2010). A variety of phenotypes, including cytotoxicity and cytokine induction, have been linked to T3SS1 (encoded on chromosome I) in tissue culture-based assays (Park et al., 2004; Bhattacharjee et al., 2006; Burdette et al., 2008 and 2009; Shimohata and Takahashi, 2010; Zhou et al., 2010; Broberg et al., 2011). However, it appears to play only a minor role in pathogenesis within the gastrointestinal tract (Park et al., 2004; Ritchie et al., 2012). T3SS1 may instead contribute to *V. parahaemolyticus* interactions with some marine host(s), since this T3SS is found in all *V. parahaemolyticus* strains, including environmental/non-pathogenic isolates (Makino et al., 2003). In contrast, T3SS2 is largely absent from environmental/non-pathogenic isolates (Park et al., 2004).

T3SS are essential for the virulence of several other Gram-negative pathogens, and they are used by bacteria to manipulate a variety of host cell processes that influence pathogen survival and growth (Coburn et al., 2007; Dean, 2011). These multi-component molecular machines enable bacteria to transport proteins, referred to as 'effectors', from the bacterial cytoplasm, where they are synthesized, directly into the eukaryotic cell cytoplasm. Release of effectors from bacteria is typically triggered by contact between the pathogen and the host; however, secretion-inducing stimuli that are independent of host cells have also been identified. Effectors have been found to dampen the innate immune response, inhibit phagocytosis, re-organize cytoskeletal proteins to promote pathogen internalization, and modulate several other processes (Cornelis, 2006; Galán, 2009). Various effectors have been described that interfere with innate immunity via disrupting nuclear factor—kappa B (NF-NB) activation, the predominant host pro-inflammatory response to microbial threats (Neish and Naumann, 2011). In addition, effectors can influence mitogen activated kinase (MAPK) pathways, either independently of or in conjunction with modulation of NF-NB signaling (Trosky et al., 2007; Bruno et al., 2009; Matlawska-Wasowska et al., 2010; Shimohata et al., 2011). The MAPKs p38, JNK and ERK orchestrate cellular responses to external stress; they are also involved in innate and adaptive immune responses.

The canonical pathway for NF-KB activation, which is critically important for the development of both innate and adaptive immune responses, is initiated by interactions between cytokines (such as Tumor Necrosis Factor alpha (TNFα) and Interleukin-1β (IL-1β) or other microbe associated molecular patterns (e.g., LPS) and membrane receptors. Via a variety of protein intermediaries, these receptors recruit and activate TNF-receptor associated factors (TRAFs), cellular inhibitors of apoptosis (cIAPs), and the linear ubiquitin assembly complex (LUBAC). Nondegradative TRAF ubiquitinylation then recruits the adaptor molecules TAB2/TAB3 and activates the TAB1/TAK1 (also called MAP3K7) complex, which leads both to activation of the ERK, JNK and P38 MAPK pathways and of the central IKK complex. Activated IKK phosphorylates RelA (an NF-KB component also known as p65) and its associated inhibitor IkBa, thereby triggering IkBa degradation and release of the p65/p50 NF-¬KB transcription factor complex, which translocates to the nucleus and activates target gene transcription (Hayden and Ghosh, 2011).

NF-KB family proteins can also be activated by a separate ("non-canonical") pathway that follows activation of a subset of TNF receptor family members. Signaling via the non-¬canonical pathway triggers proteasomal removal of the IKB residues from p100, the precursor of the p52 NF-KB transcription factor. p52 homodimers and p52/RelB heterodimers then translocate into the nucleus to regulate transcription (Sun, 2011). Activation of the non¬canonical pathway is most frequently observed in the development and maintenance of lymphoid organs.

T3SS effectors that modulate NF-NB and MAPK signaling are produced by a wide variety of bacterial pathogens, and they interfere with many steps of the signaling cascades, often via distinct mechanisms (Neish and Naumann, 2011). In general, T3SS effector proteins vary among organisms to a considerably greater extent than structural components; they are often organism-specific, and consequently can be difficult to identify by purely bioinformatic approaches. However, some effector proteins harbor domains that are ordinarily found in eukaryotic proteins and can therefore be tentatively identified. Furthermore, gene clusters that encode secretion machinery components often contain effector genes as well. Five translocated *V. parahaemolyticus* T3SS2 effectors have been identified to date. These proteins include a Ser/Thr acetyltransferase (VopA; Trosky et al., 2007), an actin nucleator, (VopL; Liverman et al., 2007), an ADP ribosyltransferase (VopT; (Kodama et al., 2007), an actin bundling protein, (VopV; (Hiyoshi et al., 2011), and a homolog of cytotoxic necrotizing factor (VopC; Akeda et al., 2011). With the exception of VopV, which has been shown to be critical for *V. parahaemolyticus*-induced enterotoxicity in rabbit ileal loops, there is no knowledge of the role of T3SS2 effectors in the pathogenesis of diarrhea, epithelial disruption, or inflammation caused by *V. parahaemolyticus*.

Using 2D gel electrophoresis, the inventors have identified three new proteins secreted by T3SS2: VPA1336, VPA1343, and VPA1350. VPA1336, here renamed VopZ, appears to be a multifunctional effector that is essential for *V. parahaemolyticus* to colonize the intestine and to induce diarrhea. It was demonstrated that VopZ inhibits both MAPK and NF-NB innate immune signaling pathways. Notably, VopZ's effects on the host are genetically separable. A small internal vopZ deletion abrogates its effect on the MAPK and NF-NB pathways, and prevents *V. parahaemolyticus*-associated diarrhea, but does not impair intestinal colonization. Thus, inhibition of MAPK/NF-NB-mediated innate immune response (or its consequences) appears to be critical for *V. parahaemolyticus* pathogenicity.

Accordingly, a bacterium with a functional T3SS2 and expressing a mutated VopZ can be exploited to specifically deliver desired extraneous proteins to host animal cells, for example, cells of the small intestine if the bacterium is a *V. parahaemolyticus* because that is the natural target of *V. parahaemolyticus*. In other words, such a bacterium is used as a delivery vehicle to host animal cells, e.g., cells of the small intestine in the host organism. Such a bacterium can also be used as a vaccine, because the delivered extraneous proteins can be an antigen for the purpose of stimulating an immune response to that antigen.

In one embodiment, this disclosure provides for an isolated live attenuated bacterium comprising a nucleic acid sequence encoding a mutant VopZ protein. In one embodiment, the mutant VopZ does not exhibit any immunosuppressive activities as determined by the assays described in the Example section or any assays known in the art.

In one embodiment, provided herein is a composition comprising isolated live attenuated bacteria comprising a nucleic acid encoding a mutant VopZ and a pharmaceutically acceptable carrier.

In one embodiment, such a composition comprising isolated live attenuated bacteria comprising a nucleic acid sequence encoding a mutant VopZ protein and a pharmaceutically acceptable carrier is for use in the vaccination of a host subject against infection by *V. parahaemolyticus*. In one embodiment, such a composition would further comprise an adjuvant. In one embodiment, the adjuvant can be an immunologic adjuvant, i.e., to simulate the immune system and aid the immune response to the antigen. In another embodiment, the adjuvant can be a stabilizer adjuvant, which is to aid in stabilizing formulations of antigens in the vaccine.

Additionally, in another embodiment, such a composition comprising isolated live attenuated bacteria comprising a nucleic acid encoding a mutant VopZ protein and a pharmaceutically acceptable carrier is for use in the introduction of extraneous protein into an animal cell, e.g., a host cell. In one embodiment, the host cell is an animal cell.

Accordingly, in one embodiment, provided herein is an isolated live attenuated bacterium comprising a nucleic acid encoding a mutant VopZ protein for use in the introduction of extraneous protein into animal cells.

In one embodiment, provided herein is an isolated live attenuated bacterium comprising a nucleic acid encoding a mutant VopZ protein for use in the manufacture of a composition for the introduction of at least one extraneous protein into an animal cell. In another embodiment, provided herein is an isolated live attenuated bacterium comprising a nucleic acid encoding a mutant VopZ protein for use in the manufacture of a vaccine composition.

In one embodiment, provided herein is a method of introducing an extraneous protein into an animal cell comprising contacting the animal cell with at least one live attenuated bacterium comprising a nucleic acid encoding a mutant VopZ protein described herein or contacting the animal cell with a composition comprising isolated live attenuated bacteria comprising a nucleic acid encoding a mutant VopZ protein and a pharmaceutically acceptable carrier.

In one embodiment, provided herein is a method of introducing an extraneous protein into an animal cell comprising introducing a nucleic acid sequence encoding the extraneous protein into a live attenuated bacterium comprising a nucleic acid sequence encoding a mutant VopZ protein described herein and administering the resultant bacterium into the animal cell or administering to an animal. In one embodiment, the administering of the resultant bacterium into the animal cell comprises contacting the animal cell with the resultant bacterium. In one embodiment, the contacting can be in vivo, in vitro or ex vivo. In another embodiment, the animal cells are cultured in vitro.

In one embodiment, provided herein is a delivery vehicle for introducing an extraneous protein into an animal cell, wherein the delivery vehicle is an isolated live attenuated bacterium comprising a nucleic acid encoding a mutant VopZ protein described herein.

In one embodiment, the live attenuated bacterium retains the ability to colonize the intestine of a subject host organism. In another embodiment, the live attenuated bacterium, after colonizing the intestine of a subject host organism, does not cause the typical tissue pathology (damage to the intestine epithelia known in the art) or watery diarrhea or vomiting. In another embodiment, the live attenuated bacterium has a T3SS system. T3SSs are multi-protein complex machines used by many Gram-negative bacteria to inject virulence proteins (effectors) into eukaryotic host cells. The effectors modulate a wide range of cellular pathways to promote bacterial proliferation. Type III secretion systems are known in the art, for example, described in review by Francisco Ramos-Morales in ISRN Cell Biology, Volume 2012 (2012), Article ID 787934, 36 pages; and in Kodama T, et al., 2007, Cell Microbiol 9(11):2598-2609.

In one embodiment, the isolated attenuated bacterium is of the *Vibro* genus. In another embodiment, the isolated attenuated bacterium is of the *Salmonella* genus.

In one embodiment, the isolated attenuated bacterium is *V. parahaemolyticus* strain RIMD2210633.

In one embodiment, the encoded mutated VopZ protein is a polypeptide comprising SEQ. ID. NO. 3 Amino acid sequence of vopZΔ38-62 is MSNINNSVSLFIRDT-VDGEFDKATSKQSNTDDDFSKIDEECDTELLQN-TRSIESVKERGLLNFLFR HPTKNVYIRPTNKKRDIEQ-NEIVLTLQYQQSNYNFKWRKIEIEGVKVRLEKNTP-GLRVFNSLHFD NNNFVSIIDEKIYSKNNEFAYLSSD-FKKYINVENYTRSIAIPLASTMSFDLSVNYFNQ-INTLNKYRV LYKKKYYIFEFENGKLVNFMRG-YNDGY (SEQ. ID. NO: 3)

In another embodiment, the encoded mutated VopZ protein is a polypeptide lacking at least the amino acid residues 38-62 of SEQ. ID. NO:1. SEQ. ID. NO: 1 is the full length, non-mutated, VopZ of *V. parahaemolyticus*.

In another embodiment, the nucleic acid sequence encoding the mutated VopZ protein is SEQ. ID. NO:4. The nucleic acid sequence of vopZΔ38-62 is (SEQ. ID. NO: 4)
ATGAGCAACATTAATAATTCTGTATCGCTATTCATTCGAGATACGGTAGA

CGGTGAATTTGATAAAGCAACCTCTAAACAATCTAATACTGATGATGACT

TCTCTAAAATTGATGAGGAGTGTGATACAGAATTATTGCAGAATACACGA

AGTATTGAATCGGTTAAAGAAAGGGGTTTATTAAATTTTTTATTCCGTCA

TCCTACGAAAAATGTCTATATCAGACCTACCAATAAAAAACGCGATATTG

AGCAAAACGAGATTGTTCTGACGCTGCAGTATCAGCAATCGAATTATAAT

TTTAAGTGGAGAAAGATTGAGATAGAGGGGGTGAAAGTTAGATTAGAAAA

AAATACTCCTGGACTTAGAGTATTCAATTCTCTTCACTTTGATAATAATA

ATTTTGTTAGCATAATAGATGAAAAAATATATTCAAAAAATAATGAATTC

GCGTATTTGAGTAGTGATTTTAAAAAATATATAAACGTAGAGAACTATAC

AAGAAGTATAGCTATCCCCCTAGCTAGTACGATGAGTTTTGATCTTTCTG

TAAATTATTTTAATCAAATCAATACCTTGAATAAGTACCGAGTGTTATAT

AAGAAAAAATATTATATATTTGAATTTGAAAATGGAAAATTAGTTAATTT

TATGCGAGGTTATAATGACGGTTATTGA.

In one embodiment, the encoded mutated VopZ protein comprises an amino acid sequence having a percent homology of at least 90% with an amino acid sequence of SEQ. ID. NO:3. In another embodiment, the encoded mutated VopZ protein is translocated into a cell by the attenuated bacteria.

In some embodiments, the encoded mutated VopZ protein also encompasses at least one amino acid residue deletion, at least one amino acid residue addition, and/or at least one amino acid residue substitution. Such mutation does not impede the synthesis of the mutated VopZ or the translocation of the mutated VopZ into a cell by the attenuated bacteria.

In one embodiment, the animal cell is a mammalian cell. In one embodiment, the mammalian cells are human cells.

In one embodiment, the mammalian cells are cells of a mucosal epithelium. In one embodiment, the mucosal epithelium is the intestinal mucosal epithelium of an animal.

In one embodiment, wherein the bacteria or composition is to be administered to an animal, the animal is a mammal. In one embodiment, the mammal is a human. In one embodiment, the live attenuated bacteria or composition is to be administered orally to the animal.

In one embodiment, the bacteria additionally comprising at least one nucleic acid encoding an extraneous protein to be introduced to the animal cell.

In one embodiment, the extraneous protein is an antigen, e.g., the HIV coat protein. In another embodiment, the extraneous protein is a therapeutic agent, such as the therapeutic agents for Crohn's disease. For example, the therapeutic agents can be infliximab (INN; trade name REMICADE®), adalimumab (HUMIRA®), certolizumab (CDP870; CIMZIA®), all of which are human or humanized monoclonal antibodies against tumor necrosis factor alpha (TNF-α); and natalizumab (TYSABRI®), humanized monoclonal antibodies against the cell adhesion molecule α4-integrin.

In one embodiment, the nucleic acid sequence encoding the extraneous protein in a live attenuated bacterium for the purpose of introducing into a host cell of an organism comprises a nucleic acid sequence encoding the mutant VopZ protein described herein. In other words, the live attenuated bacterium would express a fusion protein comprising the extraneous protein and the mutated VopZ. In one embodiment, the extraneous protein is located at the carboxyl terminus of the mutated VopZ, meaning the mutated VopZ is translated first followed by the extraneous protein. In this design, the T3SS2 export translocation signal of the VopZ is used to ensure translocation of the extraneous protein into the host cell. In accordance with this design, provided herein is a nucleic acid sequence encoding a fusion polypeptide comprising an extraneous protein and a mutant VopZ protein. Constructions of protein-coding nucleic acid sequences for expressing fusion polypeptides in bacteria are known to one of ordinary skill in the art, and are also described in the Example section and in US Patent Application No: 2005/0089,988 which is incorporated by reference in its entirety.

In another embodiment, the nucleic acid sequence encoding the extraneous protein in a live attenuated bacterium for the purpose of introducing into a host cell of an organism comprises a nucleic acid sequence encoding a Vop protein. In one embodiment, the Vop protein is select from the group consisting of VopT, VopA, VopL, VopV and VopC. These five Vop proteins are known effector molecules of *V. parahaemolyticus* and thus they are also translocated by the bacteria into the host cell. In this design, the live attenuated bacterium would express a fusion protein comprising the extraneous protein and the selected Vop protein. In one embodiment, the extraneous protein is located at the carboxyl terminus of the selected Vop protein, meaning the selected Vop is translated first followed by the extraneous protein. In this design, the T3SS2 export translocation signal of the selected Vop is used to ensure translocation of the extraneous protein into the host cell. The Genbank™ Accession coding nucleic acid sequences of these Vop proteins are the following: VopT: NP_800837.1 (SEQ ID NO: 7); VopA: NP_800856.1 (SEQ ID NO: 8); VopL: NP_800881.1 (SEQ ID NO: 9); VopV: NP_800867.1 (SEQ ID NO: 10); and VopC: NP_800831.1 (SEQ ID NO: 11).

In some embodiments, the selected VopZ protein encompasses at least one amino acid residue deletion, at least one amino acid residue addition, and/or at least one amino acid residue substitution. Such mutations do not impede the synthesis or translocation of the mutated Vop fusion protein into a cell by the attenuated bacteria.

In another embodiment, the nucleic acid sequence encoding the extraneous protein in a live attenuated bacterium for the purpose of introducing into a host cell of an organism comprises a nucleic acid sequence comprising the following component in tandem arrangement from the 5' to 3' direction: a promoter sequence, which is operable linked to a first nucleic acid sequence encoding the first 10-50 amino acid residues of a Vop protein, and this is also operable linked to a second nucleic acid sequence encoding the desired extraneous protein. In this design, the first 10-50 amino acid residues of the selected Vop protein provide the secretion signal necessary for the translocation of the encoded extraneous protein.

Numerous promoter sequences for the transcription of protein in bacteria are known in the art. For example, the LacZ promoter can be used. Other promoters are described in US Patent Application No: 2005/0089,988 which is incorporated by reference in its entirety.

In one embodiment, the Vop protein is select from the group consisting of VopT, VopA, VopL, VopV, VopZ, and VopC. In the embodiment where the selected Vop protein is VopZ, the first nucleic acid sequence that is operable linked to the promoter encodes for only the first 10-38 amino acids of VopZ.

In some embodiments, the first nucleic acid sequence operable linked to the promoter encodes for the first 10-15, 10-20, 10-25, 10-30, 10-35, 10-40, 10-45, 15-20, 15-25, 15-30, 15-35, 15-40, 15-45, 15-50, 20-25, 20-30, 20-35, 20-40, 20-45, 20-50, 25-30, 25-35, 25-40, 25-45, 25-50, 30-35, 35-40, 35-45, 35-50, 40-45, or 45-50 amino acid residues of a Vop protein.

In some embodiments, the first nucleic acid sequence operable linked to the promoter encodes for the first 10, 15, 20, 25, 30, 35, 40, 45, or 50 amino acid residues of a Vop protein.

Non-limiting examples of desirable extraneous protein include human immunodeficiency virus coat protein gp120, fragments of immunogenic pneumococcal proteins from *Streptococcus pneumonia*, cholera toxin B and hepatitis B surface antigen, genetic toxoids of cholera toxin E, Cori It, malaria antigens, MTB antigens, *Shigella* antigens, *N. Gonorrhea* antigens, *Chymaldia trachomatis* antigens, Influenza antigens, and RSV antigens.

In one embodiment, provided herein is a vaccine for reducing in an individual infection symptom caused by *Vibro* bacteria, the vaccine comprising: (i) an attenuated *Vibro* bacterium comprising a nucleic acid encoding a mutant VopZ protein comprising an amino acid sequence having a percent homology of at least 90% with an amino acid sequence of SEQ. ID. NO:2; and (ii) a pharmaceutically acceptable carrier.

In one embodiment, provided herein is a vaccine for reducing in an individual infection symptoms, wherein the attenuated *Vibro* bacteria is *Vibro parahaemolyticus*. In one embodiment, the attenuated *V. parahaemolyticus* is RIMD2210633.

In one embodiment, provided herein is a method for reducing in an individual disease symptom caused by *Vibro* bacteria comprising administering to the individual attenuated *Vibro* bacteria in a pharmaceutically acceptable carrier, in an immunologically effective dose.

Cloning of Vop Proteins and Gene Therapy Vectors

Full length Vop or fusion proteins thereof can also be synthesized and purified by any methods that are well known in the art or as described in the Examples. Similarly, gene therapy vectors comprising nucleic acid sequences encoding full length Vop or fusion proteins thereof can also be synthesized and purified by any methods that are well known in the art. Encompassed nucleotide sequences include any one of VopT, VopA, VopL, VopV, VopZ, and VopC. In some embodiments, molecular biology methods and recombinant heterologous protein expression systems are used. For example, recombinant protein may be expressed in bacteria, mammal, insects, yeast, or plant cells.

Conventional polymerase chain reaction (PCR) cloning techniques can be used to generate the protein coding nucleotide sequences from the template nucleotide sequences such as SEQ. ID. NOS: 2 and 4, and those of VopT: NP_800837.1 (SEQ ID NO: 7); VopA: NP_800856.1 (SEQ ID NO: 8); VopL: NP_800881.1 (SEQ ID NO: 9); VopV: NP_800867.1 (SEQ ID NO: 10); and VopC: NP_800831.1 (SEQ ID NO: 11). Specific primers will be designed to correspond to the desired coding region of the Vop template nucleotide sequences. These primers are used to cloned the PCR coding amplified sequence into a general purpose cloning vector such as pUC19, pBR322, pBluescript vectors (STRATAGENE® Inc.) or pCR TOPO® from INVITROGEN™ Inc. Additionally, the PCR amplified sequence can be subcloned into the vector pDNR-dual which then can be used for further molecular biological manipulations such as site-directed mutagenesis, or for subcloned into protein expression vectors or viral vectors, e.g., gene therapy vectors, for protein synthesis in a variety of protein expression systems using host cells selected from the group consisting of mammalian cell lines, insect cell lines, yeast, and plant cells. Alternatively, the Cre recombinase system can be used to move the PCR amplified coding sequence into vectors for expression in mammalian cells. e.g., pCMVneo vector.

Examples of other expression vectors and host cells are the pET vectors (NOVAGEN), pGEX vectors (Amersham Pharmacia), and pMAL vectors (New England labs. Inc.) for protein expression in *E. coli* host cell such as BL21, BL21 (DE3) and AD494 (DE3)pLysS, Rosetta (DE3), and Origami (DE3) (NOVAGEN); the strong CMV promoter-based pcDNA3.1 (Invitrogen) and pClneo vectors (PROMEGA) for expression in mammalian cell lines such as CHO, COS, HEK-293, Jurkat, and MCF-7; replication incompetent adenoviral vector vectors pAdeno X, pAd5F35, pLP-Adeno-X-CMV (CLONTECH), pAd/CMV/V5-DEST, pAd-DEST vector (INVITROGEN) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4/V5-DEST™, pLenti6/V5-DEST™, and pLenti6.2/V5-GW/lacZ (INVITROGEN) for lentivirus-mediated gene transfer and expression in mammalian cells; adenovirus-associated virus expression vectors such as pAAV-MCS, pAAV-IRES-hrGFP, and pAAV-RC vector (STRATAGENE) for adeno-associated virus-mediated gene transfer and expression in mammalian cells; BACpak6 baculovirus (CLONTECH) and pFastBac™ HT (INVITROGEN) for the expression in *Spodopera frugiperda* 9 (Sf9) and Sfl 1 insect cell lines; pMT/BiP/V5-His (INVITROGEN) for the expression in *Drosophila Schneider* S2 cells; *Pichia* expression vectors pPICZα, pPICZ, pFLDα and pFLD (INVITROGEN) for expression in *Pichia pastoris* and vectors pMETα and pMET for expression in *P. methanolica*; pYES2/GS and pYD1 (INVITROGEN) vectors for expression in yeast *Saccharomyces cerevisiae*. Recent advances in the large scale expression heterologous proteins in *Chlamydomonas reinhardtii* are described by Griesbeck C. et al. 2006 Mol. Biotechnol. 34:213-33 and Fuhrmann M. 2004, Methods Mol Med. 94:191-5. Foreign heterologous coding sequences are inserted into the genome of the nucleus, chloroplast and mitochondria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. Biolistic gene gun method is used to introduce the vector in the algae. Upon its entry into chloroplasts, the foreign DNA is released from the gene gun particles and integrates into the chloroplast genome through homologous recombination.

In some embodiments, fusion Vop proteins are contemplated. Any one of full length VopT, VopA, VopL, VopV, VopZ, and VopC, or shorter fragment portion (or part of) thereof, e.g., the first 10-50 amino acid residues of VopT, VopA, VopL, VopV, VopZ, and VopC, can be fused to transferrin, IgG, or albumin, to name a few, to enhance serum half-life and pharmacokinetics in the individual being treated with the resultant fusion protein. Vop proteins or shorter fragments thereof can also be fused to a tag protein such as tandem histidine residues (6×His), GST, myc, thioredoxin first 105 amino acids or HA tag for the purification and/or enhance solubility of the expressed recombinant protein in heterologous system. Enzymatic digestion with serine proteases such as thrombin and enterokinase cleave and release the VopZ protein from the histidine or myc tag, releasing the VopZ from the affinity resin while the histidine-tags and myc-tags are left attached to the affinity resin.

In addition, the therapeutic agent, extraneous protein, or antigenic agents contemplated herein to be introduced using the delivery vehicle described herein can be a fusion protein. Accordingly, fusion extraneous protein such as fusion therapeutic agents and fusion antigenic agents are contemplated. For example, biologic proteins such as monoclonal antibodies that are used as therapeutic agents, or antigenic proteins such as HIV gp 120, can be fused to a full length Vop protein or shorter fragment portion of a Vop protein. PCR cloning molecular techniques known in the art can be used to create the desired nucleic acid sequence coding the selected fusion protein. For example, VopZ (1-15 amino acid)-gp120 fusion; VopT (1-25 amino acid)-gp120 fusion; VopL (1-30 amino acid)-gp120 fusion; VopZ (1-15 amino acid)-monoclonal antibodies fusion; VopZ (1-25 amino acid)-monoclonal antibodies fusion; VopZ (1-50 amino acid)-monoclonal antibodies fusion; VopL (1-35 amino acid)-monoclonal antibodies fusion; and VopA (1-40 amino acid)-monoclonal antibodies fusion. Additionally, PCR cloning molecular techniques known in the art can be used to create amino acid deletions or additions in the selected fusion protein. Moreover, specific restriction enzyme digestion sites can be added to facilitate cloning. Additionally, specific enzymatic digestion sites can be designed into the fusion protein to facilitate separation of the different protein parts in the fusion protein. The desired nucleic acid sequence can then be placed in the delivery vehicle described herein for introduction to a host cell. Furthermore, specific site-directed mutagenesis of any nucleic sequence described in any vector contemplated herein can be used to create specific amino acid mutations, e.g., additions, deletions, and substitutions.

In one embodiment, the fusion Vop proteins are contemplated herein retain the ability to translocate into host cells when the delivery vehicle expressing the fusion Vop proteins comes in contact with the host cells. In one embodiment, the delivery vehicle is a live attenuated bacterium expressing a a polypeptide comprising an amino acid sequence having 90% homology to SEQ. ID. NO:3, in addition to expressing a fusion Vop protein described herein. Similarly, in one embodiment, the fusion Vop proteins contemplated herein having mutations such as amino acid residues deletions or additions or substitutions, also retain the ability to translocate into host cells when the delivery vehicle expressing the fusion Vop proteins comes in contact with the host cells. In one embodiment, one or more mutations are located in the Vop protein part of the fusion protein, e.g., within the first 10-50 amino acid residues of the Vop protein when only the first 10-50 amino acid residues are incorporated into the fusion protein, or within the full length Vop protein if the full length Vop protein is incorporated into the Vop protein. In another embodiment, the contemplated one or more mutations are located in the extraneous protein part of the fusion protein.

Standard techniques known to those of skill in the art can be used to introduce mutations in the nucleotide sequence encoding any one of VopT, VopA, VopL, VopV, VopZ, and VopC, including, for example, site-directed mutagenesis and PCR-mediated mutagenesis which result in amino acid substitutions, additions or deletions. For example, site-directed mutagenesis can be carried out using the QUIKCHANGE® site-directed mutagenesis kit from STRATAGENE according to manufacture's instructions or any method known in the art. In the context of a full length Vop protein that is incorporated into a fusion protein described herein, the mutated proteins described herein comprise less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the full length, non-mutated Vop protein. In the context where only a portion of a Vop protein is incorporated into a fusion protein described herein, e.g., the first 10-50 amino acid residues of a Vop protein is incorporated, the mutated proteins described herein comprise less than less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions, depending the number of amino acid residues of Vop are incorporated into the fusion protein.

In one embodiment, the mutated protein described herein comprises at least one conservative amino acid substitution. In another embodiment, the mutated protein described herein comprises at least one non-conservative amino acid substitution. The resultant mutant VopZ proteins can be screened for immunosuppressive activity by the assays as described herein in the Example. The resultant mutant Vop fusion proteins can be screened for protein translocation activity into host cells by the assays as described herein in the Example.

The introduced mutations can be silent or neutral missense mutations, i.e., have no, or little, effect on the Vop protein's immunosuppressive activity or translocation activity into host cells. These types of mutations can be useful to optimize codon usage, or improve recombinant Vop protein expression and production. One of skill in the art would be able to design and test mutant molecules for desired properties such as no alteration of Vop protein's activities and expression. Following mutagenesis, the encoded protein can routinely be expressed and the functional and/or biological activity of the encoded protein can be determined using techniques described herein or by routinely modifying techniques known in the art.

In one embodiment, the vector that expresses VopZ is a viral vector. The viral vector can be any viral vector known in the art including but not limited to those derived from adenovirus, adeno-associated virus (AAV), retrovirus, and lentivirus. Recombinant viruses provide a versatile system for gene expression studies and therapeutic applications.

A simplified system for generating recombinant adenoviruses is presented by He TC. et. al. Proc. Natl. Acad. Sci. USA 95:2509-2514, 1998. The gene of interest is first cloned into a shuttle vector, e.g. pAdTrack-CMV. The resultant plasmid is linearized by digesting with restriction endonuclease Pme I, and subsequently co-transformed into E. coli. BJ5183 cells with an adenoviral backbone plasmid, e.g. pAdEasy-1 of STRATAGENE's ADEASY™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenoviruses are generated within the HEK 293 cells.

In one embodiment, the invention provides a recombinant lentivirus for the delivery and expression of a VopZ protein in either dividing or non-dividing host cells, e.g., mammalian cells. In one embodiment, the delivery is via contacting the host cells with the recombinant lentivirus or a composition comprising the recombinant lentivirus described. In another embodiment, the delivery is by administering the recombinant lentivirus or a composition comprising the recombinant lentivirus described to a host organism, such as an animal. The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with ViraPower™ Lentiviral Expression systems from Invitrogen.

In one embodiment, provided herein is a recombinant adeno-associated virus (rAAV) vector for the expression of a VopZ protein. In one embodiment, the rAAV vector encoding a VopZ protein is administered to suppress the immune activity in a cell or a host organism. Because AAV is non-pathogenic and does not elicit an immune response, a multitude of pre-clinical studies have reported excellent safety profiles. rAAVs are capable of transducing a broad range of cell types, and transduction is not dependent on active host cell division. High titers, >$10^8$ viral particles/ml, are easily obtained in the supernatant and $10^{11}$-$10^{12}$ viral particles/ml can be obtained with further concentration. The VopZ transgene is integrated into the host genome so expression is long term and stable.

The use of alternative AAV serotypes other than AAV-2 (Davidson et al (2000), PNAS 97 (7)3428-32; Passini et al (2003), J. Virol 77(12):7034-40) has demonstrated different cell tropisms and increased transduction capabilities. (See CED; Bobo et al (1994), PNAS 91(6):2076-80; Nguyen et al (2001), Neuroreport 12(9):1961-4).

Large scale preparation of AAV vectors can be made by a three-plasmid cotransfection of a packaging cell line: AAV vector carrying the VopZ coding sequence, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Formulation and Application

In one embodiment, provided herein is an immunosuppression composition comprising an isolated polypeptide comprising an amino acid sequence having a percent homology of at least 90% with an amino acid sequence of SEQ. ID. NO:1, wherein the polypeptide having immunosuppression activity, or an isolated chimeric polypeptide described or a vector comprising a nucleic acid encoding an isolated polypeptide described, or a cell comprising a vector described, and a pharmaceutically acceptable carrier. In one embodiment, such compositions are used for suppressing the immune response in a host cell or host organism.

In one embodiment, provided herein is a composition comprising isolated live attenuated bacteria comprising a nucleic acid encoding a mutant VopZ protein, and a pharmaceutically acceptable carrier. In some embodiments, this composition is used for introducing extraneous protein into a host cell and/or vaccination against an antigen.

When used in mammalian therapy, these compositions described can be administered in any convenient vehicle that is physiologically acceptable. The compositions can be formulated for a variety of modes of administration, including systemic, topical, oral or localized administration. Techniques and formulations generally can be found in Remington's Pharmaceutical Sciences, Mack Publishing Co., Easton, Pa., latest edition. In each case, a therapeutically effective amount of the isolated polypeptide, the isolated chimeric polypeptide, the isolated live attenuated bacteria, or the vector described is administered in order to achieved the desired purpose, ie immunosuppression, introducing extraneous protein into a host cell and/or vaccination against an antigen.

In one embodiment, a pharmaceutically acceptable carrier encompass a diluent or excipient; non-limiting examples of which include fillers, extenders, binding, wetting agents, disintegrants, surface-active agents, or lubricants, depending on the nature of the mode of administration and dosage forms. Conventional pharmaceutical preparations include tablets, powders, liquid preparations including suspensions, emulsions and solutions, granules, capsules, sprays and suppositories, as well as liquid preparations for injections.

In one embodiment, the pharmaceutically acceptable carriers can be inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of the protein described include polysaccharides such as sodium carboxymethylcellulose or methylcellulose, polyvinylpyrrolidone, polyacrylates, polyoxyethylene-polyoxypropylene-block polymers, polyethylene glycol and wood wax alcohols. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. No. 3,773,919, EP 58,481A, U.S. Pat. No. 3,887,699, EP 158,277A, Canadian Patent No. 1176565, U. Sidman et al., Biopolymers 22:547 (1983) and R. Langer et al., Chem. Tech. 12:98 (1982).

In one embodiment, other ingredients can be added to the pharmaceutical formulations as described herein, such as anti-oxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, the composition described herein takes the form of a cationic liposome formulation; the isolated polypeptide, isolated chimeric polypeptide, vector, cell, or isolated live attenuated bacteria described are contained within a lipid particle or vesicle, such as a liposome or microcrystal. Such liposome formulations are suitable for parenteral administration. The preparation of such lipid formulations is well known. See, e.g., U.S. Pat. Nos. 4,880,635; 4,906,477; 4,911,928; 4,917,951; 4,920,016; and 4,921,757; "DNA-Pharmaceuticals: Formulation and Delivery in Gene Therapy, DNA Vaccination and Immunotherapy" by Martin Schleef (Editor) December 2005, Wiley Publisher; and "Plasmids for Therapy and Vaccination" by Martin Schleef (Editor) 2001; these are incorporated herein as reference in their entirety.

In one embodiment, the pharmaceutical formulation used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The pH of the proteins preparations typically will be about from 6 to 8, although higher or lower pH values can also be appropriate in certain instances.

The gene therapy virus can be in the form of an adenovirus, adeno-associated virus or lentivirus. Such compositions include solutions, suspensions, lotions, gels, creams, ointments, emulsions, skin patches, etc. All of these dosage forms, along with methods for their preparation, are well known in the pharmaceutical and cosmetic art. HARRY'S COSMETICOLOGY (Chemical Publishing, 7th ed. 1982); REMINGTON'S PHARMACEUTICAL SCIENCES (Mack Publishing Co., 18th ed. 1990). Typically, the active ingredient is in a concentration range of 0.1 to 100 mg/ml, in admixture with suitable vehicles. For gene therapy viruses, the dosage ranges from $10^6$ to $10^{14}$ particle per application. Other desirable ingredients for use in such preparations include preservatives, co-solvents, viscosity building agents, carriers, etc. The carrier itself or a component dissolved in the carrier can have palliative or therapeutic properties of its own, including moisturizing, cleansing, or anti-inflammatory/anti-itching properties. Penetration enhancers can, for example, be surface active agents; certain organic solvents, such as di-methylsulfoxide and other sulfoxides, dimethylacetamide and pyrrolidone; certain amides of heterocyclic amines, glycols (e.g. propylene glycol); propylene carbonate; oleic acid; alkyl amines and derivatives; various cationic, anionic, nonionic, and amphoteric surface active agents; and the like.

Routes of administration include systemic routes not limited to intradermal, intramuscular, intraperitoneal, intravenous, subcutaneous, intranasal, epidural, and oral routes. For systemic administration, the formulation is a liquid, e.g., in sterile saline, lactated Ringer's or Hank's solution. In addition, the pharmaceutical formulation can be in solid forms and re-dissolved or suspended immediately prior to use. Lyophilized forms are also included. In one embodiment, the compositions described are administered by any convenient route.

In some embodiments, the compositions described herein are administered to an organism, preferably a mammal, such as a human, in a pharmaceutically acceptable dosage form, including those that can be administered to a human intravenously as a bolus or by continuous infusion over a period of time, by intramuscular, intraperitoneal, intracerebrospinal, subcutaneous, intra-arterial, intrasynovial, intrathecal, oral, topical, or inhalation routes. Topical administration of a pharmacologically effective amount can utilize transdermal delivery systems well known in the art. An example is a dermal patch. Alternatively, the pharmaceutical formulation can be infused upstream from the site of the cells whose activity is to be modulated. Implantable drug pumps, as for example INFUSAID™ pumps (Infusaid, Inc.), are useful for delayed-release intraarterial administration. Intramuscular injection is one example of administering the gene therapy viral vectors described.

The route of administration, dosage form, and the effective amount vary according to the potency of the isolated VopZ proteins, vectors and viral vectors, cells carrying the vectors, the isolated attenuated bacterium, their physicochemical characteristics, and according to the treatment location. The selection of proper dosage is well within the skill of an ordinary skilled physician.

The localized concentration or amount administered to a subject can be determined empirically and will depend upon the purpose of the administration, the area to be treated, the effectiveness of the composition, and the manner of administration. The localized concentration at the site of the targeted cells will desirably be in the range of about 0.05 to 50 M, or more particularly 0.2 to 5 M, although higher or lower dosages can be employed as appropriate. For administration to a subject such as a human, a dosage of from about 0.01, 0.1, or 1 mg/kg up to 50, 100, or 150 mg/kg or more can typically be employed, and from $10^6$ to $10^{14}$ vector/viral particle or cells per application.

The precise dose to be employed in the formulation of the agent will also depend on the route of administration, and the seriousness of the disease or disorder, and should be decided according to the judgment of the practitioner and each patient's circumstances. Effective doses may be extrapolated from dose-response curves derived from in vitro or animal model test systems.

Efficacy testing can be performed during the course of treatment using the methods described herein. Measurements of the degree of severity of a number of symptoms associated with a particular ailment are noted prior to the start of a treatment and then at later specific time period after the start of the treatment. For example, when treating an autoimmune disease such as rheumatoid arthritis, the severity of joint pain can be scored from a number of 1-10, with a score of 1 representing mild discomfort and a score of 10 represent constant unbearable pain with or without movement; the range of motion of an affected joint can also are be measured as a degree of angle for which that joint can move. The joint pain and range of motion are noted before and after a treatment. The severity of joint pain and range of motion after the treatment are compared to those before the treatment. A decrease in the pain score and/or an increase in the degree of angle of joint movement indicate that the treatment is effective in reducing inflammation in the affected joint, thereby decreasing pain and improving joint movement.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective dose can include a single treatment or a series of treatments.

This technology is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the technology described herein. Such equivalents are intended to be encompassed by the following claims.

Example

Materials and Methods

Bacterial Strains, Plasmids, and Culture Conditions

All strains are derived from RIMD2210633 (Makino et al., 2003). vscN1, vscN2 and vscN1/vscN2 strains have been previously described (Hiyoshi et al., 2010). Additional mutants, including vpa1343, vpa1350, vscN1 vopZ', and vscN1 vopZΔ38-62 strains were created by allele exchange, using suicide vector pDM4 as previously described (Zhou et al., 2008). Plasmids pVopZ-His (for vopZ complementation), pVopZ-CyaA, pVopV-CyaA, and pVtrB were constructed using the vector pMMB207 (Morales et al., 1991), and introduced into *V. parahaemolyticus* strains via conjugation. HA-fusion constructs for full length and truncated vopZ were constructed in pCMVHA (CLONETECH®). Strains were cultured in LB medium at 37° C. and supplemented with appropriate antibiotics.

Eukaryotic Cell Lines and Culture Conditions

HeLa, Caco-2 and HEK293 cells were routinely maintained in DMEM (GIBCO®) supplemented with 10% FBS (CLONTECH®) at 37 degrees C. with 5% $CO_2$. For in vitro infection assays, bacterial cells were grown in LB supplemented with 0.04% sodium cholate for 2 h to induce the expression of T3SS2.

Two-Dimensional Gel Analysis and Western Blot Analysis of Bacterial Proteins

To obtain proteins for 2-D PAGE analysis, RIMD2210633 vscN1 pVtrB and RIMD2210633 vscN1 vscN2 pVtrB were cultured in DMEM containing 1 mM IPTG, to induce expression of the T3 SS2 activator, VtrB. After 3 h of growth, cells were removed by centrifugation and filtration, and difference gel electrophoresis (DIGE) analysis was performed on the culture supernatant by Applied Biomics (Hayward, Calif.). Western blot analysis was performed on cell pellets and supernatants from bacteria cultured in LB supplemented with 1 mM IPTG.

Effector-CyaA Fusion Protein-¬Based Analysis of Effector Translocation

Caco-2 cells were cultured for 10 days to achieve differentiation. Differentiated Caco-2 cells were infected with RIMD2210633 vscN1 and RIMD2210633 vscN1 vscN2 containing pCyaA, pVopZ-CyaA or pVopV-CyaA for 1 h in the presence of 0.04% sodium cholate, and then cAMP levels were determined by ELISA as described previously (Zhou et al., 2012b).

Immunofluorescence Detection of VopV Translocation

HeLa cells grown overnight on glass coverslips were infected with *V. parahaemolyticus* overexpressing vtrB for 1 h before being fixed by 4% formalin. Fixed cells were blocked by PBS containing 3% bovine serum albumin (BSA) for 1 h, then VopV was detected with rabbit anti-VopV antisera (generously provided by Dr. Toshio Kodama) and FITC-goat anti-rabbit IgG (SIGMA-ALDRICH®). Actin was stained with rhodamine phalloidin, and DNA was stained with DAPI.

Transfection and Visualization of VopZ within HeLa Cells

HeLa cells grown overnight on coverslips were transfected with HA-VopZ expression constructs using lipofectamine 2000 (LIFE TECHNOLOGIES™). Twenty-four hours after transfection, cells were fixed with 4% formalin, and full-length and truncated VopZ were detected by immunofluorescence using anti-HA (SIGMA-ALDRICH®) and FITC-conjugated anti-mouse IgG (SIGMA-ALDRICH®).

p65 Translocation Assays

HeLa cells grown overnight on coverslips were transfected with HA-VopZ expression constructs for 24 h or infected with V. parahaemolycus strains for 1 h in the presence of 0.04% sodium cholate. After treatment with TNFct (R&D systems; 20 ng/ml) for 1 h, cells were fixed and p65 localization was detected using anti-p65 (CELL SIGNALING™). For each of 3 transfection experiments, p65 localization was assessed in 30 cells with detectable VopZ. For each of 3 infection experiments, p65 localization was determined in 30 randomly selected cells.

NF-kB Activity and IL-8 Production in HEK293 and HeLa Cells

HEK293 cells in which GFP was fused to multiple NF-κB sites (Gewurz et al., 2012) were infected with V. parahaemolyticus for 90 min in the presence of 0.04% sodium cholate and then infection was terminated by addition of gentamicin (200 ng/ml). Cells were then cultured an additional 4-5 hr, either in the presence or absence of TNFα (1 ng/ml). GFP expression was detected via FACS calibur (BD; (Gewurz et al., 2012)). For assays of IL-8 production, HEK293 cells or HeLa cells were infected with V. parahaemolyticus for 90 mins, then treated with TNFα (2 ng/ml; HEK293) or IL-1β (R&D Systems, 25 ng/ml; HeLa) or left untreated for 90 min. IL-8 in culture supernatant was then measured via ELISA (BD).

Detection of MAPK Activation and IkBα Degradation in HEK293 Cells

HEK293 cells were infected with V. parahaemolyticus at an approximate MOI of 5:1 for 90 min in the presence of 0.04% sodium cholate, and infection was terminated by addition of gentamicin (200 ng/ml). Infected cells were stimulated with TNFα (2 ng/ml), then lysed as described (Gewurz et al., 2011) at 0, 15, 30 and 60 min post stimulation.

Protein samples were electrophoresed on SDS PAGE 10% gels, gels (INVITROGEN™), transferred to nitrocellulose membranes, and probed with CELL SIGNALING antibodies against: IKBα (#9242), phospho-JNK (#9251), phosphor-ERK (#9101), phospho-p38 (#9211), JNK (#9252), ERK (#9102), p38 (#9212). Also used were anti-Tubulin (SIGMA, T5168) and anti-LMP1 monoclonal S12.

Detection of Non-Canonical NF-KB Activation.

HEK293 cells were infected with V. parahaemolyticus for 90 min, and infection was terminated by gentamicin addition (200 ng/ml). Infected cells were subsequently stimulated with Latent Membrane Protein 1 expression (LMP1) for approximately 8 hours, lysed with 1% NP40 lysis buffer, and electrophoresed as described above. Membranes were probed with anti-p100/p52 (MILLIPORE, #05-361).

Infection of Infant Rabbits

Infant rabbits were infected as described previously (Ritchie et al., 2012). Briefly, cimetidine-treated rabbits were orogastrically inoculated with $10^9$ CFU of V. parahaemolyticus, and bacterial colonization (CFU/g intestinal tissue) and fluid accumulation were measured 38 h post infection. Fluid accumulation ratios for the distal small intestine were determined by isolating an approximately 5-cm length of tissue using silk ligatures. The intestinal section was weighed and then cut every 0.5 cm to release any luminal fluid, and the tissue pieces were reweighed. The fluid accumulation ratio was calculated as the weight of fluid divided by the weight of the drained tissue. Histological scores were graded by a pathologist.

Results

Previously identified T3SS2 effectors do not play an essential role in intestinal colonization or fluid accumulation.

Figures 8A, 8B:
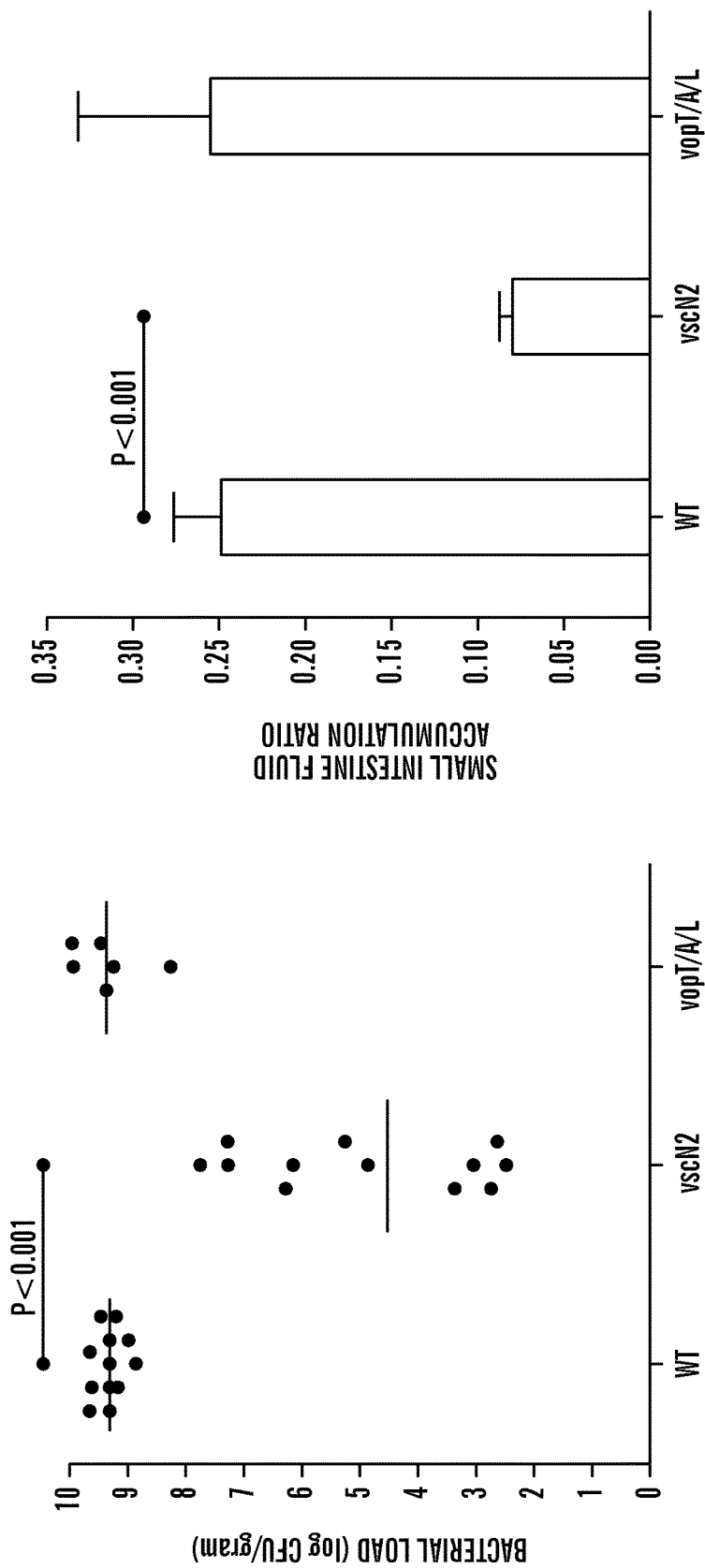
FIGS. 8A-8B show that three previously confirmed T3SS2 effectors do not contribute to *V. parahaemolyticus* pathogenicity in infant rabbits.

Our group recently reported that infant rabbits are useful model hosts to investigate V. parahaemolyticus pathogenicity (Ritchie et al., 2012; Zhou et al., 2012b). It was found that three-day old rabbits orogastrically inoculated with wild type V. parahaemolyticus developed diarrhea and intestinal pathology that closely resembles that observed in humans infected with this organism. In this model, intestinal colonization by a V. parahaemolyticus T3SS2 mutant (vscN2) that is unable to secrete T3SS2-dependent effectors was approximately four orders of magnitude lower than that of wild type (WT) bacteria at the principal sites of host colonization, namely the mid and distal small intestine. Furthermore, the T3SS2 mutant did not elicit intestinal pathology or diarrhea (Ritchie et al., 2012). Thus, one or more of the T3SS2-translocated effectors are critical for V. parahaemolyticus pathogenicity. To test this idea, a V. parahaemolyticus mutant strain (derived from WT strain RIMD2210633; (Makino et al., 2003)) was created. The mutant strain has deletions in vopT, vopA and vopL, which encode the only T3SS2 effectors confirmed at the time this project was initiated. Notably, this triple deletion mutant did not display any evidence of attenuation in the infant rabbit model. Colonization of the distal small intestine by the WT and mutant strains were indistinguishable (FIG. 8A). Furthermore, rabbits inoculated with the mutant and WT strains had similar amounts of diarrhea and fluid accumulation within their small intestines (FIG. 8B), and they displayed apparently identical intestinal pathology (data not shown). The marked difference between the virulence of the vscN2 mutant and the vopT vopL vopA triple mutant suggested that heretofore unidentified T3SS2 effectors play important roles in V. parahaemolyticus intestinal colonization and disease.

Identification of T3SS2-Secreted Proteins

Two-D difference gel electrophoresis (DIGE) was used to identify new T3SS2 secreted effectors. Proteins present in supernatants from a T3SS1-deficient strain (RIMD2210633 vscN1; (Hiyoshi et al., 2010)), which can secrete T3SS2 but not T3SS1 effectors, were labeled with Cy3 (red), and proteins present in supernatants from a T3SS1/T3SS2-deficient strain (RIMD2210633 vscN1 vscN2; (Hiyoshi et al., 2010)), which cannot secrete effectors for either T3SS, were labeled with Cy5 (green). Difference gel electrophoresis (DIGE) of supernatant-derived proteins from a T3SS1-deficient strain (RIMD2210633 vscN), and a T3SS1/T3SS2-deficient strain (RIMD2210633 vscN1 vscN2) was performed; differentially labeled samples were then electrophoresed together on a 2-D gel, and 30 red spots (putative T3SS2-dependent secreted proteins) were picked for identification with MALDI tandem mass spectrometry (data not shown). Twenty three spots were found to correspond to V. parahaemolyticus encoded proteins, and 19 of these matched with proteins encoded in T3SS2 (FIGS. 1A and 1B).

Furthermore, these T3SS2-encoded polypeptides (derived from 11 annotated proteins) included VopL, VopT, VopA, two effectors (VopV and VopC) reported to be secreted via T3SS2 after this study was initiated (Akeda et al., 2011; Hiyoshi et al., 2011), and VopD2 and VopW, components of the T3SS2 translocon (a portion of the secretion apparatus that is itself often secreted) (Kodama et al., 2008; Zhou et al., 2012b). This result indicates that DIGE is a powerful approach for identification of T3SS2-secreted proteins. Additional proteins from the T3SS2 gene cluster that were found to be secreted were Vpa1334 (VopcC), which is thought to function as the chaperone for VopC (Akeda et al., 2011), and VPA1336 (named here VopZ), VPA1350, and VPA1343; these latter three proteins are of unknown function. Secretion of VPA1336 and VPA1350 is also suggested by recent observations using a heterologous expression system (Zhou et al., 2012a). Three of the four non-T3SS2 encoded proteins present in the supernatant of T3SS1 mutant strains (VP0561, VP0994 and VP0715) appeared less likely to be effectors, based on their predicted functions. Finally, although the fourth non-T3SS2 encoded protein (VP0323) is annotated as an "immunogenic protein," further analyses revealed that it is secreted in a T3SS-independent manner (data not shown). Therefore, the investigators focused their efforts on investigating the roles of the 3 new T3SS2-secreted proteins identified (VPA1343, VopZ and VPA1350), since these were potential T3SS2 effectors.

VopZ (VPA1336) is translocated and is not required for secretion/translocation of other T3SS2 substrates Strains harboring mutations in vpa1343, vopZ or vpa1350 were examined to determine whether the strains were impaired for secretion of VopD2, a known T3SS2 substrate. Supernatants derived from a vpa1350 deletion mutant and from a vopZ mutant with a stop codon in amino acid 41 of the VPA1336 ORF (subsequently termed vopZ') contained similar amounts of VopD2 as the WT strain (FIG. 2A), indicating that neither VPA1350 nor VopZ are critical components of the T3SS2 secretion machinery. In contrast, supernatant from a vpa1343 deletion mutant did not contain detectable VopD2, despite the presence of this protein in cell pellets (FIG. 2A), indicating that VPA1343 is a component of the T3SS2 secretion apparatus or that the deletion had polar effects. Consistent with the former possibility, bioinformatic analysis according to Kelley and Sternberg, (2009) indicates that VPA1343 is a structural homolog of PrgI, the needle protein for the *Salmonella enteriditis* SPI-1 T3SS.

To test for VPA1350 or VopZ effects on T3SS2-mediated translocation, the secretion of known T3SS2 effector VopV was monitored from *V. parahaemolyticus* strains lacking either VPA1350 or VopZ. The translocated T3SS2 effector VopV was detected by immunofluorescence confocal microscopy in HeLa cells infected for one hour with the indicated *V. parahaemolyticus* strains. An anti-VopV antibody, rhodamine-phalloidin, and DAPI were used to visualize VopV, actin and nuclei respectively. Translocation of VopV into HeLa cells, which was visualized with confocal immunofluorescence microscopy, was detectable from a vscN1 vopZ' mutant, as well as from the positive control, a vscN1 mutant strain (data not shown). In contrast, similar to the vscN1 vscN2 mutant negative control, no VopV translocation was detectable from the vpa1350 deletion mutant (data not shown). The fact that VPA1350 is required for VopV transfer indicates that VPA1350 is not simply another effector for T3SS2, but instead may play a structural or regulatory role in the translocation process. The relative abundance of VPA1350 seen with DIGE is also consistent with its being a component of the secretion apparatus; structural proteins were in general significantly more abundant than were effectors (FIG. 1).

Like the initial DIGE analysis, western blot analyses indicate that endogenous and Cya-fusion VopZ is secreted in a T3SS2-dependent manner (data not shown). The p65 was visualized using immunofluorescence microscopy in HeLa cells that were infected (1 hr) with *V. parahaemolyticus*, then treated with TNFD (20 ng/ml). Furthermore, by measuring cAMP activity in Caco-2 cells infected by vscN1 or vscN1 vscN2 *V. parahaemolyticus* strains that produce effector-Cya (adenylate cyclase) fusion proteins, it was found that VopZ-Cya was translocated in a T3SS2-dependent fashion into this host cell line as efficiently as the known effector VopV (data not shown). Collectively, these experiments indicate that VopZ is a translocated protein that, like most T3 SS effectors, is not required for secretion or translocation of other T3SS2 substrates. Therefore, the study was focused on characterizing the effect of this translocated protein on host cells and during infection of infant rabbits.

VopZ Forms Punctae in HeLa Cells

To further characterize VopZ, the subcellular distribution of VopZ in host cells was first explored. The proteinVopZ (aa 38-62) is required for punctae formation in HeLa cells. HeLa cells were transfected with HA-tagged variants of VopZ, then treated with TNFα (20 ng/ml; 1 hr). N-terminally HA-tagged VopZ formed discrete punctae in HeLa cells (data not shown). Further transfection of a series of truncated vopZ derivatives indicated that amino acids 38 to 62 of VopZ are important for puncta formation (data not shown). In the absence of these amino acids (e.g. VopZΔ63-251 and VopZΔ38-62), VopZ distributed diffusely in the HeLa cell cytoplasm. Notably, this region of VopZ is highly conserved among VopZ homologs (which are all hypothetical, uncharacterized proteins), indicating that it may be important for VopZ function. Bioinformatic analysis of VopZ did not reveal the presence of any known motifs or significant similarities with known protein structures.

VopZ is Required for the T3SS2-Dependent Inhibition of IL-8 Secretion

Figure 3A:
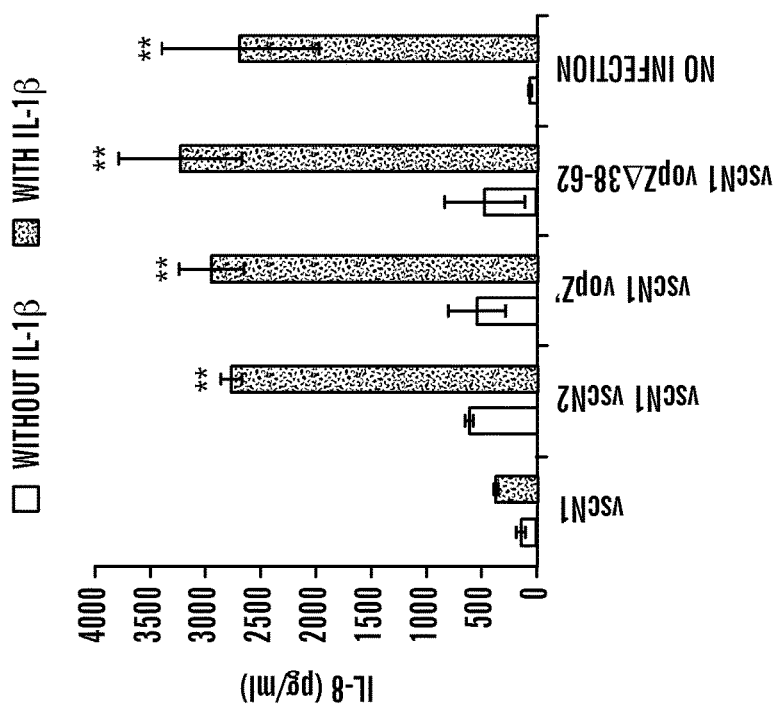
FIGS. 3A-3B shows that VopZ inhibits the release of IL-8 and the nuclear translocation of p65.
Figure 3B:
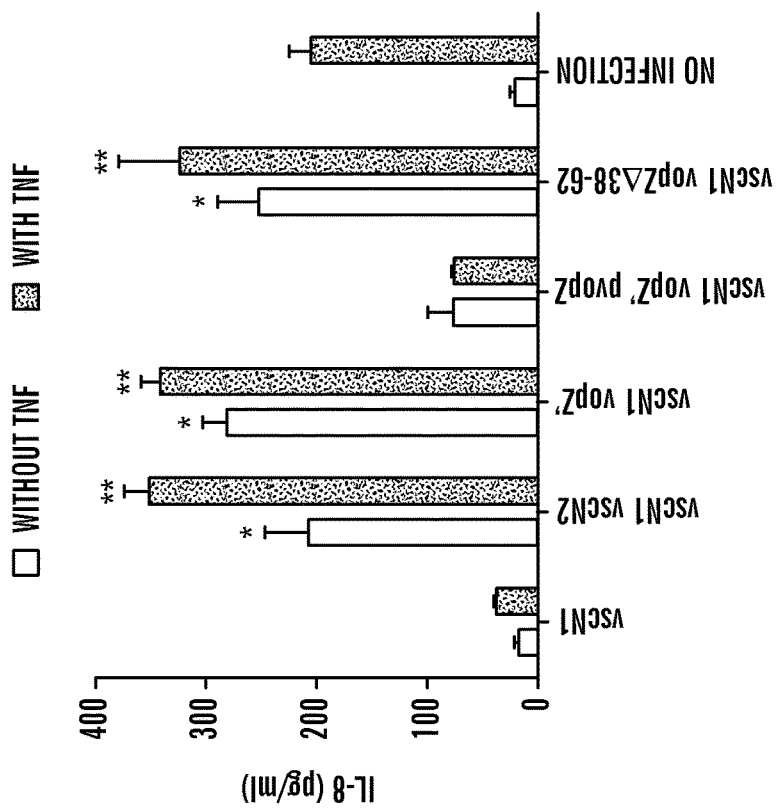

Previous investigations have shown that *V. parahaemolyticus*, unlike *V. cholerae*, elicits significant pro-inflammatory effects on host tissue, which appear to be partially dependent upon T3SS1 (Qadri et al., 2003; Matlawska-Wasowska et al., 2010; Shimohata et al., 2011). In contrast, some investigations indicate that T3SS2 dampens the host's innate immune response to *V. parahaemolyticus*; in particular, it limits production of IL-8 transcripts (Matlawska-Wasowska et al., 2010). IL-8 is a pro-inflammatory CXC chemokine that promotes neutrophil chemotaxis and degranulation. Therefore, whether VopZ modulates the production of IL-8 in HEK-293 and HeLa cells were explored. Experiments were performed with bacteria lacking vscN1, an integral component of T3SS1, as this system induces host cell cytotoxicity and lysis that complicates other analyses. As previously reported, it was found that T3SS2 suppresses IL-8 production in response to *V. parahaemolyticus* infection: a vscN1 vscN2 strain, in which both T3SS1 and T3SS2 are inactive, induced markedly more IL-8 secretion by HEK293 cells than did a vscN1 strain. Furthermore, this suppression appears to be entirely dependent upon VopZ, as the vscN1 vopZ' and vscN1 vscN2 mutants similarly induced IL-8 production (FIG. 3A). VopZ also blocks IL-8 up-regulation by HEK293 cells in response to TNFα, a potent stimulator of IL-8 production (via both NF-κB and MAPK pathways (see Hoffmann et al., 2002)) that is induced during infection of infant rabbits with *V. parahaemolyticus* (Ritchie et al., 2012). Co-culture of HEK293 cells with vscN1 bacteria markedly inhibited IL-8 induction following TNFα treatment, whereas co-culture with either the vscN1 vopZ' or the vscN1 vscN2 mutants did not (FIG. 3A). Furthermore, re-introduction of wild-type vopZ into the vscN1 vopZ' mutant reduced IL-8 levels, both in the presence and absence of TNFα, confirming that disruption of vopZ accounts for the phenotype of the vopZ mutant. VopZ also blocked IL-8 upregulation in HeLa cells in response to IL-1β (FIG. 3B), indicating that VopZ acts upon a shared component of the IL-1β and TNFα response pathways rather than a receptor-specific element. Finally, VopZ amino acids 38-62, which were important for punctae formation, also appear to be important for inhibition of IL-8 production, as IL-8 levels released into media from vscN1 vopZΔ38-62 and vscN1 vopZ'-infected cells were indistinguishable, in response to both TNFα and IL-1β (FIGS. 3A and 3B). These data raise the possibility that formation of VopZ punctae is linked to inhibition of IL-8 production.

VopZ Inhibits NF-κB Activation

To begin to define how VopZ inhibits IL-8 production, whether VopZ altered TNFα-induced translocation of the p65 (RelA) subunit of NF-κB into the nucleus was tested; the nuclear translocation of the p65 is necessary for canonical NF-κB pathway target gene induction. HeLa cells were infected with either vscN1, vscN1 vscN2, vscN1 vopZ, or vscN1 vopZΔ38-62 strains of V. parahaemolyticus for 1 hr (which is sufficient for T3SS2 effector translocation), and then stimulated by TNFα, a potent inducer of canonical NF-κB. P65 subcellular localization was determined by confocal immunofluorescence microscopy. Consistent with repression of an innate immune response by V. parahaemolyticus T3SS2, reduced TNFα-induced p65 nuclear translocation was observed in HeLa cells that were infected with vscN1 V. parahaemolyticus (nuclear p65 in 20% of infected cells vs. 78% of uninfected cells; data not shown), while translocation was largely not inhibited in HeLa cells infected with the vscN1 vscN2 mutant (data not shown; 53% of cells contained nuclear p65). As with IL-8 induction, suppression of TNFα-mediated p65 translocation was dependent upon VopZ, and in particular on VopZ amino acids 38-62 (data not shown; 44% and 40% nuclear p65, respectively, which is not statistically different from the 53% observed with the vscN1 vscN2 mutant). Transfected VopZ forms punctae in HeLa cells and prevents TNFα-dependent nuclear translocation of p65. HeLa cells were transfected with HA-tagged variants of VopZ, then treated (or not) with TNFα (20 ng/ml; 1 hr). VopZ inhibited p65 nuclear translocation to a similar extent in transfected HeLa cells. Thirty minutes following TNFα treatment, only 19% of VopZ transfected cells contained nuclear p65 compared to 78% of untransfected cells. (data not shown). Transfection of VopZΔ38-62 had minimal effect on p65 translocation (data not shown). These analyses indicate that VopZ inhibits IL-8 production at least in part by preventing p65 nuclear translocation.

Figure 4C:
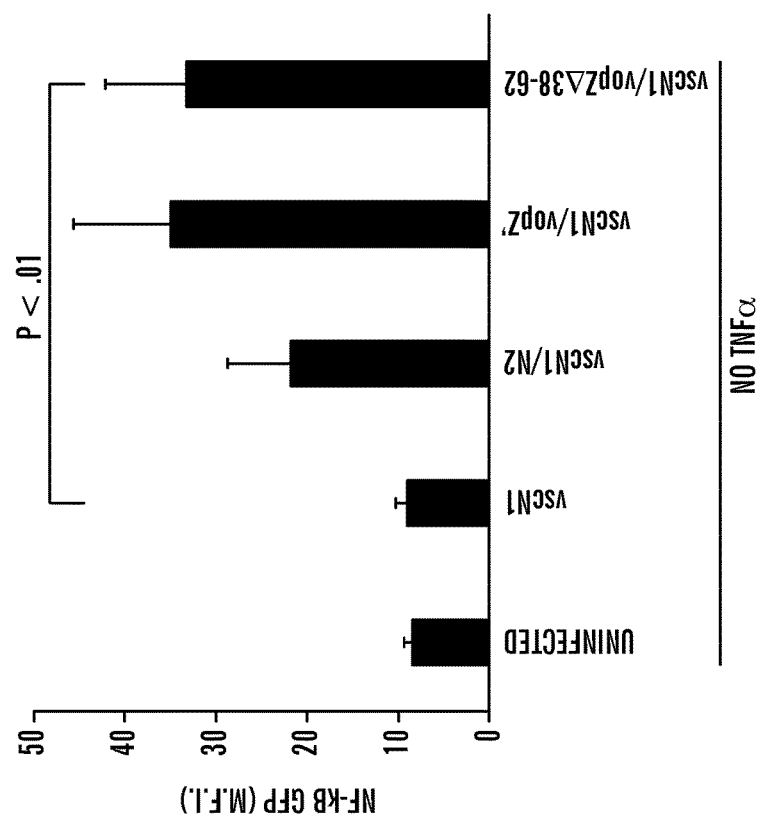

To further characterize VopZ's role as a bona-fide inhibitor of the canonical pathway for NF-κB activation, HEK293 cells with a stably integrated green fluorescent protein (GFP) NF-κB pathway reporter (Gewurz et al., 2011) was used for further studies. TNFα stimulation led to a marked increase in GFP expression in uninfected cells and in cells infected for 90 minutes prior to TNFα treatment with vscN1 vscN2, vscN1 vopZ' or vscN1 vopZΔ38-62 strains. In contrast, cells infected with the vscN1 strain exhibited significantly lower NF-κB GFP reporter intensity in response to TNFα treatment (FIGS. 4A and 4B). As noted above for IL-8 induction, V. parahaemolyticus strains that lack intact VopZ induced NF-κB reporter activation even in the absence of TNFα stimulation. However, VopZ completely blocked V. parahaemolyticus-induced NF-κB activation (FIG. 4C). The results obtained here indicate that VopZ is required for V. parahaemolyticus T3SS2-mediated inhibition of NF-κB activity, and that this inhibition is dependent at least in part on VopZ amino acids 38-62.

Figure 5A:
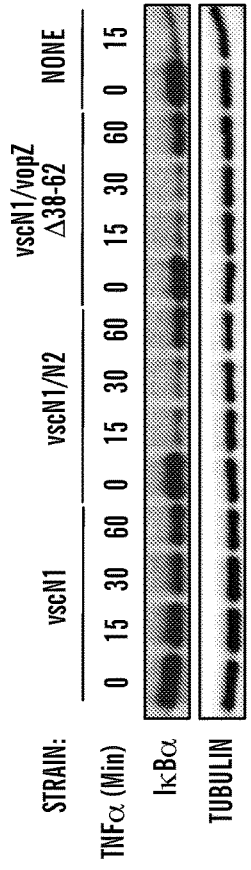
FIGS. 5A-5C show that VopZ inhibits canonical NF-κB but not non-canonical NF-κB pathway activation.
Figure 5B:
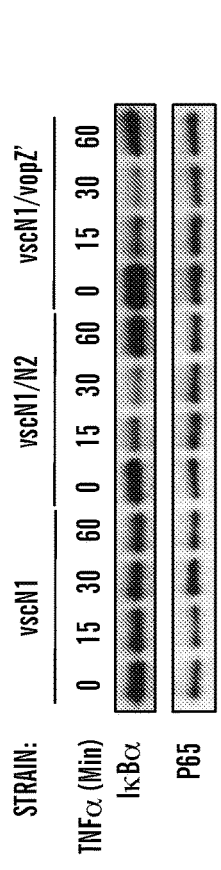

VopZ blocks canonical NF-κB activation at or above the level of IκBα degradation. To further characterize VopZ blockade of TNFα-induced p65 nuclear translocation, further experiment was performed to determine whether V. parahaemolyticus inhibits TNFα-mediated IκBα degradation. Following 90 minutes of infection with V. parahaemolyticus strains, HEK293 cells were treated with TNFα. IκBα was rapidly degraded in response to TNFα treatment in cells infected with vscN1 vscN2, vscN1 vopZ' or vscN1 vopZΔ38-62 strains, as well as in uninfected cells (FIGS. 5A and 5B). In contrast, infection with the vscN1 mutant markedly stabilized IκBα in the presence of TNFα. These results indicate that VopZ blocks TNFα-mediated canonical NF-κB activation at or above the level of IκBα degradation, and that this effect requires VopZ residues 38-62.

VopZ Inhibits MAPK Pathway Activation

Figures 6A, 6B:
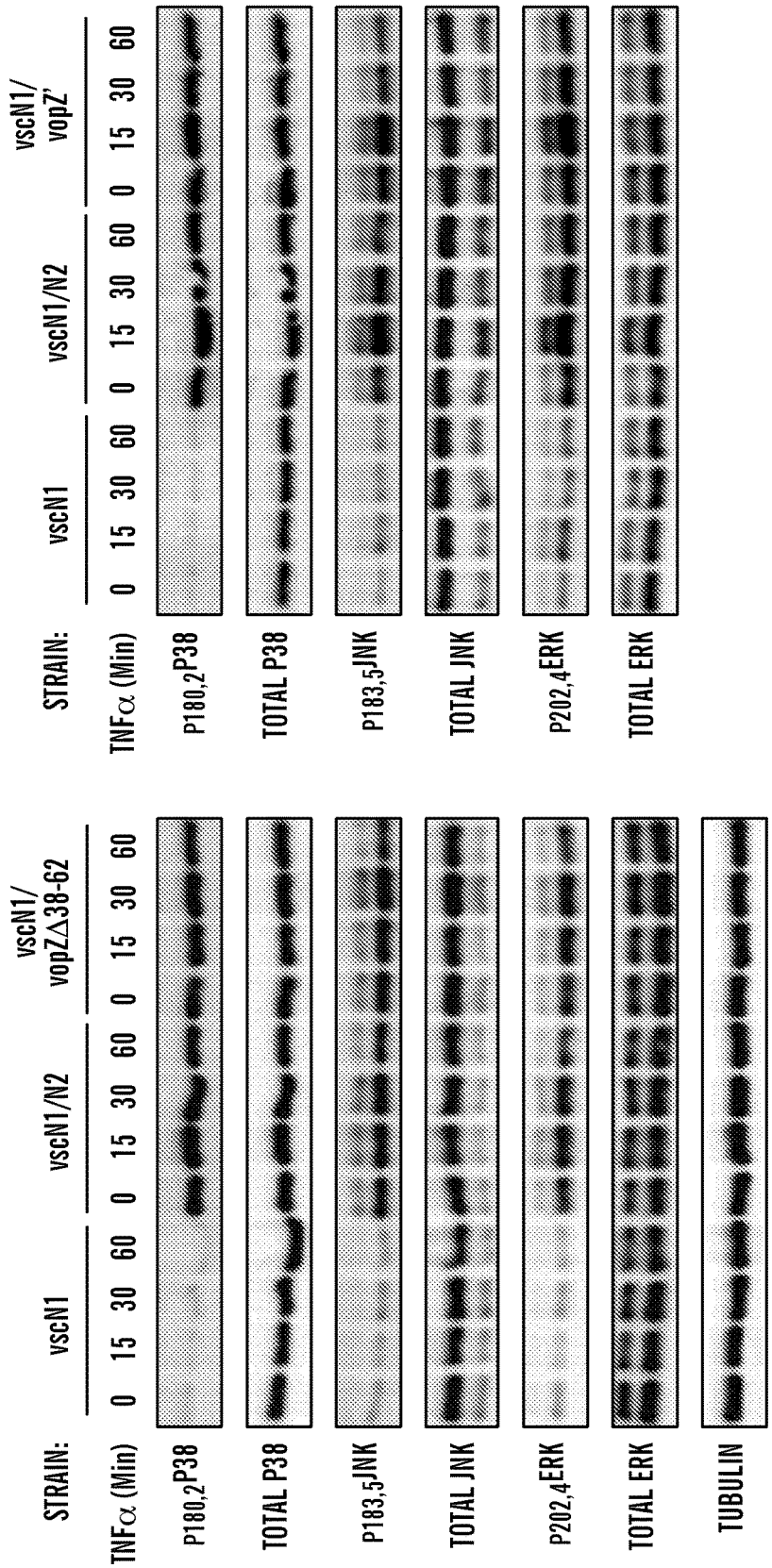
FIGS. 6A-6C. VopZ inhibits MAPK pathway activation.
Figure 6C:
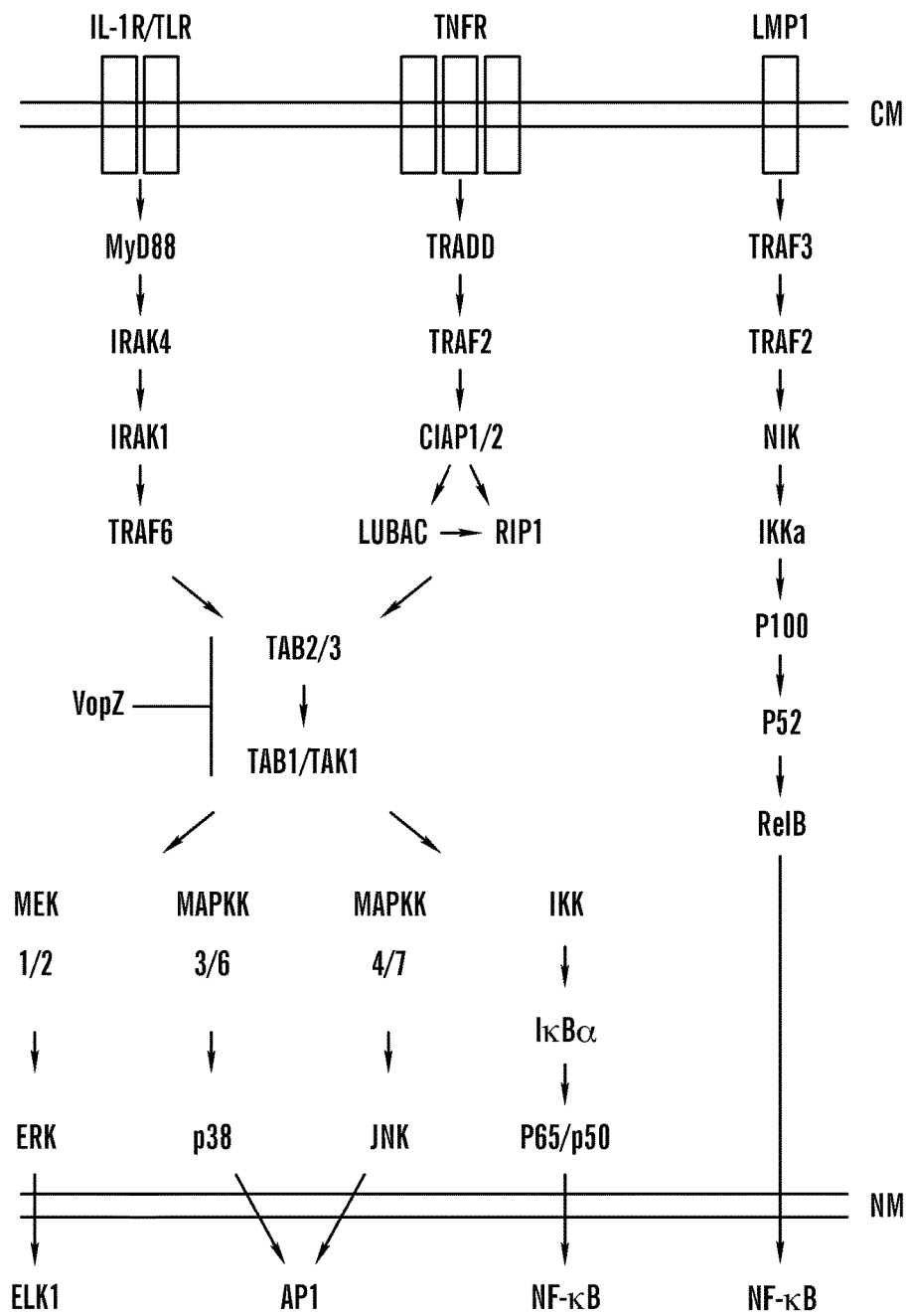

The p38, JNK and ERK MAPK pathways are also key regulators of innate immune responses to bacterial pathogens. Indeed, many innate immune receptors, including Toll receptors, concurrently activate both canonical NF-κB and MAPK pathways through activation of the kinase MAP3K7 (also known as TAK1). Following TAK1 activation, the MAPK and NF-κB signal transduction pathways diverge. To test whether V. parahaemolyticus impairs innate immune signaling at or above the level of TAK1, it was determined whether VopZ also inhibits these MAPK pathways. Following infection with V. parahaemolyticus strains, HEK293 cells were again stimulated with TNFα, and p38, JNK and ERK pathway activation was measured using MAPK phospho-specific antibodies. ERK, JNK and p38 activation loop phosphorylation, which provides a readout of their activation state, was strongly inhibited in cells infected with the vscN1 mutant, but not upon infection with strains that lack VopZ (vscN1 vscN2 or vscN1 vopZ' strains) (FIGS. 6A and 6B). Infection of HEK293 cells with V. parahaemolyticus did not alter the total cell levels of the three MAPK (FIGS. 6A and 6B). However, infection with V. parahaemolyticus strains that lack VopZ triggered MAPK phosphorylation even prior to TNFα stimulation, indicating that VopZ can block multiple pathways that activate MAPKs. As seen for NF-κB regulation, deletion of VopZ residues 38-62 abolished the ability of V. parahaemolyticus to inhibit MAPK activation. Collectively these observations are consistent with VopZ acting upon a regulatory factor that targets both NF-κB and MAPK pathways.

Figure 5C:
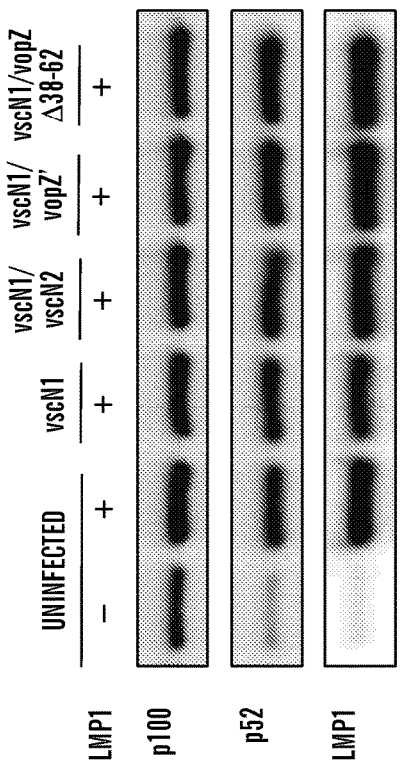

V. parahaemolyticus Infection does not Inhibit Non-Canonical NF-κB Pathway Activation Experiments were conducted to examined whether VopZ likewise blocks non-canonical NF-κB pathway activation; experiments used HEK293 cells that inducibly express Epstein Barr virus Latent Membrane Protein 1 (LMP1), a potent activator of the non-canonical NF-κB pathway (Luftig et al., 2004). LMP1 expression was induced in cells infected with V. parahaemolyticus strains, and then Western blotting was used to assess the ratio of the p100 precursor to the p52 active transcription factor, a commonly used hallmark of non-canonical NF-κB activation. It was found that LMP1 efficiently triggered p52 production both in the absence and presence of VopZ (FIG. 5C). Thus, induction of the non-canonical NF-κB pathway, which unlike the other surveyed pathways is independent of the TAK1 complex, does not appear to be subject to regulation by VopZ.

VopZ Contributes to *V. parahaemolyticus* Intestinal Colonization and Disease in Infant Rabbits Infant rabbit model of *V. parahaemolyticus* infection were used to explore whether VopZ was important for the pathogen to colonize the small intestine and/or cause disease. Strikingly, truncation of VopZ (i.e., vopZ') reduced intestinal colonization, diarrhea/fluid accumulation and intestinal pathology nearly to the same extent as did inactivation of the entire T3 SS2 (via deletion of vscN2) (FIG. 7), even though this vitro analyses indicates that T3SS2 is fully functional in a vopZ' background. Thus, VopZ is a critically important virulence factor.

Figure 7B:
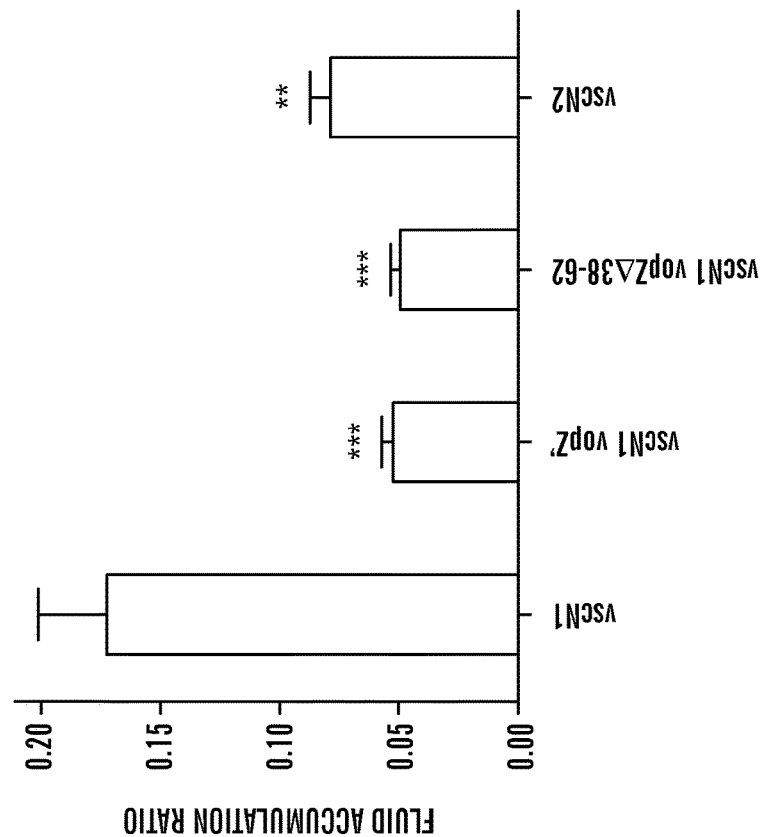
FIGS. 7A-7E show that VopZ makes distinct and genetically separable contributions to *V. parahaemolyticus* colonization and pathogenesis within the infant rabbit small intestine.
Figure 7A:
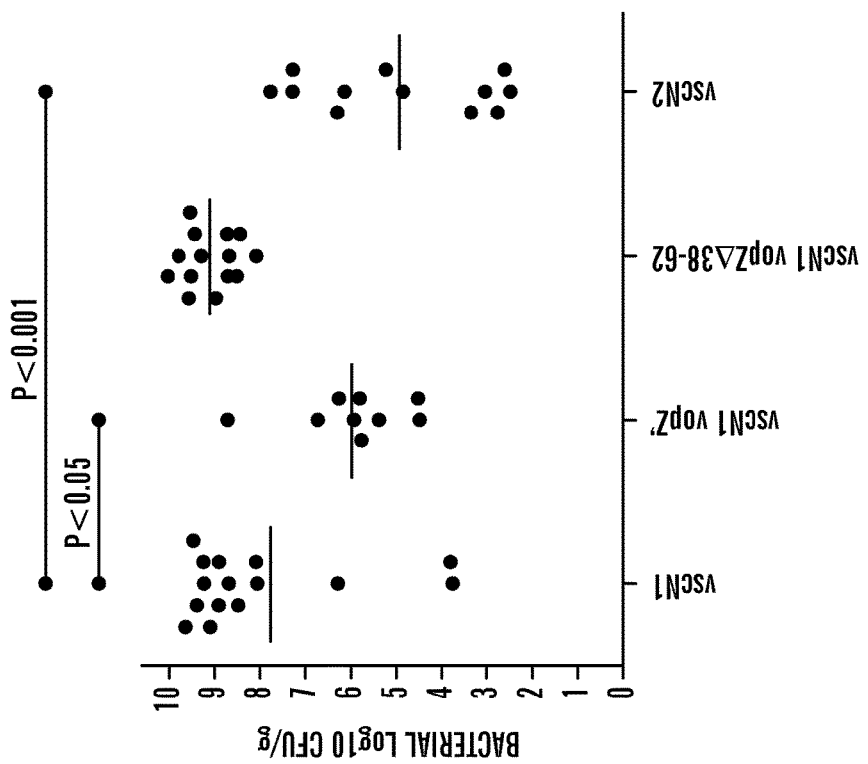
Figure 7C:
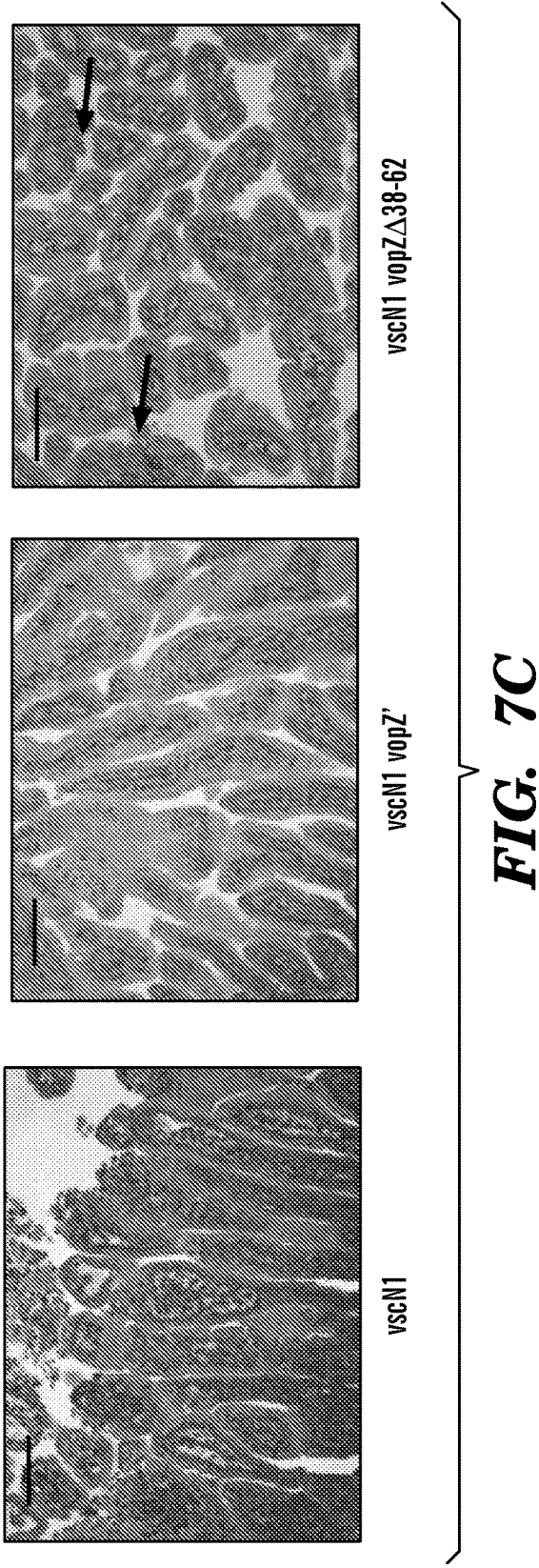
Figure 7E:
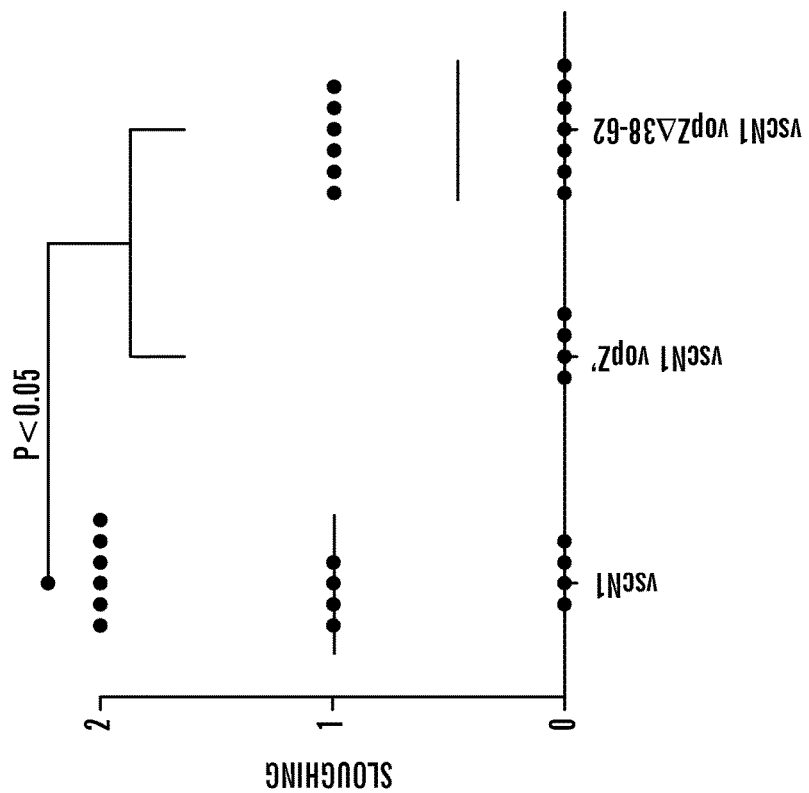
Figure 7D:
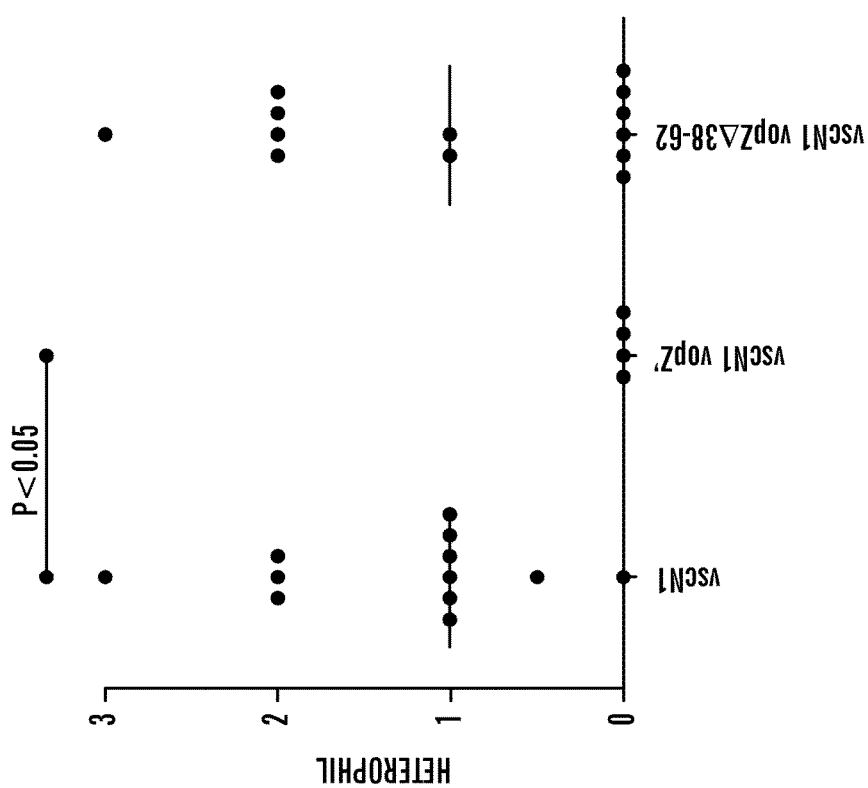

Interestingly, unlike for all other assays described above, the effects in infant rabbits of the vopZ' and vopZΔ38-62 mutations were not equal. The absence of VopZ aa 38-62, unlike VopZ truncation, did not interfere with the capacity of *V. parahaemolyticus* to colonize the infant rabbit intestinal tract (FIG. 7A), nor did it reduce heterophil infiltration (FIG. 7D). However, the vopZ internal deletion did have a comparable effect to vopZ truncation (and vscN2 deletion) on diarrhea and intestinal fluid accumulation (FIG. 7B); rabbits lacked all gross manifestations of infection despite robust colonization. Additionally, it markedly reduced the epithelial disruption typically observed in response to *V. parahaemolyticus* (FIG. 7C), which can be quantified in part as a reduction in cell sloughing (FIG. 7E). Thus, WT VopZ is critically important for development of at least some aspects of intestinal pathology caused by *V. parahaemolyticus* infection; the diarrhea and extensive tissue disruption that characterize infection are largely dependent upon this effector, rather than being an unavoidable consequence of colonization by *V. parahaemolyticus*. The fact that VopZ's contributions to colonization and intestinal pathology are genetically separable suggests that VopZ plays distinct roles in each process and is a multifunctional T3SS2 effector.

CONCLUSION

Previous studies using animal models of *V. parahaemolyticus* pathogenicity have revealed that T3SS2 is critical for this pathogen to colonize the intestine and to cause disease (Park et al., 2004; Hiyoshi et al., 2010; Piñeyro et al., 2010; Ritchie et al., 2012). Here, the inventors found that VopA, VopT, and VopL, the 3 T3SS2-secreted effectors known when this work was initiated ± are not required by *V. parahaemolyticus* to colonize the infant rabbit intestine or induce disease. Additionally, the inventors identified 3 previously unreported T3SS2-secreted proteins, two of which (VPA1343 and VPA1350) are likely to be components of the secretion/translocation apparatus. The third new protein, VopZ (VPA1336), is an uncharacterized T3SS2-encoded/secreted polypeptide with no recognizable functional domains. The inventors confirmed that VopZ, unlike VopA, VopT, and VopL, is an essential virulence factor. Furthermore, VopZ appears to play distinct, genetically separable roles in enabling *V. parahaemolyticus* to colonize the intestine and to cause diarrhea. Deletion of VopZ aa 38-62 abrogated *V. parahaemolyticus*-induced diarrhea and reduced fluid accumulation in the small intestine as well as some histopathologic signs of disease; however, it did not impair *V. parahaemolyticus*' capacity to colonize the small intestine. In contrast, truncation of VopZ prevented *V. parahaemolyticus* colonization as well as all signs of disease. Thus, VopZ is required for colonization but also makes an additional contribution to disease pathology. In vitro, VopZ blocked activation of NF-κB and three MAPK pathways, key components of the innate immune signaling pathways that promote the production of IL-8 and other cytokines, and this effect was also dependent upon aa38-62. Taken together, the observations indicate that inhibition of signaling pathways that mediate innate immunity is critical for *V. parahaemolyticus* pathogenicity.

The references cited herein and throughout the specification are incorporated herein by reference.

REFERENCES

Akeda, Y., Kodama, T., Saito, K., Iida, T., Oishi, K., and Honda, T. (2011). Identification of the *Vibrio parahaemolyticus* type III secretion system 2-associated chaperone VocC for the T3SS2-specific effector VopC. FEMS Microbiology Letters 324, 156-164.

Baldwin, A. S. (2012). Regulation of cell death and autophagy by IKK and NF-kB: critical mechanisms in immune function and cancer. Immunological Reviews 246, 327-345.

Bhattacharjee, R. N., Park, K.-S., Kumagai, Y., Okada, K., Yamamoto, M., Uematsu, S., Matsui, K., Kumar, H., Kawai, T., Iida, T., et al. (2006). VP1686, a *Vibrio* type III secretion protein, induces toll-¬like receptor-¬independent apoptosis in macrophage through NF-kappaB inhibition. J. Biol. Chem. 281, 36897-36904.

Broberg, C. A., Calder, T. J., and Orth, K. (2011). *Vibrio parahaemolyticus* cell biology and pathogenicity determinants Microbes Infect.

Bruno, V. M., Hannemann, S., Lara-Tejero, M., Flavell, R. A., Kleinstein, S. H., and Galán, J. E. (2009). *Salmonella Typhimurium* Type III Secretion Effectors Stimulate Innate Immune Responses in Cultured Epithelial Cells. PLoS Pathog 5, e1000538.

Burdette, D. L., Yarbrough, M. L., and Orth, K. (2009). Not without cause: *Vibrio parahaemolyticus* induces acute autophagy and cell death. Autophagy 5, 100-102.

Burdette, D. L., Yarbrough, M. L., Orvedahl, A., Gilpin, C. J., and Orth, K. (2008). *Vibrio parahaemolyticus* orchestrates a multifaceted host cell infection by induction of autophagy, cell rounding, and then cell lysis. Proc. Natl. Acad. Sci. U.S.A. 105, 12497-12502.

Coburn, B., Sekirov, I., and Finlay, B. B. (2007). Type III Secretion Systems and Disease. Clinical Microbiology Reviews 20, 535-549.

Cornelis, G. R. (2006). The type III secretion injectisome. Nat Rev Micro 4, 811-825.

Dean, P. (2011). Functional domains and motifs of bacterial type III effector proteins and their roles in infection. FEMS Microbiology Reviews 35, 1100-1125.

Galán, J. E. (2009). Common Themes in the Design and Function of Bacterial Effectors. Cell Host Microbe 5, 571-579.

Gewurz, B. E., Mar, J. C., Padi, M., Zhao, B., Shinners, N. P., Takasaki, K., Bedoya, E., Zou, J. Y., Cahir-Mcfarland, E., Quackenbush, J., et al. (2011). Canonical NF-¬B Activation Is Essential for Epstein-¬Barr Virus Latent Membrane Protein 1 TES2/CTAR2 Gene Regulation. Journal of Virology 85, 6764-6773.

Gewurz, B. E., Towfic, F., Mar, J. C., Shinners, N. P., Takasaki, K., Zhao, B., Cahir-McFarland, E. D., Quackenbush, J., Xavier, R. J., and Kieff, E. (2012). Genome-wide siRNA screen for mediators of NF-κB activation. Proceedings of the National Academy of Sciences 109, 2467-2472.

Hayden, M. S., and Ghosh, S. (2011). NF-κB in immunobiology. Cell Res. 21, 223-244.

Hiyoshi, H., Kodama, T., Iida, T., and Honda, T. (2010). Contribution of *Vibrio parahaemolyticus* Virulence Factors to Cytotoxicity, Enterotoxicity, and Lethality in Mice. Infect. Immun 78, 1772-1780.

Hiyoshi, H., Kodama, T., Saito, K., Gotoh, K., Matsuda, S., Akeda, Y., Honda, T., and Iida, T. (2011). VopV, an F-Actin-Binding Type III Secretion Effector, Is Required for *Vibrio parahaemolyticus*-Induced Enterotoxicity. Cell Host Microbe 10, 401-409.

Hoffmann, E., Dittrich-Breiholz, O., Holtmann, H., and Kracht, M. (2002). Multiple control of interleukin-8 gene expression. J. Leukoc. Biol. 72, 847-855.

Iwai, K. (2012). Diverse ubiquitin signaling in NF-κB activation. Trends in Cell Biology 22, 355-364.

Kelley, L. A., and Sternberg, M. J. E. (2009). Protein structure prediction on the Web: a case study using the Phyre server. Nat Protoc 4, 363-371.

Kim, M., Ashida, H., Ogawa, M., Yoshikawa, Y., Mimuro, H., and Sasakawa, C. (2010). Bacterial Interactions with the Host Epithelium. Cell Host Microbe 8, 20-35.

Kodama, T., Hiyoshi, H., Gotoh, K., Akeda, Y., Matsuda, S., Park, K. S., Cantarelli, V. V., Iida, T., and Honda, T. (2008). Identification of Two Translocon Proteins of *Vibrio parahaemolyticus* Type III Secretion System 2. Infect. Immun. 76, 4282-4289.

Kodama, T., Rokuda, M., Park, K.-¬S., Cantarelli, V. V., Matsuda, S., Iida, T., and Honda, T. (2007). Identification and characterization of VopT, a novel ADP-ribosyltransferase effector protein secreted via the *Vibrio parahaemolyticus* type III secretion system 2. Cell. Microbiol. 9, 2598-2609.

Kumamoto, C. A. (2011). Inflammation and gastrointestinal *Candida* colonization. Curr. Opin. Microbiol. 14, 386-391.

Liverman, A. D. B., Cheng, H.-¬C., Trosky, J. E., Leung, D. W., Yarbrough, M. L., Burdette, D. L., Rosen, M. K., and Orth, K. (2007). Arp2/3-independent assembly of actin by *Vibrio* type III effector VopL. Proc. Natl. Acad. Sci. U.S.A. 104, 17117-17122.

Luftig, M., Yasui, T., Soni, V., Kang, M.¬S., Jacobson, N., Cahir-McFarland, E., Seed, B., and Kieff, E. (2004). Epstein-¬Barr virus latent infection membrane protein 1 TRAF-binding site induces NIK/IKK alpha-dependent non-canonical NF-kappaB activation. Proc. Natl. Acad. Sci. U.S.a. 101, 141-146.

Makino, K., Oshima, K., Kurokawa, K., Yokoyama, K., Uda, T., Tagomori, K., Iijima, Y., Najima, M., Nakano, M., Yamashita, A., et al. (2003). Genome sequence of *Vibrio parahaemolyticus*: a pathogenic mechanism distinct from that of *V. cholerae*. Lancet 361, 743-749.

Matlawska-Wasowska, K., Finn, R., Mustel, A., O'Byrne, C. P., Baird, A. W., Coffey, E. T., and Boyd, A. (2010). The *Vibrio parahaemolyticus* Type III Secretion Systems manipulate host cell MAPK for critical steps in pathogenesis. BMC Microbiol. 10, 329.

Mittal, R., Peak-Chew, S.-Y., and McMahon, H. T. (2006). Acetylation of MEK2 and I kappa B kinase (IKK) activation loop residues by YopJ inhibits signaling. Proc. Natl. Acad. Sci. U.S.a. 103, 18574-18579.

Morales, V. M., Backman, A., and Bagdasarian, M. (1991). A series of wide-hos range low copy number vectors that allow direct screening for recombinants Gene 97, 39-47.

Mukherjee, S., Keitany, G., Li, Y., Wang, Y., Ball, H. L., Goldsmith, E. J., and Orth, K. (2006). *Yersinia* YopJ acetylates and inhibits kinase activation by blocking phosphorylation. Science 312, 1211-1214.

Nadler, C., Baruch, K., Kobi, S., Mills, E., Haviv, G., Farago, M., Alkalay, I., Bartfeld, S., Meyer, T. F., Ben-Neriah, Y., et al. (2010). The Type III Secretion Effector NleE Inhibits NF-κB Activation. PLoS Pathog 6, e1000743.

Neish, A. S., and Naumann, M. (2011). Microbial-induced immunomodulation by targeting the NF-KB system. Trends in Microbiology 19, 596-605.

Paquette, N., Conlon, J., Sweet, C., Rus, F., Wilson, L., Pereira, A., Rosadini, C. V., Goutagny, N., Weber, A. N. R., Lane, W. S., et al. (2012). Serine/threonine acetylation of TGF-activated kinase (TAK1) by *Yersinia pestis* YopJ inhibits innate immune signaling. Proceedings of the National Academy of Sciences 109, 12710-12715.

Park, K.-¬S., Ono, T., Rokuda, M., Jang, M.-H., Okada, K., Iida, T., and Honda, T. (2004). Functional characterization of two type III secretion systems of *Vibrio parahaemolyticus*. Infect. Immun. 72, 6659±6665.

Piñeyro, P., Zhou, X., Orfe, L. H., Friel, P. J., Lahmers, K., and Call, D. R. (2010). Development of two animal models to study the function of *Vibrio parahaemolyticus* type III secretion systems. Infect. Immun. 78, 4551-4559.

Qadri, F., Alam, M. S., Nishibuchi, M., Rahman, T., Alam, N. H., Chisti, J., Kondo, S., Sugiyama, J., Bhuiyan, N. A., Mathan, M. M., et al. (2003). Adaptive and inflammatory immune responses in patients infected with strains of *Vibrio parahaemolyticus*. J. Infect. Dis. 187, 1085-1096.

Ritchie, J. M., Rui, H., Zhou, X., Iida, T., Kodoma, T., Ito, S., Davis, B. M., Bronson, R. T., and Waldor, M. K. (2012). Inflammation and Disintegration of Intestinal Villi in an Experimental Model for *Vibrio parahaemolyticus*-Induced Diarrhea. PLoS Pathog 8, e1002593.

Ritchie, J. M., Thorpe, C. M., Rogers, A. B., and Waldor, M. K. (2003). Critical roles for stx2, eae, and tir in enterohemorrhagic *Escherichia coli*-induced diarrhea and intestinal inflammation in infant rabbits. Infect. Immun. 71, 7129-7139.

Rüssmann, H., Shams, H., Poblete, F., Fu, Y., Galan, J. E., and Donis, R. O. (1998). Delivery of epitopes by the *Salmonella* type III secretion system for vaccine development. Science 281, 565-568.

Sakurai, H. (2012). Targeting of TAK1 in inflammatory disorders and cancer. Trends in Pharmacological Sciences.

Shimohata, T., and Takahashi, A. (2010). Diarrhea induced by infection of *Vibrio parahaemolyticus*. J. Med. Invest. 57, 179-182.

Shimohata, T., Nakano, M., Lian, X., Shigeyama, T., Iba, H., Hamamoto, A., Yoshida, M., Harada, N., Yamamoto, H., Yamato, M., et al. (2011). *Vibrio parahaemolyticus* Infection Induces Modulation of IL-8 Secretion Through Dual Pathway via VP1680 in Caco-2 Cells. Journal of Infectious Diseases 203, 537-544.

Stecher, B., Robbiani, R., Walker, A. W., Westendorf, A. M., Barthel, M., Kremer, M., Chaffron, S., Macpherson, A. J., Buer, J., Parkhill, J., et al. (2007). *Salmonella enterica Serovar Typhimurium* Exploits Inflammation to Compete with the Intestinal Microbiota. Plos Biol 5, e244.

Su, Y.-C., and Liu, C. (2007). *Vibrio parahaemolyticus*: a concern of seafood safety. Food Microbiol. 24, 549-558.

Sun, S.-C. (2011). Non-canonical NF-κB signaling pathway. Cell Res. 21, 71-85.

Thiefes, A., Wolf, A., Doerrie, A., A Grassl, G., Matsumoto, K., Autenrieth, I., Bohn, E., Sakurai, H., Niedenthal, R., Resch, K., et al. (2006). The *Yersinia enterocolitica* effector YopP inhibits host cell signalling by inactivating the protein kinase TAK1 in the IL-1 signalling pathway. EMBO Rep.

Trosky, J. E., Li, Y., Mukherjee, S., Keitany, G., Ball, H., and Orth, K. (2007). VopA inhibits ATP binding by acetylating the catalytic loop of MAPK kinases. J. Biol. Chem. 282, 34299-34305.

Trosky, J. E., Mukherjee, S., Burdette, D. L., Roberts, M., McCarter, L., Siegel, R. M., and Orth, K. (2004). Inhibition of MAPK signaling pathways by VopA from *Vibrio parahaemolyticus*. J. Biol. Chem. 279, 51953-51957.

Zhou, X., Konkel, M. E., and Call, D. R. (2010). Vp1659 Is a *Vibrio parahaemolyticus* Type III Secretion System 1 Protein That Contributes to Translocation of Effector Proteins Needed To Induce Cytolysis, Autophagy, and Disruption of Actin Structure in HeLa Cells. J. Bacteriol. 192, 3491-3502.

Zhou, X., Nydam, S. D., Christensen, J. E., Konkel, M. E., Orfe, L., Friel, P., and Call, D. R. (2012a). Identification of Potential Type III Secretion Proteins via Heterologous Expression of *Vibrio parahaemolyticus* DNA. Applied and Environmental Microbiology 78, 3492-3494.

Zhou, X., Ritchie, J. M., Hiyoshi, H., Iida, T., Davis, B. M., Waldor, M. K., and Kodama, T. (2012b). The Hydrophilic Translocator for *Vibrio parahaemolyticus*, T3SS2, Is Also Translocated. Infect. Immun. 80, 2940-2947.

Zhou, X., Shah, D. H., Konkel, M. E., and Call, D. R. (2008). Type III secretion system 1 genes in *Vibrio parahaemolyticus* are positively regulated by ExsA and negatively regulated by ExsD. Mol. Microbiol. 69, 747-764.

---

What is claimed:

1. A method comprising administering to a host subject a composition comprising an isolated live attenuated bacterium comprising a nucleic acid encoding a mutant VopZ protein that lacks at least the amino acid residues 38-62 of SEQ. ID. NO:1, wherein the attenuated bacterium does not cause diarrhea normally associated with *Vibro parahaemolyticus* in the host subject.

* * * * *

SEQUENCE LISTING

<160> NUMBER OF SEQ ID NOS: 11

<210> SEQ ID NO 1
<211> LENGTH: 250
<212> TYPE: PRT
<213> ORGANISM: Vibrio parahaemolyticus

<400> SEQUENCE: 1

```
Met Ser Asn Ile Asn Asn Ser Val Ser Leu Phe Ile Arg Asp Thr Val
1               5                   10                  15

Asp Gly Glu Phe Asp Lys Ala Thr Ser Lys Gln Ser Asn Thr Asp Asp
            20                  25                  30

Asp Phe Ser Lys Ile Leu Asn Gln Met Ser Lys Val Glu Ser Arg Asp
        35                  40                  45

Ile Asp Leu Ser Phe Val Leu Asp Gln Glu Glu Glu Asp Glu Asp Glu
    50                  55                  60

Glu Cys Asp Thr Glu Leu Leu Gln Asn Thr Arg Ser Ile Glu Ser Val
65                  70                  75                  80

Lys Glu Arg Gly Leu Leu Asn Phe Leu Phe Arg His Pro Thr Lys Asn
                85                  90                  95

Val Tyr Ile Arg Pro Thr Asn Lys Lys Arg Asp Ile Glu Gln Asn Glu
            100                 105                 110

Ile Val Leu Thr Leu Gln Tyr Gln Gln Ser Asn Tyr Asn Phe Lys Trp
        115                 120                 125

Arg Lys Ile Glu Ile Glu Gly Val Lys Val Arg Leu Glu Lys Asn Thr
    130                 135                 140

Pro Gly Leu Arg Val Phe Asn Ser Leu His Phe Asp Asn Asn Asn Phe
145                 150                 155                 160

Val Ser Ile Ile Asp Glu Lys Ile Tyr Ser Lys Asn Asn Glu Phe Ala
                165                 170                 175

Tyr Leu Ser Ser Asp Phe Lys Lys Tyr Ile Asn Val Glu Asn Tyr Thr
            180                 185                 190

Arg Ser Ile Ala Ile Pro Leu Ala Ser Thr Met Ser Phe Asp Leu Ser
        195                 200                 205

Val Asn Tyr Phe Asn Gln Ile Asn Thr Leu Asn Lys Tyr Arg Val Leu
    210                 215                 220

Tyr Lys Lys Tyr Tyr Ile Phe Glu Phe Glu Asn Gly Lys Leu Val
225                 230                 235                 240

Asn Phe Met Arg Gly Tyr Asn Asp Gly Tyr
                245                 250
```

<210> SEQ ID NO 2
<211> LENGTH: 753
<212> TYPE: DNA
<213> ORGANISM: Vibrio parahaemolyticus

<400> SEQUENCE: 2

```
atgagcaaca ttaataattc tgtatcgcta ttcattcgag atacggtaga cggtgaattt      60
gataaagcaa cctctaaaca atctaatact gatgatgact tctctaaaat tctgaatcaa     120
atgagtaaag tcgagagcag agacattgat cttagctttg tacttgatca ggaagaagag     180
gatgaggatg aggagtgtga tacagaatta ttgcagaata cacgaagtat tgaatcggtt     240
aaagaaaggg gtttattaaa tttttattc cgtcatccta cgaaaaatgt ctatatcaga      300
cctaccaata aaaacgcga tattgagcaa aacgagatta ttctgacgct gcagtatcag     360
caatcgaatt ataatttaa gtggagaaag attgagatag agggggtgaa agttagatta     420
gaaaaaaata ctcctggact tagagtattc aattctcttc actttgataa taataatttt     480
gttagcataa tagatgaaaa aatatattca aaaaataatg aattcgcgta tttgagtagt     540
gattttaaaa aatatataaa cgtagagaac tatacaagaa gtatagctat cccctagct      600
agtacgatga gttttgatct ttctgtaaat tattttaatc aaatcaatac cttgaataag     660
taccgagtgt tatataagaa aaaatattat atatttgaat ttgaaaatgg aaaattagtt     720
aattttatgc gaggttataa tgacggttat tga                                   753
```

<210> SEQ ID NO 3
<211> LENGTH: 225
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Ser Asn Ile Asn Asn Ser Val Ser Leu Phe Ile Arg Asp Thr Val
1               5                   10                  15

Asp Gly Glu Phe Asp Lys Ala Thr Ser Lys Gln Ser Asn Thr Asp Asp
            20                  25                  30

Asp Phe Ser Lys Ile Asp Glu Glu Cys Asp Thr Glu Leu Leu Gln Asn
        35                  40                  45

Thr Arg Ser Ile Glu Ser Val Lys Glu Arg Gly Leu Leu Asn Phe Leu
    50                  55                  60

Phe Arg His Pro Thr Lys Asn Val Tyr Ile Arg Pro Thr Asn Lys Lys
65                  70                  75                  80

Arg Asp Ile Glu Gln Asn Glu Ile Val Leu Thr Leu Gln Tyr Gln Gln
                85                  90                  95

Ser Asn Tyr Asn Phe Lys Trp Arg Lys Ile Glu Ile Glu Gly Val Lys
            100                 105                 110

Val Arg Leu Glu Lys Asn Thr Pro Gly Leu Arg Val Phe Asn Ser Leu
        115                 120                 125

His Phe Asp Asn Asn Phe Val Ser Ile Ile Asp Glu Lys Ile Tyr
    130                 135                 140

Ser Lys Asn Asn Glu Phe Ala Tyr Leu Ser Ser Asp Phe Lys Lys Tyr
145                 150                 155                 160

Ile Asn Val Glu Asn Tyr Thr Arg Ser Ile Ala Ile Pro Leu Ala Ser
                165                 170                 175
```

Thr Met Ser Phe Asp Leu Ser Val Asn Tyr Phe Asn Gln Ile Asn Thr
            180                 185                 190

Leu Asn Lys Tyr Arg Val Leu Tyr Lys Lys Tyr Tyr Ile Phe Glu
        195                 200                 205

Phe Glu Asn Gly Lys Leu Val Asn Phe Met Arg Gly Tyr Asn Asp Gly
    210                 215                 220

Tyr
225

<210> SEQ ID NO 4
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgagcaaca ttaataattc tgtatcgcta ttcattcgag atacggtaga cggtgaattt    60
gataaagcaa cctctaaaca atctaatact gatgatgact tctctaaaat tgatgaggag   120
tgtgatacag aattattgca gaatacacga agtattgaat cggttaaaga aaggggttta   180
ttaaattttt tattccgtca tcctacgaaa aatgtctata tcagacctac caataaaaaa   240
cgcgatattg agcaaaacga gattgttctg acgctgcagt atcagcaatc gaattataat   300
tttaagtgga gaaagattga gatagagggg gtgaaagtta gattagaaaa aaatactcct   360
ggacttagag tattcaattc tcttcacttt gataataata atttgttag cataatagat   420
gaaaaaatat attcaaaaaa taatgaattc gcgtatttga gtagtgattt taaaaatat    480
ataaacgtag agaactatac aagaagtata gctatccccc tagctagtac gatgagtttt   540
gatctttctg taaattattt taatcaaatc aatacctta ataagtaccg agtgttatat    600
aagaaaaaat attatatatt tgaatttgaa atggaaaat tagttaattt tatgcgaggt    660
tataatgacg gttattga                                                  678

<210> SEQ ID NO 5
<211> LENGTH: 25
<212> TYPE: PRT
<213> ORGANISM: Vibrio parahaemolyticus

<400> SEQUENCE: 5

Leu Asn Gln Met Ser Lys Val Glu Ser Arg Asp Ile Asp Leu Ser Phe
1               5                   10                  15

Val Leu Asp Gln Glu Glu Glu Asp Glu
            20                  25

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5

<210> SEQ ID NO 7
<211> LENGTH: 236
<212> TYPE: PRT

<213> ORGANISM: Vibrio parahaemolyticus

<400> SEQUENCE: 7

```
Met Lys Val Cys Arg Ile His Thr Glu Asn Ile Gly Ser Asp Leu Lys
1               5                   10                  15

Ile Asn Ser Asp Arg His Ser Phe Arg Ile His Ser Ile Asn Ser Ser
            20                  25                  30

Ile Ser Glu Lys Gln Leu Leu Glu Lys Leu Lys Ser Cys Phe Pro Ser
        35                  40                  45

Ala Arg Ala Ile Asn Asn Ile Thr Thr His Ser Gln Arg Val Ser Ser
    50                  55                  60

Leu Ser Ala Ala Glu Lys Met Ala Val Asn Leu Tyr Ser Gly Asp Ser
65                  70                  75                  80

Tyr Glu Ser Leu Asn Arg Lys Leu Arg Ser Gly Gln Ser Met Thr Pro
                85                  90                  95

Ala Glu Gln Leu Leu Asp Ile Gly Leu Ser Lys Ala Val Ala Lys Glu
            100                 105                 110

Pro Leu Asp Val Leu Thr Lys Thr Tyr Arg Gly Ser Arg Leu Arg Asp
        115                 120                 125

Ala Phe Gly Ser Val Ala Glu Gly Glu Phe Gly Val Asp Pro Ala Tyr
    130                 135                 140

Leu Ser Thr Ser Arg Asp Pro Glu Ile Ala Cys Glu Phe Ala Glu Glu
145                 150                 155                 160

His Lys Arg Ser Ala Phe Ser Val Ile Phe Gly Val Ser Gly Phe Asp
                165                 170                 175

Met Ala Leu Val Asn Gly Asp Thr Val Glu Ala Glu Val Leu Tyr Pro
            180                 185                 190

Lys Ala Thr Pro Met Arg Val Leu Leu Arg Asp Val Asn Lys Gly Lys
        195                 200                 205

Glu Ser Arg Val Leu Glu Glu Leu Ser Val Ser Glu Thr Gln Gly His
    210                 215                 220

Val Pro Ala Leu Leu Asp Ala Leu Asp Leu Ala Lys
225                 230                 235
```

<210> SEQ ID NO 8
<211> LENGTH: 289
<212> TYPE: PRT
<213> ORGANISM: Vibrio parahaemolyticus

<400> SEQUENCE: 8

```
Met Lys Val Asn Leu Glu Gln Asn His Tyr Tyr Glu Gln Arg Gly Gly
1               5                   10                  15

Ser Asp Leu Arg Glu Gln Leu Ser Ser Tyr Ile Asp Leu Met Asp Asp
            20                  25                  30

Ala Ile Arg Gln Gly Lys Gln Leu Pro Lys Asp Thr Ala Ala Ala Asn
        35                  40                  45

Asp Ile Ala Leu Met Asp Phe Ile Ala Ile Asn Gln Lys Lys
    50                  55                  60

Glu Gly Leu Asn Ala His Phe Phe Arg Ser Pro Leu Asp Met Val Asn
65                  70                  75                  80

Tyr Val Lys Ser Leu Ile Pro Ser Glu Asp Thr Thr Ala Arg Phe Val
                85                  90                  95

Val Asn Met Gly Ser Gly Gly Ile His Cys Ile Ala Val Asp Cys Ala
            100                 105                 110

Ile Lys Asn Gly Lys Cys Ser Leu Ile Gly Ile Asp Pro Val Thr Met
```

-continued

```
                115                 120                 125
Asn Ser Leu Gly Ala Ser Met Leu Ala Ile Arg Leu Gln Ser Val Cys
    130                 135                 140

Lys Arg Glu Leu Pro Glu Thr Ser Leu Val Ile Met Glu Thr Asp Met
145                 150                 155                 160

Gln Arg Ser Gln Gly Glu Cys Leu Met Phe Ser Leu Phe Leu Val Lys
                165                 170                 175

Lys Met His Lys Glu Cys Asp Glu Phe Gln Ser Leu His Asp Lys Asn
            180                 185                 190

Ile Asn Arg Glu Leu Pro Leu Thr Gln Gly Leu Leu Val Ser Val Lys
        195                 200                 205

Asp Ala Asp Ser Leu Leu Pro Pro Ser Leu Met Lys His Thr Gln Ser
    210                 215                 220

Pro Asn Arg Leu Gln Lys Tyr Leu Glu Thr Arg Pro Glu Ala Met Asn
225                 230                 235                 240

Cys Val Val Asn Lys Lys Gly Asp Thr Leu Lys Thr Arg Gln Gln Arg
                245                 250                 255

His Ile Thr Thr Ile Glu Leu Asp Glu Lys Thr Val Ser Tyr Ser Asn
            260                 265                 270

Ser Ile Glu Gln Lys Arg Ile Lys Glu Ala Lys Gly Leu Leu Asn Asn
        275                 280                 285

Leu

<210> SEQ ID NO 9
<211> LENGTH: 484
<212> TYPE: PRT
<213> ORGANISM: Vibrio parahaemolyticus

<400> SEQUENCE: 9

Met Leu Lys Ile Lys Leu Pro Gln Gln Thr Ser Leu Ala Pro Ser Ser
1               5                   10                  15

Glu Thr Thr Gln Arg Leu Pro Val Lys Ile Ser Ile Lys Ser Ile Cys
                20                  25                  30

Asn Lys Ser Ile Cys Lys Thr Leu His Ser Leu Ala Asp Lys Cys His
            35                  40                  45

Arg Phe Ser Lys Glu Ile Lys Gln Arg Ser Ala Asn His Thr Pro Ser
        50                  55                  60

Ser Ser His Glu Asn Leu Thr Thr Ile Asn Leu Lys Ser Gln Asn Ser
65                  70                  75                  80

Ala Ala Thr Phe Glu Ser Thr Val Glu Leu Ser Ile Lys His Gly Ser
                85                  90                  95

Ser Ile Pro Pro Ala Pro Leu Pro Gly Ala Ile Pro Pro Ala Pro
            100                 105                 110

Pro Leu Asn Leu Ser Lys Gly Ala Pro Lys Ser Ser Ser Asn Ser Leu
        115                 120                 125

Asp Ser Val Asn Glu Asp His Ser Lys Leu Met Glu Gln Ile Arg Gln
    130                 135                 140

Gly Val Lys Leu Lys Ser Ala Thr Lys Ser Leu Ser Ala Asp Lys Ser
145                 150                 155                 160

Ser Ala Asp Ala His Ser Lys Leu Met Glu Glu Leu Leu Thr Gly Gly
                165                 170                 175

Arg Lys Leu Lys Lys Val Ala Thr Ser Asp Ile Pro Ala Pro Pro Pro
            180                 185                 190

Leu Pro Ser Ala Ser Thr Ser Lys Ser Pro Asp Ser Arg Asn Ala Leu
```

```
                     195                 200                 205
Leu Ser Glu Ile Ala Gly Phe Ser Lys Asp Arg Leu Arg Lys Thr Gly
    210                 215                 220

Ser Leu Glu Thr Leu Asn Ser Ser Gln Ser Lys Asp Lys Glu Ser Phe
225                 230                 235                 240

Glu Pro Thr Thr His Glu Arg Leu Leu Ser Glu Asp Leu Phe Lys Gln
                245                 250                 255

Ser Pro Lys Leu Ser Glu Gln Glu Leu Asp Glu Leu Ala Asn Asn Leu
            260                 265                 270

Ala Asp Tyr Leu Phe Gln Ala Ala Asp Ile Asp Trp His Gln Val Ile
        275                 280                 285

Ser Glu Lys Thr Arg Gly Leu Thr Thr Glu Glu Met Ala Lys Ser Glu
    290                 295                 300

His Arg Tyr Val Gln Ala Phe Cys Arg Glu Ile Leu Lys Tyr Pro Asp
305                 310                 315                 320

Cys Tyr Lys Ser Ala Asp Val Ala Ser Pro Glu Ser Pro Lys Ser Gly
                325                 330                 335

Gly Gly Ser Val Ile Asp Val Ala Leu Lys Arg Leu Gln Thr Gly Arg
            340                 345                 350

Glu Arg Leu Phe Thr Thr Thr Asp Glu Lys Gly Asn Arg Glu Leu Lys
        355                 360                 365

Lys Gly Asp Ala Ile Leu Glu Ser Ala Ile Asn Ala Ala Arg Met Ala
    370                 375                 380

Ile Ser Thr Glu Glu Lys Asn Thr Ile Leu Ser Asn Asn Val Lys Ser
385                 390                 395                 400

Ala Thr Phe Glu Val Phe Cys Glu Leu Pro Cys Met Asp Gly Phe Ala
                405                 410                 415

Glu Gln Asn Gly Lys Thr Ala Phe Tyr Ala Leu Arg Ala Gly Phe Tyr
            420                 425                 430

Ser Ala Phe Lys Asn Thr Asp Thr Ala Lys Gln Asp Ile Thr Lys Phe
        435                 440                 445

Met Lys Asp Asn Leu Gln Ala Gly Phe Ser Gly Tyr Ser Tyr Gln Gly
    450                 455                 460

Leu Thr Asn Arg Val Ala Gln Leu Glu Ala Gln Leu Ala Ala Leu Ser
465                 470                 475                 480

Ala Lys Leu Ser

<210> SEQ ID NO 10
<211> LENGTH: 1622
<212> TYPE: PRT
<213> ORGANISM: Vibrio parahaemolyticus

<400> SEQUENCE: 10

Met Ala Tyr Asn Ile Ser Leu Asn Asn Ile Thr Thr Thr Thr Ala Pro
1               5                   10                  15

Val Gln Gln Glu Leu Ser Gly Ile Ser Leu Gln Thr Ser Ala Ser Ala
            20                  25                  30

Leu Pro Arg Val Asp Ile Gln Pro Asn Val Asn Glu His Gln Leu Pro
        35                  40                  45

Gln Ala Leu Ser Pro Ser Asp Ser Cys Leu Glu Asn Glu Glu Ser Ser
    50                  55                  60

Ser Gln Gln Pro Glu Val Lys Lys Glu Gln Ala Glu Lys Lys Lys Lys
65                  70                  75                  80

Val His Lys Lys Ser Asn Lys Tyr Ser Asn His Thr Lys Ala Lys Gly
```

```
                85                  90                  95
His Leu Ala Ala Ile Ala Gly Ala Thr Thr Leu Gly Ala Val Leu Ala
            100                 105                 110

Pro Phe Thr Gly Gly Leu Ser Leu Leu Pro Thr Ala Phe Val Val Leu
            115                 120                 125

Phe Gly Asn Ala Ser Ala Leu Ala Met Tyr Gly Gly Ser Glu Phe Val
130                 135                 140

Leu Gly Gln Lys Gly Pro Asn Asn Gln Ile Asp Asp Lys Lys Asp Pro
145                 150                 155                 160

Glu Ala Asn Lys Gln Pro Glu Glu Asn Lys Gln Pro Glu Ile Ser Val
                165                 170                 175

Pro Val Ser Pro Arg Pro Ile Arg Ala Gln Glu Phe Arg Gly Leu Asp
            180                 185                 190

Glu Val Asn Gly Arg Arg Glu Pro Glu Pro Glu Glu Lys Gly Ser Arg
            195                 200                 205

Gly Lys Gly Asp Thr Phe Asn Tyr Ser Pro Val Phe Asn Phe Asn Phe
210                 215                 220

Gly Asp Leu Asn Phe Asn Gln Phe Asn Thr Gln Asn Asn Thr Gln Phe
225                 230                 235                 240

Asn Thr Gln Asn Asn Thr Asp Lys Thr Asn Gln Ala Asp Thr Asp Ser
                245                 250                 255

Ser Pro Thr Leu Ile Glu Gln Thr Ile Glu Lys Phe Gly Gly Asn Pro
            260                 265                 270

Val Ile Asn Val Glu Glu Ile Thr Lys Asp Val Leu Ile Arg Glu Leu
            275                 280                 285

Arg Glu Gln Glu Pro Leu Ile Gly Pro Glu Ser Lys Val Asp Glu Met
290                 295                 300

Ile Asp Ala Leu Val Ser Phe His Glu Gln Thr Asn Glu Ala Lys Leu
305                 310                 315                 320

Ile Gln Val Ser Phe Glu Ser Gly His Lys Ala Tyr Ile Gly Gly Ile
                325                 330                 335

Pro Asp Thr Asp Glu Gln Lys Gln Thr Asp Pro Ile Lys Ala Glu Val
            340                 345                 350

Cys Val Glu Lys Ala Lys Lys Gln Trp Pro Glu Val Lys Pro Ala His
            355                 360                 365

Arg Leu Ile Thr Thr Ser Gly Asn Ala Lys Ile Asp Gly Asn Pro Gly
370                 375                 380

Tyr Arg Asn Ala Arg Val Asp Val Asp Gly Gln Thr Val Gly Tyr Thr
385                 390                 395                 400

Arg Asn Glu Arg Gly Gly Ser Gln Pro Gln Ser Ser Gly Val His Thr
                405                 410                 415

Leu Gln Gly Ser Gln Gln Pro Ser Val Glu Pro Ser Pro Val Asp Pro
            420                 425                 430

Gly His Gly Ala Ser Gly Ala Ser Ala Gln Pro Gly Gly Glu Ala
            435                 440                 445

Lys Gly Ala Gln Thr Pro Ser Leu His Thr Gln Gly Glu Pro Ile Ser
            450                 455                 460

Thr Ala Thr Gln Thr Gly Gly Ala Gln Gly Thr Gln Gly Gly Glu Asp
465                 470                 475                 480

Asp Gly Arg Pro Gln Val Ala Gln Gly His Asn Pro Gln Gly Glu Pro
                485                 490                 495

Ala Ser Leu Ala Lys Ala Gly Thr Pro Val Asp Pro Gly His Gly Ala
            500                 505                 510
```

```
Ser Asp Val Ala Ser Ala Gln Pro Gly Gly Glu Ala Lys Gly Thr Glu
            515                 520                 525

Thr Pro Ser Leu Gln Thr Glu Gly Glu Ser Ile Ser Thr Ser Met Pro
        530                 535                 540

Thr Gly Glu Glu Gln Gly Val Gln Thr Gly Gly Val Lys Lys Trp Pro
545                 550                 555                 560

Glu Val Ala Ala Pro Gln Arg Val Ile Thr Ser Ala Gly Asn Ala Lys
                565                 570                 575

Ile Asp Gly Asn Pro Gly Tyr Arg Asn Ala Arg Val Asp Val Asp Gly
            580                 585                 590

Gln Thr Val Gly Tyr Thr Arg Asn Glu Arg Gly Gly Ser Gln Pro Gln
        595                 600                 605

Ser Ser Gly Val His Thr Leu Gln Gly Ser Gln Gln Pro Ser Val Glu
    610                 615                 620

Pro Ser Pro Val Asp Pro Gly His Gly Ala Ser Gly Ala Ala Ser Ala
625                 630                 635                 640

Gln Pro Gly Gly Glu Ala Lys Gly Ala Gln Thr Pro Ser Leu His Thr
                645                 650                 655

Gln Gly Glu Pro Ile Ser Thr Ser Met Pro Thr Gly Glu Glu Gln Gly
            660                 665                 670

Val Gln Thr Gly Gly Val Lys Lys Trp Pro Glu Val Ala Ala Pro Gln
        675                 680                 685

Arg Val Ile Thr Ser Ala Gly Asn Ala Lys Ile Asp Gly Asn Pro Gly
    690                 695                 700

Tyr Arg Asn Ala Arg Val Asp Val Asp Gly Gln Thr Val Gly Tyr Thr
705                 710                 715                 720

Arg Asn Glu Arg Ser Gly Ser Gln Pro Gln Ser Ser Gly Val His Thr
                725                 730                 735

Leu Gln Gly Ser Gln Gln Pro Ser Val Glu Pro Ser Pro Val Asp Pro
            740                 745                 750

Gly His Gly Ala Ser Gly Ala Ala Ser Ala Gln Pro Gly Gly Glu Ala
        755                 760                 765

Lys Gly Ala Gln Thr Pro Gly Leu His Thr Gln Gly Glu Pro Ile Ser
770                 775                 780

Thr Ala Thr Gln Thr Gly Gly Ala Gln Gly Thr Gln Gly Gly Glu Asp
785                 790                 795                 800

Asp Gly Arg Pro Gln Val Ala Gln Gly His Asn Pro Gln Gly Glu Pro
                805                 810                 815

Ala Ser Leu Ala Lys Ala Gly Thr Pro Val Asp Pro Gly His Gly Ala
            820                 825                 830

Ser Asp Val Ala Ser Ala Gln Pro Gly Gly Glu Ala Lys Gly Thr Gln
        835                 840                 845

Thr Pro Ser Leu Gln Thr Glu Gly Glu Ser Ile Ser Thr Ser Met Pro
    850                 855                 860

Thr Gly Glu Glu Gln Gly Val Gln Thr Gly Gly Val Lys Lys Trp Pro
865                 870                 875                 880

Glu Val Ala Ala Pro Gln Arg Val Ile Thr Ser Ala Gly Asn Ala Lys
                885                 890                 895

Ile Asp Gly Asn Pro Gly Tyr Arg Asn Ala Arg Val Asp Val Asp Gly
            900                 905                 910

Gln Thr Val Gly Tyr Thr Arg Asn Glu Arg Gly Gly Ser Gln Pro Gln
        915                 920                 925
```

```
Ser Ser Gly Val His Thr Ser Gln Gly Ser Gln Gln Pro Gly Val Glu
    930                 935                 940

Pro Ser Pro Val Asp Pro Gly His Gly Ala Ser Gly Ala Ala Ser Val
945                 950                 955                 960

Gln Pro Gly Gly Glu Ala Lys Gly Ala Gln Thr Pro Ser Leu His Thr
                965                 970                 975

Gln Gly Glu Pro Ile Ser Thr Ala Thr Gln Thr Gly Glu Ala Gln Gly
            980                 985                 990

Thr Gln Gly Gly Glu Asp Asp Gly Arg Pro Gln Val Ala Gln Gly His
        995                 1000                1005

Asn Pro Gln Gly Glu Pro Ala Ser Leu Ala Lys Ala Gly Thr Pro
    1010                1015                1020

Val Asp Pro Gly His Gly Ala Ser Gly Ala Ala Ser Ala Gln Pro
    1025                1030                1035

Gly Gly Glu Ala Lys Gly Ala Gln Thr Pro Ser Leu His Thr Gln
    1040                1045                1050

Gly Glu Pro Ile Ser Thr Ala Thr Gln Thr Gly Gly Ala Gln Gly
    1055                1060                1065

Thr Gln Gly Gly Glu Asp Asp Gly Arg Pro Gln Val Ala Gln Gly
    1070                1075                1080

His Asn Pro Gln Gly Glu Pro Ala Ser Leu Ala Lys Ala Gly Thr
    1085                1090                1095

Pro Val Asp Pro Gly His Gly Ala Ser Asp Val Ala Ser Ala Gln
    1100                1105                1110

Pro Gly Gly Glu Ala Lys Gly Ala Gln Thr Pro Ser Leu His Thr
    1115                1120                1125

Gln Gly Glu Pro Ile Ser Thr Ala Thr Gln Thr Gly Gly Ala Gln
    1130                1135                1140

Gly Thr Gln Gly Gly Glu Asp Asp Gly Arg Pro Gln Val Ala Gln
    1145                1150                1155

Gly His Asn Pro Gln Gly Glu Pro Ala Ser Leu Ala Lys Ala Gly
    1160                1165                1170

Thr Pro Val Asp Pro Gly His Gly Ala Ser Gly Ala Ala Ser Ala
    1175                1180                1185

Gln Pro Gly Gly Glu Ala Lys Gly Ala Gln Thr Pro Gly Leu His
    1190                1195                1200

Thr Gln Gly Glu Pro Ile Ser Thr Ala Thr Gln Thr Gly Gly Ala
    1205                1210                1215

Gln Gly Thr Gln Gly Gly Glu Asp Asp Gly Arg Pro Gln Val Ala
    1220                1225                1230

Gln Gly His Asn Pro Gln Gly Glu Pro Ala Ser Leu Ala Lys Ala
    1235                1240                1245

Gly Thr Pro Val Asp Pro Gly His Gly Ala Ser Asp Val Ala Ser
    1250                1255                1260

Ala Gln Pro Gly Gly Glu Ala Lys Gly Thr Gln Thr Pro Ser Leu
    1265                1270                1275

Gln Thr Glu Gly Glu Ser Ile Ser Thr Ser Met Pro Thr Gly Glu
    1280                1285                1290

Glu Gln Gly Val Gln Thr Gly Gly Val Lys Lys Trp Pro Glu Val
    1295                1300                1305

Ala Ala Pro Gln Arg Val Ile Thr Ser Ala Gly Asn Ala Lys Ile
    1310                1315                1320

Asp Gly Asn Pro Gly Tyr Arg Asn Ala Arg Val Asp Val Asp Gly
```

```
         1325                1330                1335

Gln Thr Val Gly Tyr Thr Arg Asn Glu Arg Gly Gly Ser Gln Pro
         1340                1345                1350

Gln Ser Ser Gly Val His Thr Ser Gln Gly Ser Gln Gln Pro Gly
         1355                1360                1365

Val Glu Pro Ser Pro Val Asp Pro Gly His Gly Ala Ser Gly Ala
         1370                1375                1380

Ala Ser Val Gln Pro Gly Gly Glu Ala Lys Gly Ala Gln Thr Pro
         1385                1390                1395

Ser Leu His Thr Gln Gly Glu Pro Ile Ser Thr Ala Thr Gln Thr
         1400                1405                1410

Gly Gly Ala Gln Asn Ile Gln Ser Val Thr Leu Ala Arg Ala Asp
         1415                1420                1425

Leu Gln Gln Thr Asn Val Glu Arg Gly Arg Ile Thr Asp Val Thr
         1430                1435                1440

Lys Leu Val Asp Val Gln Ala Leu Ala Ser Thr Val Ala Ala Asn
         1445                1450                1455

Lys Ser Glu Pro Glu Arg Phe Val Ser Lys Leu His Ile Thr Leu
         1460                1465                1470

Lys Gly Asn Ser Ser Ala Asp Ser Lys Val Gly Thr Asn Gln Pro
         1475                1480                1485

Glu Ser Leu Gln Ala Trp Ser Ser Asn Met Leu Ser His Gly Pro
         1490                1495                1500

Gly Val Lys Leu Ala Gln Lys Ser Leu Val Gln Asn Glu Ile Glu
         1505                1510                1515

Leu Met Pro Gln Ala Asn Asn Gly Glu Thr Val Lys Lys Ile Glu
         1520                1525                1530

Val Val Ser Asn Ile Ser Gly Lys Lys Trp Thr Val Ser Met Pro
         1535                1540                1545

Ala Pro Val Leu Thr Thr Gln Gly Met Ala Ser Gly Arg Gly Lys
         1550                1555                1560

Asn Tyr Thr Gln Gly Leu Phe His Asn Ile Arg Asp Ile Asn Gln
         1565                1570                1575

Thr Lys Arg Asn Ile Glu Leu Asn Ser Thr Leu Met Glu Ser Thr
         1580                1585                1590

Pro Lys Ser Asp Val Ser Phe Val Asn Met Gly Asp Lys Val Ile
         1595                1600                1605

Pro Ile Lys Pro Ala Ile Ile Ser Asn Leu Lys Leu Val Ser
         1610                1615                1620

<210> SEQ ID NO 11
<211> LENGTH: 368
<212> TYPE: PRT
<213> ORGANISM: Vibrio parahaemolyticus

<400> SEQUENCE: 11

Met Pro Ile Leu Asn Ile Ser Lys Phe Ser Asn Thr Glu Tyr Ala Phe
1               5                   10                  15

Val Asn Asn Arg Lys Leu Lys Glu Pro Cys Ile Lys Val Lys Ser Val
            20                  25                  30

Arg Thr Ser Arg Glu Gly Gly Glu Ile Leu Phe Ile Asn Met Pro Ser
        35                  40                  45

Lys Ser Lys Tyr Lys Asp Leu Arg Ala Met Val Lys Ser Ser Val Val
    50                  55                  60
```

-continued

```
Val Ser Glu Ser Asn Gln Thr Ala Ala Ser Lys Phe Glu Asn Asn Ser
 65                  70                  75                  80

Arg Phe Asn Arg Asn Asp Ile Asn Val Lys Lys Ala Asp Ala Lys Ser
                 85                  90                  95

Ile Thr Ala Leu Lys Ser Gly Asp Leu His Ile Leu Lys Gly Lys Gly
            100                 105                 110

Ile Ile Gly Met Lys Gly Gly Asp Asn Lys Leu Pro Phe Lys Cys Thr
            115                 120                 125

Ile Val Asn Asp Asp Lys Asn Gly Ala His Leu Ser Gln Gly Thr Asn
        130                 135                 140

Leu Ala Thr Asn Gly Ile Lys Ser Met Ala Gly Asp Ser Val Arg Ala
145                 150                 155                 160

Ala Gln Leu Ile Pro Gly Thr Pro Leu Gly Gln Phe Tyr Asn Ser Ala
                165                 170                 175

Pro Leu Asp Asp Ser Phe Asn Val Val His Leu Pro Asn Gly Gln Arg
            180                 185                 190

Gly Val Asn Gly Leu Lys Ile Pro Leu Ser Glu Phe Tyr Ser Glu Lys
            195                 200                 205

Lys Phe Leu Phe Ser Asn Gly Ala Leu Ser Gly Cys Met Thr Cys Thr
    210                 215                 220

Ala Ile Asp Lys Asn Asn Leu Tyr Ile Phe His Val Gly Lys Asp Gly
225                 230                 235                 240

Asn Asp Thr Ser Pro Trp Lys Thr Asn Val Asp Gly Ser Ser Leu Ile
                245                 250                 255

Gln Lys Asn Met Lys Met Leu Leu Gly Gln Asn Ser Asp Ser Leu Asn
            260                 265                 270

Asn Gly Ile Gln Gly Leu Ile Asp Tyr Cys Ser Lys Asn Phe Asp Lys
            275                 280                 285

Ala Ile Ile Gln Tyr Cys Gly His Gly Glu Gln Tyr Ser Gly Arg Lys
        290                 295                 300

Asn Ile His Leu Phe Asp Tyr Asn Thr Pro Gln Lys Asn Asn Pro Leu
305                 310                 315                 320

Arg Val Gly Asn Asn Leu Thr Leu Ile Ser His Ser Asp Asn Gly Ser
                325                 330                 335

Leu Ser Ile Ser Thr Leu Cys Asp Asp Met Ile Ile Asn Ser Lys Thr
            340                 345                 350

Cys Glu Thr Asn Ser Val Asn Ser Lys Leu Val Leu Leu Lys Asn Gly
            355                 360                 365
```